(12) United States Patent
Francom et al.

(10) Patent No.: US 8,119,607 B2
(45) Date of Patent: Feb. 21, 2012

(54) BICYCLIC NUCLEOSIDES AND NUCLEOTIDES AS THERAPEUTIC AGENTS

(75) Inventors: Paula Francom, Brea, CA (US); Barbara Frey, Victoria (AU); Silas Bond, Victoria (AU); Alistair George Draffan, Victoria (AU); Michael Harding, Victoria (AU); Richard Hufton, Victoria (AU); Saba Jahangiri, Victoria (AU); Michael John Lilly, Victoria (AU); Edward Tyndall, Victoria (AU); Jianmin Duan, Quebec (CA); Richard Bethell, Montreal (CA); George Kukolj, Quebec (CA)

(73) Assignee: Biota Scientific Management Pty Ltd, Notting Hill (AU)

( * ) Notice: Subject to any disclaimer, the term of this patent is extended or adjusted under 35 U.S.C. 154(b) by 380 days.

(21) Appl. No.: 12/496,311

(22) Filed: Jul. 1, 2009

(65) Prior Publication Data

US 2010/0035836 A1 Feb. 11, 2010

Related U.S. Application Data

(60) Provisional application No. 61/077,972, filed on Jul. 3, 2008.

(51) Int. Cl.
*A01N 43/04* (2006.01)
*A61K 31/70* (2006.01)

(52) U.S. Cl. ............ 514/23; 536/18.7; 536/29.2
(58) Field of Classification Search ............ None
See application file for complete search history.

(56) References Cited

U.S. PATENT DOCUMENTS

| | | | |
|---|---|---|---|
| 4,584,369 A | 4/1986 | Klein et al. | |
| 6,320,035 B1 | 11/2001 | Muhlegger et al. | |
| 6,630,476 B2 | 10/2003 | Bakthavatchalam | |
| 6,734,185 B2 | 5/2004 | Bakthavatchalam | |
| 6,777,395 B2 | 8/2004 | Bhat et al. | |
| 7,094,768 B2 | 8/2006 | Roberts et al. | |
| 7,105,499 B2 | 9/2006 | Carroll et al. | |
| 7,125,855 B2 | 10/2006 | Bhat et al. | |
| 7,202,224 B2 | 4/2007 | Eldrup et al. | |
| 7,285,658 B2 | 10/2007 | Cook et al. | |
| 7,319,102 B1 | 1/2008 | Clark et al. | |
| 7,323,453 B2 | 1/2008 | Olsen et al. | |
| 7,329,666 B2 | 2/2008 | Alvarez et al. | |
| 2003/0087873 A1 | 5/2003 | Stuyver et al. | |
| 2004/0014108 A1 | 1/2004 | Eldrup et al. | |
| 2004/0063658 A1 | 4/2004 | Roberts et al. | |
| 2004/0147464 A1 | 7/2004 | Roberts et al. | |
| 2004/0259934 A1 | 12/2004 | Olsen et al. | |
| 2005/0031588 A1 | 2/2005 | Sommadossi et al. | |
| 2005/0272676 A1 | 12/2005 | Bhat et al. | |
| 2006/0019957 A1 | 1/2006 | Crew et al. | |
| 2006/0084654 A1 | 4/2006 | Beck et al. | |
| 2006/0154929 A1 | 7/2006 | Anker et al. | |
| 2006/0205686 A1 | 9/2006 | Bhat et al. | |
| 2006/0235031 A1 | 10/2006 | Arnold et al. | |
| 2006/0258613 A1 | 11/2006 | Roberts et al. | |
| 2006/0264389 A1 | 11/2006 | Bhat et al. | |
| 2007/0032448 A1 | 2/2007 | Hong et al. | |
| 2007/0265222 A1 | 11/2007 | MacCoss et al. | |
| 2007/0275912 A1 | 11/2007 | Bhat et al. | |
| 2008/0033001 A1 | 2/2008 | Alvarez et al. | |

FOREIGN PATENT DOCUMENTS

| | | |
|---|---|---|
| WO | 02057287 | 7/2002 |
| WO | 02098880 | 12/2002 |
| WO | 03151899 | 6/2003 |
| WO | 03061576 | 7/2003 |
| WO | 03093290 | 11/2003 |
| WO | 03100017 | 12/2003 |
| WO | 2004028481 | 4/2004 |
| WO | 2005020885 | 3/2005 |
| WO | 2005037836 | 4/2005 |
| WO | 2006116512 | 11/2006 |
| WO | 2007064931 | 6/2007 |
| WO | 2008089105 | 7/2008 |

OTHER PUBLICATIONS

Il'icheva et al. Russian Journal of Bioorganic Chemistry (2005), vol. 31, No. 5, pp. 439-452.*

* cited by examiner

*Primary Examiner* — Patrick Lewis
(74) *Attorney, Agent, or Firm* — Quarles & Brady LLP; Thomas R. Stiebel, Jr.; John E. Conour

(57) ABSTRACT

The present disclosure relates to the use and methods of manufacture of bicyclic nucleosides and nucleotides for the treatment and prevention of infectious and proliferative diseases, including microbial infections and cancer.

32 Claims, No Drawings

BICYCLIC NUCLEOSIDES AND NUCLEOTIDES AS THERAPEUTIC AGENTS

CROSS REFERENCE TO RELATED APPLICATIONS

This application claims the benefit of U.S. Provisional Application Ser. No. 61/077,972, filed Jul. 3, 2008, and is hereby incorporated herein by reference in its entirety.

STATEMENT CONCERNING GOVERNMENT INTEREST

Not applicable.

SEQUENCE LISTINGS

Not applicable.

BACKGROUND OF THE DISCLOSURE

Nucleoside drugs have been used clinically for decades for the treatment of viral infections and proliferative disorders such as cancer. Most nucleoside drugs (analogues) are classified as antimetabolites. After they enter cells, nucleoside analogues are phosphorylated successively to nucleotide 5'-mono-phosphates, 5'-di-phosphates, and 5'-tri-phosphates. In some cases, nucleotide tri-phosphates, e.g., 3'-azido-3'-deoxythymidine tri-phosphate (AZT, an anti-human immunodeficiency virus (HIV) drug) and arabinosylcytosine tri-phosphate (cytarabine, an anticancer drug), are the active chemical entities that inhibit DNA or RNA synthesis through competitive inhibition of polymerases and subsequent incorporation of modified nucleotides into DNA or RNA sequences. In a few cases, nucleoside analogues exert effects as their 5'-monophosphate or 5'-diphosphate. For instance, 5-fluoro-2'-deoxyuridine 5'-mono-phosphate (an anticancer drug) and 2',2'-difluoro-2'-deoxycytidine 5'-di-phosphate (an anticancer drug) have been shown to inhibit thymidylate synthase and ribonucleotide reductase, respectively. Although unphosphorylated nucleoside analogues themselves may act as adenosine kinases inhibitors and adenosine receptor ligands, currently, clinically-useful nucleoside drugs primarily depend on cellular activation by nucleoside and nucleotide kinases.

Viral infections are a major threat to human health and account for many serious infectious diseases. The most notable viruses are the blood-borne viruses (BBV), which include hepatitis C virus (HCV), hepatitis B virus (HBV) and HIV, which are all linked by their mode of transmission, i.e., through blood or bodily fluids.

The Flaviviridae is a group of positive single-stranded RNA viruses with a genome size from 9-15 kilobases (kb). The Flaviviridae consist of various genera including *Flavivirus* and *Hepacivirus*. *Flavivirus* includes Dengue, Japanese Tick-Borne, and Yellow Fever viruses. Apart from these major groups, there are some additional *Flavivirus* that are unclassified. *Hepacivirus* include only one species, the Hepatitis C virus, which is composed of many genotypes and subtypes.

Hepatitis C virus is a major cause of viral hepatitis and has infected more than 200 million people worldwide. Hepatitis C virus has a positive-strand RNA genome enclosed in a nucleocapsid and lipid envelope. The HCV genome is approximately 9.6 kb in length and encodes a polyprotein of about 3,000 amino acids (Dymock et al. *Antiviral Chemistry & Chemotherapy* 2000, 11, 79). Current treatment for HCV infection is restricted to immunotherapy with interferon-α alone or in combination with ribavirin, a nucleoside analogue. However, this treatment is effective in only about half the patient population. Recently, several PCT patent applications (WO 99/43691, WO 01/32153, WO 01/60315, WO 01/79246, WO 01/90121, WO 01/92282, WO 02/18404, WO 02/057287, and WO 02/057425) have described nucleoside analogues as anti-HCV agents in in vitro assays.

Hepatitis B virus has acutely infected almost a third of the human population, and about 5% of the infected are chronic carriers of the virus (Delaney W E et al., *Antiviral Chemistry & Chemotherapy* 2001, 12, 1-35). Chronic HBV infection causes liver damage that frequently progresses to cirrhosis and/or liver cancer later in life. Despite the availability and widespread use of effective vaccines and chemotherapy, the number of chronic HBV carriers approaches 400 million worldwide.

Human immunodeficiency virus causes progressive degeneration of the immune system, leading to the development of AIDS. A number of drugs have been used clinically to treat AIDS, including reverse transcriptase inhibitors and protease inhibitors. Currently, combination therapies are used widely for the treatment of AIDS in order to reduce drug resistance. Despite the progress in the development of anti-HIV drugs, AIDS is still one of the leading epidemic diseases.

Apart from the BBV's discussed above, certain other acute viral infections also pose a great threat to human life, including infections of Herpes Simplex virus (HSV), cytomegalovirus (CMV), influenza viruses, West Nile virus, Coronaviruses, causing for example, severe acute respiratory syndrome (SARS), Variola virus (causing smallpox), Epstein-Barr virus (EBV), *Varicella zoster* virus (VZV), and Human respiratory syncytial virus (RSV). Accordingly, the broad range of associated infectious diseases and the propensity for viral mutation highlight the continued need for the development of different antiviral drugs.

Bacterial infections have long been the source of many infectious diseases. The widespread use of antibiotics has produced many new strains of life-threatening antibiotic resistant bacteria. Fungal infections are another type of infectious disease, some of which are also life-threatening. There is an ever increasing demand for the treatment of bacterial and fungal infections. As such, antimicrobial drugs based on new mechanisms of action are especially important.

Proliferative disorders (for example, cancer) are some of the most life-threatening diseases today and have been investigated intensively for decades. Cancer is currently the second leading cause of death in the United States, and over 500,000 people die annually from this proliferative disorder. All of the various nucleated cell types of the body can be transformed into benign or malignant tumour cells. Transformation of normal cells into cancer cells is a complex process and is not understood fully. Cancer treatment includes primarily surgery, radiation therapy, and chemotherapy. While chemotherapy can be used to treat many types of cancer, surgery and radiation therapy are limited to certain cancers at certain sites of the body. There are a number of anticancer drugs widely used clinically. Among them are alkylating agents, such as cisplatin, and antimetabolites, such as 5-fluorouracil and gemcitabine. Although surgery, radiation therapy, and chemotherapy are available to treat cancer patients, there is no cure for cancer at the present time. Cancer research remains one of the most important focuses of medical and pharmaceutical organizations.

Numerous examples exist in the literature for the synthesis of a variety of modified nucleosides (Chemistry of Nucleosides and Nucleotides, Vol. 1 (1988), Vol. 2 (1991), Vol. 3 (1994), edited by Leroy B. Townsend, Plenum Press). However, there are certain classes of nucleoside compounds that have not been explored fully for their antiviral and antiproliferative activities. One such class is the bicyclic nucleosides.

Similarly, cycloalkyl-substituted bicyclic nitrogenous base analogues are being employed as protein kinase inhibitors to combat uncontrolled cell growth, such as is described in U.S. Patent Application Publication No. 2007/0203143.

SUMMARY OF THE DISCLOSURE

In one aspect of the present disclosure, a compound is provided according to the structure of formula I:

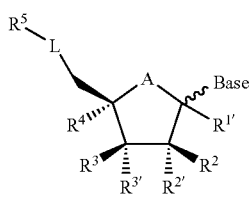

I wherein the ∼∼∼ defines the active pharmaceutical ingredient as a D- or L-nucleoside or nucleotide; A is selected from the group consisting of —O—, —S—, —CH$_2$—, —CHF—, —CF$_2$—, and —NR—; R$^{1'}$, R$^2$, R$^{2'}$, R$^1$, R$^{3'}$, and R$^4$ are independently selected from the group consisting of —H, halogen, —OH, —NHOH, —NHNH$_2$, —N$_3$, —CN, —OCOCHNC(CH$_3$)$_2$, —COOH, —CONH$_2$, —C(S)NH$_2$, —COOR, —R, —OR, —SR, —SSR, —NHR, and —NR$^2$, or R$^2$ and R$^{2'}$ together or R$^3$ and R$^{3'}$ together represents =O, =S, or =L'—Y', where L' is selected from the group consisting of N, CH, CF, CCl, and CBr and Y' is selected from the group consisting of H, halogen, N$_3$, methyl, ethyl, and CN; R is independently halogen, —H, —OH, —SH, —CN, S(C$_1$-C$_4$alkyl), —NO$_2$, NH$_2$, —NHNH$_2$, —N$_3$, —NR'R' wherein each R' is independently H or C$_1$-C$_4$ alkyl, —C(S)NH$_2$, —CH$_3$, —CH$_2$OH, —CH$_2$NH$_2$, —CH$_2$NH$_3^+$, —COOH, —COOCH$_3$, —COOCH$_2$CH$_3$, —CONHCH$_3$, —CONH$_2$, —CF$_3$, —N(CH$_3$)$_2$, —NHCOCH$_3$, —NHCONH$_2$, —NHCNHNH$_2$, —ONH$_2$, —CH$_2$OCH$_3$, —O(CH$_2$)CH$_3$, COOC$_1$-C$_4$alkyl, optionally substituted alkyl, optionally substituted alkenyl, optionally substituted alkynyl, optionally substituted aryl, optionally substituted acyl, optionally substituted arylalkyl, optionally substituted cycloalkyl, optionally substituted cycloalkenyl, optionally substituted phenyl, optionally substituted heteroaryl, optionally substituted heterocyclyl, optionally substituted alkyloxy, optionally substituted alkenyloxy, optionally substituted alkynoxy, optionally substituted aryloxy, optionally substituted acyloxy, optionally substituted oxyacyl, optionally substituted arylalkoxy, optionally substituted heterocycloxy, optionally substituted heteroaryloxy, optionally substituted cycloalkoxy, optionally substituted cycloalkenoxy, optionally substituted amino, optionally substituted aminoacyl, optionally substituted aminoacyloxy, optionally substituted acylamino, optionally substituted oxyacylamino, optionally substituted oxyacyloxy, optionally substituted acylimino, optionally substituted acyliminoxy, optionally substituted oxyacylimino, optionally substituted aminothioacyl, optionally substituted thioacylamino, optionally substituted aminosulfinyl, optionally substituted aminosulfonyl, optionally substituted thio, optionally substituted thioalkyl, optionally substituted thioacyl, optionally substituted thioacyloxy, optionally substituted oxythioacyl, optionally substituted oxythioacyloxy, optionally substituted phosphorylamino, optionally substituted sulfinyl, optionally substituted sulfonyl, optionally substituted sulfinylamino, optionally substituted sulfonylamino, optionally substituted oxysulfinylamino, and optionally substituted oxysulfonylamino; L is selected from the group consisting —O, —S, —NH, —NR, —CY$_3$, —CY$_2$O, —CY$_2$S, —CY$_2$NH, —CY$_2$, —CY$_2$CY$_2$, —CY$_2$OCY$_2$, —CY$_2$SCY$_2$, and —CY$_2$NHCY$_2$; Y is independently selected from the group consisting of —H, halogen, —R, —OR, and —NR$^2$; R$^5$ is selected from the group consisting of —OH, —R, —OR, —NR$_2$, or a mono-phosphate, di-phosphate, or tri-phosphate moiety or mimic thereof; Base is a group of formula II:

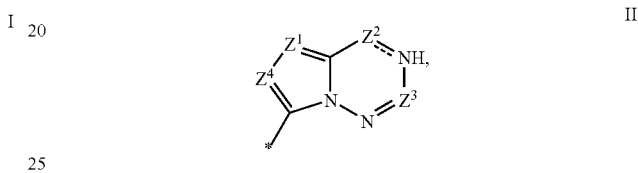

II wherein the dashed line ----- is a single or double bond; Z$^1$, Z$^3$, and Z$^4$ are independently selected from the group consisting of >C—CONHR, >C—CONR$_2$, >C—C(S)NH$_2$, >C—COOR, >C—R, >C—OR, >C—SR, >C—NHR, >C—NR$_2$, >C-optionally substituted heteroaryl, >C-optionally substituted alkyl, and >C-G; Z$^2$ is selected from the group consisting of >C—NH$_2$ and >C=O; G is independently selected from the group consisting of —H, —F, —Cl, —I, —NH$_2$, —NHCH$_3$, —CN, —COOH, —CSNH$_2$, —C≡CH, —C≡CCH$_3$, —C≡CCH$_2$OH, —C≡C—Si(CH$_3$)$_3$, —CONH$_2$, —CONHCH$_3$, —CONH-phenyl, —CONH-methylphenyl, thiazole, oxazole, imidazole, imidazoline, triazole, and tetrazole, and when the compound comprises two or more G groups, the G's are identical or different; and when A is O; R$^{1'}$, R$^3$, R$^4$, and R$^5$ are H; L is O; and R$^{2'}$ and R$^{3'}$ are OH; then R$^2$ is halogen, OH, NHOH, NHNH$_2$, N$_3$, CN, OCOCHNC(CH$_3$)$_2$, COOH, CONH$_2$, C(S)NH$_2$, COOR, R$^6$, OR, SR, SSR, NHR, or NR$_2$, and R$^6$ is halogen, OH, SH, CN, S(C$_{1-4}$ alkyl), NO$_2$, NH$_2$, NHNH$_2$, N$_3$, NR'R' wherein each R' is independently H or C$_{1-4}$ alkyl, C(S)NH$_2$, CH$_3$, CH$_2$OH, CH$_2$NH$_2$, CH$_2$NH$_3^+$, COOH, COOCH$_3$, COOCH$_2$CH$_3$, CONHCH$_3$, CONH$_2$, CF$_3$, N(CH$_3$)$_2$, NHCOCH$_3$, NHCONH$_2$, NHCNHNH$_2$, ONH$_2$, CH$_2$OCH$_3$, O(CH$_2$)CH$_3$, COO(C$_{1-4}$ alkyl), substituted alkyl, substituted alkenyl, substituted alkynyl, substituted aryl, substituted acyl, substituted arylalkyl, substituted cycloalkyl, substituted cycloalkenyl, substituted phenyl, substituted heteroaryl, substituted heterocyclyl, substituted alkyloxy, substituted alkenyloxy, substituted alkynoxy, substituted aryloxy, substituted acyloxy, substituted oxyacyl, substituted arylalkoxy, substituted heterocycloxy, substituted heteroaryloxy, substituted cycloalkoxy, substituted cycloalkenoxy, substituted amino, substituted aminoacyl, substituted aminoacyloxy, substituted acylamino, substituted oxyacylamino, substituted oxyacyloxy, substituted acylimino, substituted acyliminoxy, substituted oxyacylimino, substituted aminothioacyl, substituted thioacylamino, substituted aminosulfinyl, substituted aminosulfonyl, substituted thio, substituted thioalkyl, substituted thioacyl, substituted thioacyloxy, substituted oxythioacyl, substituted oxythioacyloxy, substituted phosphorylamino, substituted sulfinyl, substituted sulfonyl, substituted sulfinylamino, substituted sulfonylamino, substituted oxysulfinylamino, or, substituted oxysulfonylamino; or a pharmaceutically-acceptable salt, ester, solvate, hydrate, or prodrug thereof.

In one embodiment of a compound of formula I, the ----- is a double bond, $Z^1$ is >C—R", $Z^2$ is >C—NH$_2$, $Z^3$ is >C—R"', $Z^4$ is >C—R"", and R", R"' and R"" are each independently H, F, I, Cl, NH$_2$, NHCH$_3$, C(=O)NH$_2$, C(=O)NHCH$_3$, C(=O)NH(C$_6$H$_5$), C(=O)NH(C$_6$H$_5$CH$_2$), CN, C≡CH, C≡CCH$_3$, C≡CCH$_2$OH, C≡C—Si(CH$_3$)$_3$, C(=S)NH$_2$, CO$_2$H,

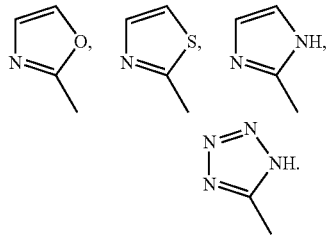

In yet another embodiment of a compound of formula I, the ----- is a single bond, $Z^1$ is >C—R", $Z^2$ is >C=O, $Z^3$ is >C—R"', $Z^4$ is >C—R"", and R", R"' and R"" are each independently H, F, I, Cl, NH$_2$, NHCH$_3$, C(=O)NH$_2$, C(=O)NHCH$_3$, C(=O)NH(C$_6$H$_5$), —C(=O)NH(CH$_2$C$_6$H$_5$), CN, C≡CH, C≡CCH$_3$, C≡CCH$_2$OH, C≡C—Si(CH$_3$)$_3$, C(=S)NH$_2$, CO$_2$H,

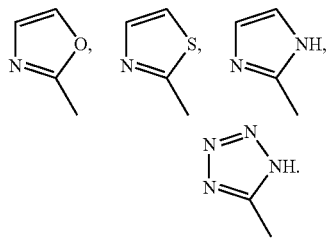

In still another embodiment of a compound of formula I, $Z^4$ is >C—H.

In still another embodiment of a compound of formula I, $Z^4$ is >C—R"", and R"" is F, I, Cl, NH$_2$, NHCH$_3$, C(=O)NH$_2$, C(=O)NHCH$_3$, C(=O)NHC$_6$H$_5$, C(=O)NH(CH$_2$C$_6$H$_5$), CN, C≡CH, C≡CCH$_3$, C≡CCH$_2$OH, C—C≡Si(CH$_3$)$_3$, C(=S)NH$_2$, CO$_2$H,

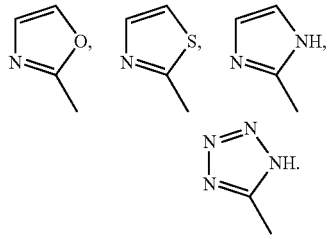

In still another embodiment of a compound of formula I, R"" is F, I or Cl.

In still another embodiment of a compound of formula I, $Z^3$ is >C—R"', and R"' is H.

In still another embodiment of a compound of formula I, $Z^3$ is >C—R"', and R"' is NH$_2$.

In still another embodiment of a compound of formula I, $Z^1$ is >C—H.

In still another embodiment of a compound of formula I, $Z^1$ is >C—R", and R" is independently F, I, Cl, NH$_2$, NHCH$_3$, C(=O)NH$_2$, C(=O)NHCH$_3$, C(=O)NHC$_6$H$_5$, C(=O)NHCH$_2$C$_6$H$_5$, CN, C≡CH, C≡CCH$_3$, C≡CCH$_2$OH, C—C≡—Si(CH$_3$)$_3$, C(=S)NH$_2$, CO$_2$H,

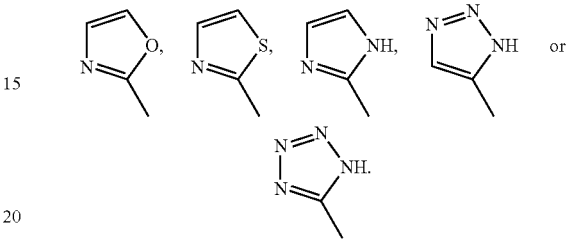

In still another embodiment of a compound of formula I, A is oxygen.

In still another embodiment of a compound of formula I, L is O, and $R^5$ is H or the mono-, di- or tri-phosphate moiety or mimic thereof.

In still another embodiment of a compound of formula I, $R^5$ is a phosphoramidate or a phosphoester of the mono-, di- or tri-phosphate moiety.

In still another embodiment, a compound of formula I is selected from
4-amino-5-fluoro-7-(2-C-methyl-β-D-ribofuranosyl)-pyrrolo[2,1-f][1,2,4]triazine;
4-amino-5-chloro-7-(2-C-methyl-β-D-ribofuranosyl)-pyrrolo[2,1-f][1,2,4]triazine;
4-Amino-5-iodo-(2-C-methyl-β-D-ribofuranosyl)-pyrrolo[2,1-f][1,2,4]triazine;
4-amino-7-(2-C-methyl-β-D-ribofuranosyl)-pyrrolo[2,1-f][1,2,4]triazine-5-carbonitrile;
4-amino-7-(2-C-methyl-β-D-ribofuranosyl)-pyrrolo[2,1-f][1,2,4]triazine-5-carboxylic acid amide;
4-amino-5-trimethylsilanylethynyl-7-(2-C-methyl-β-D-ribofuranosyl)-pyrrolo[2,1-f][1,2,4]triazine;
4-amino-5-ethynyl-7-(2-C-methyl-β-D-ribofuranosyl)-pyrrolo[2,1-f][1,2,4]triazine;
4-amino-7-(2-C-methyl-β-D-ribofuranosyl)-pyrrolo[2,1-f][1,2,4]triazine-5-carboxylic acid; 2,4-diamino-7-(2-C-methyl-β-D-ribofuranosyl)-pyrrolo[2,1-f][1,2,4]triazine;
4-amino-7-(2-C-methyl-β-D-ribofuranosyl)-pyrrolo[2,1-f][1,2,4]triazine-5-carbothioic acid amide;
4-amino-5-oxazol-2-yl-7-(2-C-methyl-β-D-ribofuranosyl)-pyrrolo[2,1-f][1,2,4]triazine;
4-amino-5-thiazol-2-yl-7-(2-C-methyl-β-D-ribofuranosyl)-pyrrolo[2,1-f][1,2,4]triazine;
4-amino-5-(3H-[1,2,3]triazol-4-yl)-7-(2-C-methyl-β-D-ribofuranosyl)-pyrrolo[2,1-f][1,2,4]triazine;
4-Amino-6-fluoro-7-(2-C-methyl-β-D-ribofuranosyl)-pyrrolo[2,1-f][1,2,4]triazin-7-yl;
4-amino-5-imidazole-7-(2-C-methyl-β-D-ribofuranosyl)-pyrrolo[2,1-f][1,2,4]triazine; and
4-amino-5-imidazoline-7-(2-C-methyl-β-D-ribofuranosyl)-pyrrolo[2,1-f][1,2,4]triazine.

In still another embodiment, a compound of formula I is 4-amino-7-(2-C-methyl-β-D-ribofuranosyl)-pyrrolo[2,1-f][1,2,4]triazine.

In still another embodiment of a compound of formula I, $R^5$ is a phosphoramidate or a phosphoester of the mono-, di- or tri-phosphate moiety.

In still another embodiment, the compound of formula I is

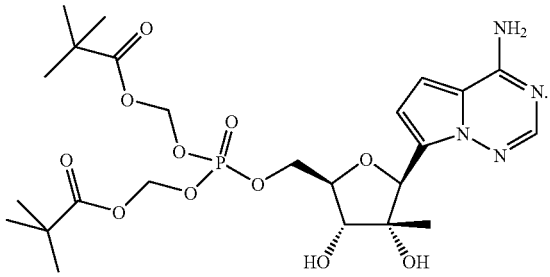

In still another embodiment, the compound of formula I is

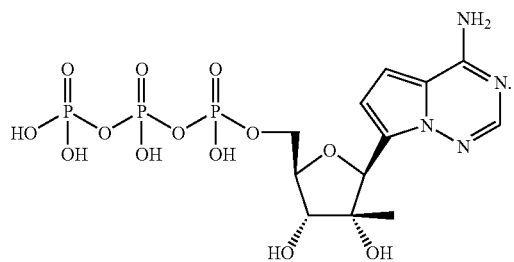

In another embodiment of the present disclosure, a pharmaceutical dosage form comprises a therapeutically effective amount of a compound of formula I, a salt, ester, solvate, hydrate or prodrug thereof, and one or more pharmaceutically acceptable carriers, diluents and/or excipients.

In still another embodiment, a pharmaceutical dosage form is adapted for once-daily dosing.

In still another embodiment, a pharmaceutical dosage form comprises a therapeutically effective amount of 4-amino-7-(2-C-methyl-β-D-ribofuranosyl)-pyrrolo[2,1-f][1,2,4]triazine.

In still another embodiment, a method of treating or preventing a microbial infection, a viral infection, or a proliferative disorder comprises administering a therapeutically effective amount of a compound of formula I or a pharmaceutical dosage form thereof to a patient suffering from or at risk of a microbial infection, a viral infection or a proliferative disorder. In one embodiment, the viral infection is a hepatitis C viral infection.

In yet another embodiment, the method comprises administering a therapeutically effective amount of a compound of formula I or a pharmaceutical dosage form thereof to a patient once-daily.

In yet another embodiment, the method comprises administering a compound of formula I to the patient in the range of about 10 μg/kg to about 30 mg/kg.

In yet another embodiment, the method comprises administering about 10 μg/kg to about 30 mg/kg of 4-amino-7-(2-C-methyl-β-D-ribofuranosyl)-pyrrolo[2,1-f][1,2,4]triazine to a patient.

In yet another embodiment, the method comprises administering a therapeutically effective amount of a compound of formula I to a patient once-daily in the range of about 10 μg/kg to about 30 mg/kg.

In yet another embodiment, a method of inhibiting polymerase activity in a human patient comprises administering a therapeutically effective amount of a compound of formula I or a pharmaceutical dosage form thereof to the human patient.

In yet another embodiment, a method comprises inhibiting HCV NS5B polymerase activity.

In yet another embodiment, a method comprises the in-vivo production of a therapeutically effective metabolite of a compound of formula I that has an intracellular half-life of greater than about 10 hours.

In yet another embodiment, a method comprises the in-vivo production of a sufficient amount of a therapeutically effective metabolite of a compound of formula I to allow for once a day dosing of the compound of formula I in a human patient in the range of about 10 μg/kg to about 30 mg/kg, or about 15 μg/kg to about 25 mg/kg.

In yet another embodiment, a method comprises administering to a patient a compound of formula I that has a plasma half life great than about 2 hours in the patient

DETAILED DESCRIPTION OF THE EXEMPLARY EMBODIMENTS

The present disclosure is directed to methods of treatment, kits, combinations, compounds including their use in the manufacture of medicaments, and compositions that exhibit antiproliferative effects, for example, via the inhibition of DNA and/or RNA synthesis and that particularly may inhibit activity of one or more polymerases, or that treat a condition where treatment with a polymerase inhibitor, such as a DNA and/or RNA synthesis inhibitor, is indicated. In one embodiment, a DNA and/or RNA synthesis inhibitor includes a bicyclic nucleoside and/or nucleotide, having activity as a polymerase inhibiting agent.

While the present disclosure may be embodied in many different forms, several specific embodiments are discussed herein with the understanding that the present disclosure is to be considered only as an exemplification of the principles of the invention, and does not limit the invention to the embodiments illustrated. For example, where the invention is illustrated herein with particular reference to a compound having inhibitory activity against an HCV NS5B polymerase, it will be understood that other polymerases can, if desired, be substituted in whole or in part for the HCV polymerase herein described.

Although not wishing to be bound by theory, it is believed that a microbial and/or a proliferative disease or disorder may be treated, attenuated, and/or prevented through manipulation of polymerase activity by using a compound herein described. For example, one microbial polymerase target, NS5B, an HCV protein, is released from a polyprotein and is involved in the synthesis of double-stranded RNA from a single-stranded viral RNA genome. It is believed that the replication and/or reproduction of HCV virus may be inhibited or prevented through the inhibition of NS5B and suppress or prevent the formation of the double-stranded HCV RNA. Alternatively, it is also believed that a nucleoside analogue also may be incorporated into the extending RNA strand to act as a chain-terminator and/or lead to null mutations. Furthermore, it is believed that a nucleoside analogue or a derived metabolite also may be incorporated into the extending RNA, which may cause mutagenic damage to the viral genome.

It is also believed that proliferative disorders including, for example, acute myelogenous leukemia, cholangiocarcinoma, chronic myelogenous leukemia, lymphoma, melanoma, multiple myeloma, osteosarcoma, gastric sarcoma, glioma, bladder, breast, cervical, colorectal, lung, liver, ovarian, pancreatic, prostrate, or stomach cancer, and non-cancerous diseases associated with excessive and/or inappropriate cell growth, including endothelial cell growth associated with restenosis such as coronary, carotid, and cerebral lesions, may also be inhibited and/or prevented through the manipulation of polymerase activity by the compounds described herein, such as D- and/or L-nucleosides and nucleotides of formula I below. Further, decreases in proliferation rates of highly proliferative and/or cancerous cells may be achieved in a manner similar to those described above, namely, that antiproliferative nucleoside analogues may be incorporated into the RNA and/or replicating genomes of highly proliferative and/or cancerous cells causing, for example, chain-terminator, frame shift, and/or null mutations that disrupt downstream effector mechanisms required for cell proliferation and metabolic homeostasis.

Such compounds may be screened for antiproliferative and/or polymerase inhibitory activity by in vitro or in vivo methods known to those skilled in the art in addition to the methods set forth herein Still further, and not wishing to be bound by theory, it is believed that one or more criteria are desirable for a nucleoside antiviral and/or antiproliferative drug, including, for example, that the nucleoside analogue anabolises to a nucleotide in cells, and/or that the anabolised nucleotide selectively targets viral proteins and/or proliferative mechanisms including, for example, peptide- and/or nucleic acid-based enzymes. It is believed that in order to be phosphorylated in cells and selectively target preferred enzymes, nucleoside analogues may have favourable modifications on their sugar and base moieties. To obtain such favourable nucleoside analogues, a general approach is to generate diverse nucleoside analogues by modifying the base or the sugar or by modifying both base and sugar moieties. Numerous examples exist in the literature for the synthesis of a variety of modified nucleosides, including, for example, *Chemistry of Nucleosides and Nucleotides* Vol. 1 (1988), Vol. 2 (1991), Vol. 3 (1994), edited by L. B. Townsend, Plenum Press; *Handbook of Nucleoside Synthesis* by H. Vorbrüggen and C. Ruh-Pohlenz, John Wiley & Sons, Inc., 2001; and *The Organic Chemistry of Nucleic Acids* by Y. Mizuno, Elsevier, 1986. The resulting modified compounds can then be assayed for desired activity as discussed more fully herein.

While nucleosides incorporating a variety of sugar moieties have been found useful for the inhibition of viral polymerases, in the case of the Flaviviridae, and in particular HCV, 2'-C-methyl ribonucleosides have been found to be useful (see Eldrup, A. B. et al., J. Med. Chem. 2004, 47(21), 5284-97).

The terms "infection" and "microbial infection" (and variations thereof) refers to an infection caused by an infectious agent or microbe, used herein to include at least bacteria, parasites (including protozoa), viruses, and fungi (including unicellular and multicellular). Examples of microbes and microbial infections include: *Acanthamoeba*, *Trypanosoma brucei*, which causes African sleeping sickness, *Entamoeba histolytica*, which causes amebiasis, *Trypanosoma cruzi*, which causes American trypanosomiasis or Chagas disease, *Schistosoma* sp., which cause schistosomiasis or bilharzia, *Cryptosporidium parvum*, which causes cryptosporidiosis, *Giardia lamblia*, which causes giardiasis, hepatitis A, B, C, D, and E, *Leishmania* sp., which cause cutaneous and visceral leishmaniasis, *Plasmodium falciparum*, which causes malaria, *Salmonella enteritides*, which causes stomach cramps, diarrhea and fever, *Mycobacterium tuberculosis*, which causes tuberculosis, *Varicella zoster* virus, which causes chicken pox, yellow fever virus, pneumonia, *Chlamy-* *dia* and *Mycoplasma* sp., which cause, for example, urinary tract infections, meningitis and meningococcal septicemia, *Staphylococcus aureus*, which causes skin and soft tissue infections, and lower respiratory tract infections (bacterial pathogens or viral pathogens).

Additional common infections caused by microbes include, but are not limited to, those outlined in the following chart:

| Infection | Bacteria | Fungus | Protozoa | Virus |
|---|---|---|---|---|
| AIDS | | | | X |
| Athlete's Foot | | X | | |
| Chicken Pox | | | | X |
| Common Cold | | | | X |
| Diarrheal Disease | X | | X | X |
| Dengue | | | | X |
| Flu | | | | X |
| Genital Herpes | | | | X |
| Malaria | X | | X | |
| Meningitis | X | | | |
| Pneumonia | X | X | | |
| Sinusitis | X | X | | |
| Skin Disease | X | X | X | X |
| Strep Throat | X | | | |
| Tuberculosis | X | | | |
| Urinary Tract Infections | X | | | |
| Vaginal Infections | X | X | | |
| Viral Hepatitis | | | | X |

In relation to therapeutic methods of the present disclosure, compounds of formula I can be useful for inhibiting a polymerase, including, for example, HCV NS5B polymerase and/or microbial replication, such as HCV replication and treating a microbial infection, such as HCV infection. Hosts that can be treated may include a unicellular organism, including a cell line, or a multicellular organism such as an animal, which may have one or more host-specific and/or invasive proteins encoded within their genomes and functioning in parallel with host proliferative mechanisms or in collaboration with host mechanism in effect to form new virions, for example, or to alter normal host proliferative patterns. For example, a host includes infected cells, cells transfected with all or part of a genome encoding a polymerase, such as the HCV genome, or an animal having a proliferative disorder or a microbial infection such as a viral infection caused by an RNA virus, including, for example, a virus belonging to group Flaviviridae, for instance *Flaviviruses* or HCV, or a DNA or retrovirus such as HBV or HIV.

In one embodiment, a method of the present disclosure treats a viral infection caused by an RNA virus of the group Flaviviridae and in particular HCV. An illustrative process for treating a host animal having a condition associated with a pathological microbial infection or a proliferative disorder includes administering to the effected host a compound described herein in a therapeutic-effective amount. An example of a therapy includes repeated administration of a therapeutic-effective amount of one or more compounds to achieve a desired therapeutic outcome, such as eliminating and/or reducing a viral load in a host to a level below that prior to the administration of the compound. Another example of a therapy may include repeated administration of sub-therapeutic-effective amounts that, over time, accumulate to a therapeutic-effective amount. In a further example, a single dose of an effective amount of one or more compounds and/or salts, esters, solvates, hydrates and prodrugs thereof to achieve a desired therapeutic outcome is envisioned.

In one embodiment, a compound may be used for treating a host animal, such as a mouse, rat, pig, cow, rabbit, dog, cat, horse, bird, lizard, fish, or primates such as a monkey, chimpanzee, or human that has a condition associated with pathological polymerase activity, such as a microbial infection and/or a proliferative disorder.

As used herein, the terms "therapeutically effective amount" or "therapeutically effective dose" (and variations thereof) mean an amount of a compound of formula I which, when administered to a host animal according to a desired dosing regimen, provides a desired therapeutic activity for therapeutic treatment and/or prophylactic treatment, such as, for example, at least partially attaining the desired effect, and/or delaying the onset of, and/or inhibiting the progression of, and/or preventing, halting or reversing altogether the onset or progression of the particular disease, disorder, and/or condition being treated. Dosing may be in a single or divided dose and may occur at intervals of minutes, hours, days, weeks, months, or years or continuously over any one of these periods, but it is recognized that once daily dosing is a desirable because of the ease of adherence to the regimen by the patient, especially when the duration of dosing is more than a few days. The half-life of the drug is an important pharmacokinetic parameter in deciding the dosing frequency. The time needed to achieve steady-state drug concentrations, as well as the time needed to establish new steady-state concentrations after a change in dosage regimen, is a function of the elimination half-life of the active therapeutic entity. For once daily dosing a plasma t1/2 of >6 hours is generally required in order to minimize Cmax/Cmin fluctuations. In the present description, it has been exemplified that compound 9 has a plasma half-life of 4-7.6 hours in preclinical animal species. Furthermore the intracellular half-life of the active anabolite of compound 9, compound 25, is 38 hours in primary human heptocytes. The long intracellular half-life of the active triphosphate anabolite, coupled with its plasma half-life, generally suggest that compound 9 can be administered, if desired, once daily for therapeutic treatment and/or prophylactic treatment of a disease in a patient, including, for example, an infection or microbial infection such as an infection of liver cells including chronic hepatitis C.

Suitable dosages lie within the range of about 0.1 ng per kg of body weight to about 10 g per kg of body weight, or in the range of about 1 µg to about 10 g per kg of body weight, or in the range of about 10 µg to about 30 µg per kg of body weight, or in the range of about 15 µg to about 25 µg per kg of body weight, or in the range of about 1 mg to about 10 g per kg of body weight, or in the range of about 1 mg to about 500 mg per kg of body weight, or in the range of about 1 mg to about 250 mg per kg of body weight, or in the range of about 1 mg to about 100 mg per kg of body weight per dosage, or up to about 50 mg per body weight per dosage, or greater or less amounts per body weight per dosage.

While not intended to limit the scope of the invention, when administered to an animal, such as a human, the composition may be administered at a dose, for example, a therapeutic-effective amount, to achieve a peak plasma of active molecule of about 0.1 nM to about 100 nM, 0.1 µM to about 100 µM, or about 0.5 µM to about 75 µM, or about 1 µM to about 50 µM, or greater than or equal to about 0.1 µM, or greater than or equal to about 0.5 µM or greater than or equal to about 1 µM, and/or intracellular concentration of about 0.1 pmol/million cells to about 100 pmol/million cells, 100 pmol/million cells to about 1000 pmol/million cells, or about 1000 pmol/million cells to about 10000 pmol/million cells, or greater than or equal to about 10 pmol/million cells, or greater than or equal to about 50 pmol/million cells or greater than or equal to about 100 pmol/million cells, and may be adjusted over time according to individual need and condition. The peak plasma and/or intracellular concentration of active molecule achieved depends on several factors familiar to those skilled in the art including, for example, route of administration, rates of absorption, protein binding, compound conversion, compound anabolism, compound catabolism, incorporation of a compound into a genome, and excretion and inactivation rates.

Suitable dosage amounts and dosing regimens may be selected in accordance with a variety of factors, including one or more particular conditions being treated, the severity of the one or more conditions, the genetic profile, age, health, sex, diet, and weight of the subject, the route of administration alone or in combination with pharmacological considerations including the activity, efficacy, bioavailability, pharmacokinetic, and toxicological profiles of the particular compound employed, whether a drug delivery system is utilised and whether the drug is administered as part of a drug combination. Therefore, the dosage regimen to be employed may vary widely and may necessarily deviate from the dosage regimens set forth herein.

In one embodiment, an active ingredient of the present disclosure may be administered in a single dose or a series of doses. While it is possible for the active ingredient to be administered alone, for example, as a fraction of a formulation scheme and/or a purified compound from a batch reaction, it may be desirable to present it as a composition, such as a pharmaceutical composition. Formulation of such compositions is well known to those skilled in the art. For example, a candidate pharmaceutical composition may contain one or more carriers, diluents, and/or excipients, and any combination thereof, whereby such carriers are inactive pharmaceutical ingredients. Examples include conventional solvents, dispersion media, fillers, solid carriers, coatings, antifungal agents, antibacterial agents, antiviral agents, dermal penetration agents, surfactants, isotonic agents, absorption agents, adjuvants, analgesics, stabilisers, preservatives, drugs, and the like. It will be understood that the compositions of the invention may also include other supplementary physiologically active agents. These carriers, diluents and excipients make up a pharmaceutical carrier system for the compound of formula I.

A candidate carrier that is to be administered to an animal is "pharmaceutically-acceptable" in the sense of being compatible with the other ingredients of the composition and suitably tolerated by the host. Compositions may be adapted according to the desired route of administration. For example, compositions herein may be formulated for oral, rectal, nasal, topical (including buccal and sublingual), transdermal, vaginal, injection/injectable, and/or parental (including subcutaneous, intramuscular, intravenous, and intradermal) administration. Other suitable administration routes are incorporated herein. The compositions may be presented conveniently in unit dosage forms and may be prepared by any methods known in the pharmaceutical arts. Examples of suitable drug formulations and/or forms are discussed in, for example, Hoover, John E. Remington's Pharmaceutical Sciences, Mack Publishing Co., Eston, Pa.; $18^{th}$ edition (1995); and Liberman, H. A. and Lachman, L. Eds., Pharmaceutical Dosage Forms, Marcel Decker, New York, N.Y., 1980. Illustrative methods include the step of bringing one or more active ingredients into association with a carrier that constitutes one or more accessory ingredients. In general, the compositions may be prepared by bringing into association uniformly and intimately one or more active ingredients with liquid carriers or finely divided solid carriers or both, and then, if necessary, shaping the product.

Compositions suitable for oral administration may be presented as discrete units such as capsules, sachets, or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary, or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (for example, inert diluent, preservative disintegrant (for example, sodium starch glycolate, cross-linked polyvinyl pyrrolidone, cross-linked sodium carboxymethyl cellulose), a surface-active, or a dispersing agent). Moulded tablets may be made by moulding in a suitable machine known to a skilled artisan a mixture of the powdered compound moistened with an inert liquid diluent. The tablets may optionally be coated and/or scored and may be formulated so as to provide slow and/or controlled release of the active ingredient therein using, for example, hydroxypropylmethyl cellulose in varying proportions to provide one or more desired release profiles. Tablets may be provided optionally with an enteric coating to provide release in parts of the gut other than the stomach.

Compositions suitable for topical administration in the mouth include lozenges including the active ingredient in a flavoured or unflavored base, usually sucrose and acacia or tragacanth gum; pastilles including the active ingredient in an inert base, such as gelatine and glycerin, and/or sucrose and acacia gum; and mouthwashes including the active ingredient in a suitable liquid carrier with or without flavouring and/or additional ingredients.

Compositions suitable for topical administration to the skin may comprise the compounds dissolved or suspended in any suitable carrier and/or base and may be in the form of lotions, gel, creams, pastes, ointments, and the like. Suitable carriers include mineral oil, propylene glycol, polyoxyethylene, polyoxypropylene, emulsifying wax, sorbitan monostearate, polysorbate 60, cetyl esters wax, cetearyl alcohol, 2-octyldodecanol, benzyl alcohol, and water. Transdermal patches may also be used to administer compositions that include one or more compounds of the invention. Compositions for rectal administration may be presented as a suppository with a suitable base including, for example, cocoa butter, glycerin, gelatine, and/or polyethylene glycol, among others. Compositions suitable for vaginal administration may be presented as pessaries, tampons, creams, gels, pastes, foams, and/or spray formulations containing compositions containing one or more active ingredient compounds of the present disclosure in addition to one or more carriers known in the art.

Compositions suitable for parenteral administration include, for example, aqueous and non-aqueous isotonic sterile injection solutions which may contain anti-oxidants, buffers, bactericides, and/or solutes that render the composition isotonic with the blood of the intended recipient; and aqueous and non-aqueous sterile suspensions which may include, for example, suspending agents and thickening agents. Parenteral compositions may be presented in unit-dose or multi-dose sealed containers, for example, ampoules and vials, and may be stored in a freeze-dried (lyophilised) condition requiring only the addition of the sterile liquid carrier, for example, water for injections, immediately prior to use.

Extemporaneous injection solutions and suspensions may be prepared from sterile powders, granules and tablets of the kind described previously. In addition, compositions and formulations may be delivered by a dry powder inhaler in the form of a dry powder or delivered by a mist inhaler in the form of a mist.

It should be understood that in addition to the active ingredients mentioned above, compositions herein may include other agents as appropriate for the type of composition in question. For example, compositions suitable for oral administration may include, for example, binders, colorants, sweeteners, thickeners, flavouring agents, disintegrating agents, coating agents, preservatives, lubricants, and/or time delay agents. Suitable sweeteners include, for example, sucrose, lactose, glucose, aspartame, and/or saccharine. Suitable disintegrating agents include, for example, cornstarch, methylcellulose, polyvinylpyrrolidone, xanthan gum, bentonite, alginic acid, and/or agar. Suitable flavouring agents include, for example, peppermint oil, oil of wintergreen, cherry, orange, or raspberry flavouring. Suitable coating agents include, for example, polymers or copolymers of acrylic acid, and/or methacrylic acid, and/or their esters, waxes, fatty alcohols, zein, shellac, or gluten. Suitable preservatives include, for example, sodium benzoate, vitamin E, alpha-tocopherol, ascorbic acid, methyl paraben, propyl paraben, or sodium bisulfite. Suitable lubricants include, for example, magnesium stearate, stearic acid, sodium oleate, sodium chloride, or talc. Suitable time delay agents include, for example, glyceryl monostearate, or glyceryl distearate.

In addition, other compounds useful in this invention that are sufficiently basic or acidic acids may also form salts. In some cases, the salts can be used as an aid in isolation, purification, resolution, or delivery of the compounds described herein. Further, compounds of the present disclosure may be administered in the form of a pharmaceutically-acceptable salt. However, non-pharmaceutically-acceptable salts also fall within the scope of the present disclosure used, for example, as intermediates in the preparation of pharmaceutically-acceptable salts or other compounds.

Suitable pharmaceutically-acceptable salts include, but are not limited to salts of pharmaceutically-acceptable inorganic acids, including, for example, hydrochloric, sulfuric, phosphoric, nitric, carbonic, boric, sulfamic, and hydrobromic acids, or salts of pharmaceutically-acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulfonic, toluenesulfonic, benezenesulfonic, salicyclic sulfanilic, aspartic, glutamic, edetic, stearic, palmitic, oleic, lauric, pantothenic, tannic, ascorbic, and valeric acids.

Base salts include, but are not limited to, those formed with pharmaceutically-acceptable cations, including alkali metal and alkaline earth metal salts, such as sodium, potassium, lithium, calcium, magnesium, ammonium, and alkylammonium. In particular, the present disclosure includes within its scope cationic salts, for example, sodium or potassium salts, or alkyl esters (for example, methyl and ethyl) of the phosphate group.

Salts of the instant compound may be a pharmaceutically suitable (i.e., pharmaceutically acceptable) salt including, but not limited to, acid addition salts formed by mixing a solution of the instant compound with a solution of a pharmaceutically acceptable acid. The pharmaceutically acceptable acid may be hydrochloric acid, methanesulphonic acid, fumaric acid, maleic acid, succinic acid, acetic acid, benzoic acid, oxalic acid, citric acid, tartaric acid, carbonic acid or phosphoric acid. Various pharmaceutically acceptable salts are well known in the art and may be used with the instant compound such as those disclosed in Berge S M et al., "Pharmaceutical Salts." J. Pharm. Sci. 66:1-19 (1977) and Haynes D A et al., "Occurrence of pharmaceutically acceptable anions and cations in the Cambridge Structural Database," J. Pharm. Sci. 94:2111-2120 (2005), which are hereby incorporated herein by reference. For example, the list of FDA-approved commercially marketed salts includes acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, mitrate, pamoate, pantothenate, phosphate, diphosphate, polygalacturonate, salicylate, stearate, subacetate, succinate, sulfate, tannate, tartrate, teoclate, and triethiodide.

In yet another embodiment, the compounds described herein, and derivatives and pharmaceutical compositions thereof, provide for the manufacture of a medicament for the treatment of a microbial infection and/or a proliferative disease or disorder, including, for example, the inhibition of polymerase activity including RNA-dependent RNA viral replication, such as HCV replication, and the treatment thereof such as RNA-dependent RNA viral infection.

Numerous variations of and chemical formulation schemes of formula I are incorporated herein. The following definitions and examples are intended to help describe some potential embodiments.

"Alkyl", alone or in combination, refers to monovalent alkyl groups which may be straight chained or branched and preferably have from 1 to 10 carbon atoms or more preferably 1 to 6 carbon atoms. Examples of such alkyl groups include methyl, ethyl, n-propyl, iso-propyl, n-butyl, iso-butyl, n-hexyl, and the like.

"Alkylene", alone or in combination, refers to a divalent alkyl group wherein the alkyl group is as described above.

"Aryl", alone or in combination, refers to an unsaturated aromatic carbocyclic group having a single ring (e.g., phenyl) or multiple condensed rings (e.g., naphthyl or anthryl), preferably having from 6 to 14 carbon atoms. Examples of aryl groups include phenyl, naphthyl, and the like.

"Arylene", alone or in combination, refers to a divalent aryl group wherein the aryl group is as described above.

"Aryloxy", alone or in combination, refers to the group aryl-O— wherein the aryl group is as described above.

"Arylalkyl", alone or in combination, refers to -alkylene-aryl groups preferably having from 1 to 10 carbon atoms in the alkylene moiety and from 6 to 10 carbon atoms in the aryl moiety. Such arylalkyl groups are exemplified by benzyl, phenethyl, and the like.

"Arylalkoxy", alone or in combination, refers to the group arylalkyl-O—, wherein the arylalkyl group is as described above. Such arylalkoxy groups are exemplified by benzyloxy and the like.

"Alkoxy", alone or in combination, refers to the group alkyl-O— where the alkyl group is as described above. Examples include, methoxy, ethoxy, n-propoxy, iso-propoxy, n-butoxy, tert-butoxy, sec-butoxy, n-pentoxy, n-hexoxy, 1,2-dimethylbutoxy, and the like.

"Alkenyl", alone or in combination, refers to a monovalent alkenyl group which may be straight chained or branched and preferably have from 2 to 10 carbon atoms and more preferably 2 to 6 carbon atoms and have at least 1 and preferably from 1-2, carbon to carbon, double bonds. Examples include ethenyl (—CH=CH$_2$), n-propenyl (—CH$_2$CH=CH$_2$), iso-propenyl (—C(CH$_3$)=CH$_2$), but-2-enyl (—CH$_2$CH=CHCH$_3$), and the like.

"Alkenyloxy", alone or in combination, refers to the group alkenyl-O— where the alkenyl group is as described above.

"Alkynyl", alone or in combination, refers to alkynyl groups preferably having from 2 to 10 carbon atoms and more preferably 2 to 6 carbon atoms and having at least 1, and preferably from 1-2, carbon to carbon, triple bonds. Examples of alkynyl groups include ethynyl (—C≡CH), propargyl (—CH$_2$C≡CH), pent-2-ynyl (—CH$_2$C≡CCH$_2$—CH$_3$), and the like.

"Alkynyloxy", alone or in combination, refers to the group alkynyl-O— where the alkynyl group is as described above.

"Acyl", alone or in combination, refers to groups H—C(O)—, alkyl-C(O)—, cycloalkyl-C(O)—, aryl-C(O)—, heteroaryl-C(O)— and heterocyclyl-C(O)—, where alkyl, cycloalkyl, aryl, heteroaryl, and heterocyclyl are as described herein.

"Oxyacyl", alone or in combination, refers to groups H—OC(O)—, alkyl-OC(O)—, cycloalkyl-OC(O)—, aryl-OC(O)—, heteroaryl-OC(O)—, and heterocyclyl-OC(O)—, where alkyl, cycloalkyl, aryl, heteroaryl, and heterocyclyl are as described herein.

"Amino", alone or in combination, refers to the group —NR""R"" where each R"" is independently hydrogen, alkyl, cycloalkyl, aryl, heteroaryl, and heterocyclyl and where alkyl, cycloalkyl, aryl, heteroaryl, and heterocyclyl are as described herein.

"Aminoacyl", alone or in combination, refers to the group —C(O)NR"" R"" where each R"" is independently hydrogen, alkyl, cycloalkyl, aryl, heteroaryl, and heterocyclyl and where alkyl, cycloalkyl, aryl, heteroaryl, and heterocyclyl are as described herein.

"Acylamino", alone or in combination, refers to the group —NR"" C(O)R"" where each R"" is independently hydrogen, alkyl, cycloalkyl, aryl, heteroaryl, and heterocyclyl, and where alkyl, cycloalkyl, aryl, heteroaryl, and heterocyclyl are as described herein.

"Acyloxy", alone or in combination, refers to the groups —OC(O)—H, —OC(O)-alkyl, —OC(O)-aryl, —C(O)O-heteroaryl, and —C(O)O-heterocyclyl where alkyl, aryl, heteroaryl, and heterocyclyl are as described herein.

"Aminoacyloxy", alone or in combination, refers to the groups —OC(O)NR""-H, —OC(O)NR""-alkyl, —OC(O)NR""-aryl, —OC(O)NR""-heteroaryl, and —OC(O)NR""-heterocyclyl where R"" is independently hydrogen, alkyl, cycloalkyl, aryl, heteroaryl, and heterocyclyl, and where alkyl, cycloalkyl, aryl, heteroaryl, and heterocyclyl are as described herein.

"Oxyacylamino", alone or in combination, refers to the groups —NR""C(O)OH, —NR""C(O)O-alkyl, —NR""(O)O-aryl, —NR""C(O)O-heteroaryl, and NR""C(O)O-heterocyclyl where R"" is independently hydrogen, alkyl, cycloalkyl, aryl, heteroaryl, and heterocyclyl, and where alkyl, cycloalkyl, aryl, heteroaryl and heterocyclyl is as described herein.

"Oxyacyloxy", alone or in combination, refers to the groups —OC(O)—OH, —OC(O)O-alkyl, —O—C(O)O-aryl, —OC(O)O-heteroaryl, and —OC(O)O-heterocyclyl, and where alkyl, cycloalkyl, aryl, heteroaryl, and heterocyclyl are as described herein.

"Acylimino", alone or in combination, refers to the groups —C(NR"")—R"" where each R"" is independently hydrogen, alkyl, cycloalkyl, aryl, heteroaryl, and heterocyclyl, and where alkyl, cycloalkyl, aryl, heteroaryl, and heterocyclyl are as described herein.

"Acyliminoxy", alone or in combination, refers to the groups —O—C(NR'''')—R'''' where each R'''' is independently hydrogen, alkyl, cycloalkyl, aryl, heteroaryl, and heterocyclyl, and where alkyl, cycloalkyl, aryl, heteroaryl, and heterocyclyl are as described herein.

"Oxyacylimino", alone or in combination, refers to the groups —C(NR'''')—OR'''' where each R'''' is independently hydrogen, alkyl, cycloalkyl, aryl, heteroaryl, and heterocyclyl, and where alkyl, cycloalkyl, aryl, heteroaryl, and heterocyclyl are as described herein.

"Cycloalkyl", alone or in combination, refers to cyclic alkyl groups having a single cyclic ring or multiple condensed rings, preferably incorporating 3 to 8 carbon atoms. Such cycloalkyl groups include, by way of example, single ring structures such as cyclopropyl, cyclobutyl, cyclopentyl, cyclohexyl, cyclooctyl, and the like, or multiple ring structures such as adamantanyl, and the like.

"Cycloalkenyl", alone or in combination, refers to cyclic alkenyl groups having a single cyclic ring and at least one point of internal unsaturation, preferably incorporating 4 to 8 carbon atoms. Examples of suitable cycloalkenyl groups include, for instance, cyclobut-2-enyl, cyclopent-3-enyl, cyclohex-4-enyl, cyclooct-3-enyl, and the like.

"Halo" or "halogen", alone or in combination, refers to fluoro, chloro, bromo, and iodo.

"Heteroaryl", alone or in combination, refers to a monovalent aromatic heterocyclic group which fulfils the Hückel criteria for aromaticity (i.e., contains 4 n+2 π electrons, is planar and conjugated) and preferably has from 2 to 10 carbon atoms and 1 to 4 heteroatoms selected from oxygen, nitrogen, selenium, and sulfur within the ring (and includes oxides of sulfur, selenium, and nitrogen). Such heteroaryl groups can have a single ring (e.g., pyridyl, pyrrolyl, or N-oxides thereof, or furyl) or multiple condensed rings (e.g., indolizinyl, benzoimidazolyl, coumarinyl, quinolinyl, isoquinolinyl, or benzothienyl).

"Heterocyclyl", alone or in combination, refers to a monovalent saturated or unsaturated group having a single ring or multiple condensed rings, preferably from 1 to 8 carbon atoms and from 1 to 4 heteroatoms selected from nitrogen, sulfur, oxygen, selenium, and phosphorous within the ring. A more preferred heteroatom is nitrogen.

Examples of heterocyclyl and heteroaryl groups include, but are not limited to, oxazole, pyrrole, imidazole, imidazoline, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiadiazoles, oxadiazole, oxatriazole, tetrazole, thiazolidine, thiophene, benzo[b]thiophene, morpholino, piperidinyl, pyrrolidine, tetrahydrofuranyl, triazole, benzo[1,3]dioxole, and the like. Heterocyclyl rings can optionally also be fused to aryl rings, such that the definition includes bicyclic structures. Typically such fused heterocyclyl groups share one bond with an optionally substituted benzene ring. Examples of benzo-fused heterocyclyl groups include, but are not limited to, benzo[1,3]dioxole, benzimidazolidinone, tetrahydroquinoline, and methylenedioxybenzene ring structures. Binding to the heterocycle can be at the position of an heteroatom or via a carbon atom of the heterocycle, or, for benzo-fused derivatives, via an heteroatom and a carbon atom or of the benzene ring.

"Thio", alone or in combination, refers to groups H—S—, alkyl-S—, cycloalkyl-S—, aryl-S—, heteroaryl-S—, and heterocyclyl-S—, where alkyl, cycloalkyl, aryl, heteroaryl, and heterocyclyl are as described herein.

"Thioalkyl", alone or in combination, refers to —S-alkyl, where alkyl is a described herein.

"Thioacyl", alone or in combination, refers to groups H—C(S)—, alkyl-C(S)—, cycloalkyl-C(S)—, aryl-C(S)—, heteroaryl-C(S)—, and heterocyclyl-C(S)—, where alkyl, cycloalkyl, aryl, heteroaryl, and heterocyclyl are as described herein.

"Oxythioacyl", alone or in combination, refers to groups HO—C(S)—, alkylO-C(S)—, cycloalkylO-C(S)—, arylO-C(S)—, heteroarylO-C(S)—, and heterocyclylO-C(S)—, where alkyl, cycloalkyl, aryl, heteroaryl, and heterocyclyl are as described herein.

"Oxythioacyloxy", alone or in combination, refers to groups HO—C(S)—O—, alkylO-C(S)—O—, cycloalkylO-C(S)—O—, arylO-C(S)—O—, heteroarylO-C(S)—O—, and heterocyclylO-C(S)—O—, where alkyl, cycloalkyl, aryl, heteroaryl, and heterocyclyl are as described herein.

"Phosphorylamino", alone or in combination, refers to the groups —NR''''-P(O)(R'''')(OR'''') where R'''' represents H, alkyl, cycloalkyl, alkenyl, or aryl, R'''' represents OR'''' or is hydroxy or amino, and R'''' is alkyl, cycloalkyl, aryl, or arylalkyl, where alkyl, amino, alkenyl, aryl, cycloalkyl, and arylalkyl are as described herein.

"Thioacyloxy", alone or in combination, refers to groups H—C(S)—O—, alkyl-C(S)—O—, cycloalkyl-C(S)—O—, aryl-C(S)—O—, heteroaryl-C(S)—O—, and heterocyclyl-C(S)—O—, where alkyl, cycloalkyl, aryl, heteroaryl, and heterocyclyl are as described herein.

"Sulfinyl", alone or in combination, refers to groups H—S(O)—, alkyl-S(O)—, cycloalkyl-S(O)—, aryl-S(O)—, heteroaryl-S(O)—, and heterocyclyl-S(O)—, where alkyl, cycloalkyl, aryl, heteroaryl, and heterocyclyl are as described herein.

"Sulfonyl", alone or in combination, refers to groups H—S(O)$_2$—, alkyl-S(O)$_2$—, cycloalkyl-S(O)$_2$—, aryl-S(O)$_2$—, heteroaryl-S(O)$_2$—, and heterocyclyl-S(O)$_2$—, where alkyl, cycloalkyl, aryl, heteroaryl, and heterocyclyl are as described herein.

"Sulfinylamino", alone or in combination, refers to groups H—S(O)—NR''''-, alkyl-S(O)—NR''''-, cycloalkyl-S(O)—NR''''-, aryl-S(O)—NR''''-, heteroaryl-S(O)—NR''''-, and heterocyclyl-S(O)—NR''''-, where R'''' is independently hydrogen, alkyl, cycloalkyl, aryl, heteroaryl, and heterocyclyl, and where alkyl, cycloalkyl, aryl, heteroaryl, and heterocyclyl are as described herein.

"Sulfonylamino", alone or in combination, refers to groups H—S(O)$_2$—NR''''-, alkyl-S(O)$_2$—NR''''-, cycloalkyl-S(O)$_2$—NR''''-, aryl-S(O)$_2$—NR''''-, heteroaryl-S(O)$_2$—NR''''-, and heterocyclyl-S(O)$_2$—NR''''-, where R'''' is independently hydrogen, alkyl, cycloalkyl, aryl, heteroaryl, and heterocyclyl, and where alkyl, cycloalkyl, aryl, heteroaryl, and heterocyclyl are as described herein.

"Oxysulfinylamino", alone or in combination, refers to groups HO—S(O)—NR''''-, alkylO-S(O)—NR''''-, cycloalkylO-S(O)—NR''''-, arylO-S(O)—NR''''-, heteroarylO-S(O)—NR''''-, and heterocyclylO-S(O)—NR''''-, where R'''' is independently hydrogen, alkyl, cycloalkyl, aryl, heteroaryl, and heterocyclyl, and where alkyl, cycloalkyl, aryl, heteroaryl and heterocyclyl are as described herein.

"Oxysulfonylamino", alone or in combination, refers to groups HO—S(O)$_2$—NR''''-, alkylO-S(O)$_2$—NR''''-, cycloalkylO-S(O)$_2$—NR''''-, arylO-S(O)$_2$—NR''''-, heteroarylO-S(O)$_2$—NR''''-, and heterocyclylO-S(O)$_2$—

NR''''-, where R'''' is independently hydrogen, alkyl, cycloalkyl, aryl, heteroaryl, and heterocyclyl, and where alkyl, cycloalkyl, aryl, heteroaryl and heterocyclyl are as described herein.

"Aminothioacyl", alone or in combination, refers to groups R''''R''''N—C(S)—, where each R'''' is independently hydrogen, alkyl, cycloalkyl, aryl, heteroaryl, where alkyl, cycloalkyl, aryl, heteroaryl and heterocyclyl are as described herein.

"Thioacylamino", alone or in combination, refers to groups H—C(S)—NR''''-, alkyl-C(S)NR''''-, cycloalkyl-C(S)—NR''''-, heteroaryl-C(S)—NR''''-, and heterocyclyl-C(S)—NR''''-, where R'''' is independently hydrogen, alkyl, cycloalkyl, aryl, heteroaryl, and where alkyl, cycloalkyl, aryl, heteroaryl and heterocyclyl are as described herein.

"Aminosulfinyl", alone or in combination, refers to groups R''''R''''N—S(O)—, where each R'''' is independently hydrogen, alkyl, cycloalkyl, aryl, heteroaryl, and heterocyclic, and where alkyl, cycloalkyl, aryl, heteroaryl and heterocyclyl are as described herein.

"Aminosulfonyl", alone or in combination, refers to groups R''''R''''N—S(O)$_2$—, where each R'''' is independently hydrogen, alkyl, cycloalkyl, aryl, heteroaryl, and heterocyclic, and where alkyl, cycloalkyl, aryl, heteroaryl and heterocyclyl are as described herein.

The term "substituted" (and variations thereof) means that a is substituted or fused (for example, so as to form a condensed polycyclic group) with one or more groups such as hydroxyl, acyl, alkyl, alkoxy, alkenyl, alkenyloxy, alkynyl, alkynyloxy, amino, aminoacyl, thio, arylalkyl, arylalkoxy, aryl, aryloxy, acylamino, cyano, halogen, nitro, sulfo, phosphono, phosphorylamino, phosphinyl, heteroaryl, heteroaryloxy, heterocyclyl, heterocycloxy, oxyacyl, acyloxy, oxime, oxime ether, hydrazone, oxyacylamino, aminoacyloxy, trihalomethyl, trialkylsilyl, pentafluoroethyl, trifluoromethoxy, difluoromethoxy, trifluoromethanethio, trifluoroethenyl, mono- or di-alkylamino, mono- or di-(substituted alkyl)amino, mono- or di-arylamino, mono- or di-heteroarylamino, mono- or di-heterocyclyl amino, unsymmetric di-substituted amines having different substituents selected from alkyl, aryl, heteroaryl, or heterocyclyl, and other like substitutions. The term "substituted amino" group includes amino acid and peptide residues. "Substituted phenyl" group includes, for example, 1,3-benzodioxole, 4-methoxyphenyl, 4-azacyclohexyl, 2-aminophenyl, 4-fluorophenyl, 2-fluorophenyl, 3-acetylphenyl, and methylbenzyl.

The term "base", unless otherwise specified, refers to the base moiety of a nucleoside or nucleotide. The base moiety is the nitrogen-heterocycle portion of a nucleoside or nucleotide. The base moiety of a nucleotide of formula I is a heterocycle represented by formula (II) and designated "Base." The nucleoside base is attached to the sugar moiety of a nucleoside in such ways that both α and β anomers of D or L nucleosides can be produced. This is denoted by use of the ⁓bond, which links the base to the sugar moiety.

The term "sugar" refers to the furanose portion of a nucleoside or nucleotide. The sugar moiety of formula I nucleosides, nucleotides, and nucleotides mimics and/or prodrugs thereof may contain one or more substituents at their C1-, C2-, C3- and C4-positions of the furanose. Substituents may be directed to either the α- or β-face of the furanose. The nucleoside or nucleotide base can be considered as a substituent at the C-1 position of the furanose and is preferably directed to the β-face of the sugar. The β-face is the side of a furanose on which a purine or pyrimidine base of natural β-D-nucleosides, for example, is present. The α-face is the side of the sugar opposite to the β-face.

The terms "protecting group" (and variations thereof) refer to a moiety or substituent that alters or masks a property or reactivity of another moiety, such as, for example, altering the polarity, lipophilicity or hydrophobicity of a functional group. Examples of protecting groups and the chemical structure are extensive and vary widely. Examples of a "protecting group" for O, S, N, hydroxyl or NH$_2$, include moieties such as acyl groups, silyl groups, and the like. A protecting group may also serve as an intermediate in the synthesis of a desired compound to assist, for example, in the efficiency of a desired reaction by facilitating the making and/or breaking of chemical bonds in a synthetic pathway. A protecting group may also improve or enhance drug absorption, solubility, lipophilicity, bioavailability, efficacy, and/or drug delivery into cells and may also be referred to as a prodrug. In such a case, the protecting group converts a therapeutically-active compound into a prodrug as described herein. In any event, a compound containing a protecting group may be biologically active or inactive. Other suitable protecting groups for these and other moieties are described by T. W. Greene and P. G. M. Wuts; *Protecting Groups in Organic Synthesis*, 3$^{rd}$ Ed, John Wiley & Sons, Inc. (1999).

As used herein, "hydrates" of the instant compound may be a pharmaceutically suitable (i.e., pharmaceutically acceptable) hydrate that is a compound formed by the addition of water or its elements to a host molecule (e.g., the free form version of the compound) including, but not limited to, monohydrates, dihydrates, etc.

As used herein, "solvates" of the instant compound may be a pharmaceutically suitable (i.e., pharmaceutically acceptable) solvate, whereby solvation is an interaction of a solute with the solvent which leads to stabilization of the solute species in the solution, and whereby the solvated state is an ion in a solution complexed by solvent molecules. Solvates and hydrates may also be referred to as "analogues."

The present disclosure relates to, in particular, nucleoside and nucleotide analogue compounds that may function as antiproliferative agents, for example, via polymerase inhibition, and more particularly to bicyclic nucleosides and nucleotides for the treatment of diseases such as proliferative and infectious diseases, compositions of those compounds, intermediates for the synthesis of those compounds, processes for the preparation of those compounds, and processes for treating a condition associated with the disease.

A compound of formula I corresponds in structure to formula I:

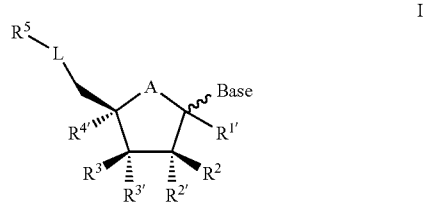

wherein the ⁓ defines the active pharmaceutical ingredient as a D- or L-nucleoside or nucleotide; A is selected from the group consisting of —O—, —S—, —CH$_2$—, —CHF—, —CF$_2$—, and —NR—; R$^{1'}$, R$^2$, R$^{2'}$, R$^3$, R$^{3'}$, and R$^{4'}$ are independently selected from the group consisting of —H, halogen, —OH, —NHOH, —NHNH$_2$, —N$_3$, —CN, —OCOCHNC(CH$_3$)$_2$, —COOH, —CONH$_2$, —C(S)NH$_2$, —COOR, —R, —OR, —SR, —SSR, —NHR, and —NR$_2$, or R$^2$ and R$^{2'}$ together or R$^3$ and R$^{3'}$ together represents =O, =S, or =L'—Y', where L' is selected from the group consisting of N, CH, CF, CCl, and CBr and Y' is selected from the group consisting of H, halogen, $N_3$, methyl, ethyl, and CN; R is independently halogen, —H, —OH, —SH, —CN, $S(C_1$-$C_4$alkyl), —$NO_2$, $NH_2$, —$NHNH_2$, —$N_3$, —NR'R' wherein each R' is independently H or $C_1$-$C_4$ alkyl, —C(S)$NH_2$, —$CH_3$, —$CH_2OH$, —$CH_2NH_2$, —$CH_2NH_3^+$, —COOH, —$COOCH_3$, —$COOCH_2CH_3$, —$CONHCH_3$, —$CONH_2$, —$CF_3$, —$N(CH_3)_2$, —$NHCOCH_3$, —$NHCONH_2$, —NHC-$NHNH_2$, —$ONH_2$, —$CH_2OCH_3$, —$O(CH_2)CH_3$, $COOC_1$-$C_4$alkyl, optionally substituted alkyl, optionally substituted alkenyl, optionally substituted alkynyl, optionally substituted aryl, optionally substituted acyl, optionally substituted arylalkyl, optionally substituted cycloalkyl, optionally substituted cycloalkenyl, optionally substituted phenyl, optionally substituted heteroaryl, optionally substituted heterocyclyl, optionally substituted alkyloxy, optionally substituted alkenyloxy, optionally substituted alkynoxy, optionally substituted aryloxy, optionally substituted acyloxy, optionally substituted oxyacyl, optionally substituted arylalkoxy, optionally substituted heterocycloxy, optionally substituted heteroaryloxy, optionally substituted cycloalkoxy, optionally substituted cycloalkenoxy, optionally substituted amino, optionally substituted aminoacyl, optionally substituted aminoacyloxy, optionally substituted acylamino, optionally substituted oxyacylamino, optionally substituted oxyacyloxy, optionally substituted acylimino, optionally substituted acyliminoxy, optionally substituted oxyacylimino, optionally substituted aminothioacyl, optionally substituted thioacylamino, optionally substituted aminosulfinyl, optionally substituted aminosulfonyl, optionally substituted thio, optionally substituted thioalkyl, optionally substituted thioacyl, optionally substituted thioacyloxy, optionally substituted oxythioacyl, optionally substituted oxythioacyloxy, optionally substituted phosphorylamino, optionally substituted sulfinyl, optionally substituted sulfonyl, optionally substituted sulfinylamino, optionally substituted sulfonylamino, optionally substituted oxysulfinylamino, and optionally substituted oxysulfonylamino; L is selected from the group consisting —O, —S, —NH, —NR, —$CY_3$, —$CY_2O$, —$CY_2S$, —$CY_2NH$, —$CY_2$, —$CY_2CY_2$, —$CY_2OCY_2$, —$CY_2SCY_2$, and —$CY_2NHCY_2$; Y is independently selected from the group consisting of —H, halogen, —R, —OR, and —$NR_2$; $R^5$ is selected from the group consisting of —OH, —R, —OR, —$NR_2$, or a mono-phosphate, di-phosphate, or tri-phosphate moiety or mimic thereof; Base is a group of formula II:

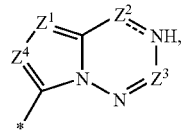

II wherein the dashed line "-----"is a single or double bond; $Z^1$, $Z^3$, and $Z^4$ are independently selected from the group consisting of >C—CONHR >C—$CONR_2$, >C—C(S)$NH_2$, >C—COOR, >C—R, >C—OR, >C—SR, >C—NHR, >C—$NR_2$, >C-optionally substituted heteroaryl, >C-optionally substituted alkyl, and >C-G; $Z^2$ is selected from the group consisting of >C—$NH_2$ and >C=O; G is independently selected from the group consisting of —H, —F, —Cl, —I, —$NH_2$, —$NHCH_3$, —CN, —COOH, —$CSNH_2$, —C≡CH, —C≡$CCH_3$, —C≡$CCH_2OH$, —C≡C—$Si(CH_3)_3$, —$CONH_2$, —$CONHCH_3$, —CONH-phenyl, —CONH-methylphenyl, thiazole, oxazole, imidazole, imidazoline, triazole, and tetrazole, or a pharmaceutically-acceptable salt, ester, solvate, hydrate, or prodrug thereof.

In one exemplary embodiment, when a compound of formula I comprises two or more G groups, the G's are identical or different.

In another exemplary embodiment, when A is O; $R^{1''}$, $R^3$, $R^{4'}$, and $R^5$ are H; L is O; and $R^{2'}$ and $R^{3'}$ are OH; then $R^2$ is halogen, OH, NHOH, $NHNH_2$, $N_3$, CN, OCOCHNC$(CH_3)_2$, COOH, $CONH_2$, C(S)$NH_2$, COOR, $R^6$, OR, SR, SSR, NHR, or $NR_2$, and $R^6$ is halogen, OH, SH, CN, $S(C_{1-4}$ alkyl), $NO_2$, $NH_2$, $NHNH_2$, $N_3$, NR'R' wherein each R' is independently H or $C_{1-4}$ alkyl, C(S)$NH_2$, $CH_3$, $CH_2OH$, $CH_2NH_2$, $CH_2NH_3^+$, COOH, $COOCH_3$, $COOCH_2CH_3$, $CONHCH_3$, $CONH_2$, $CF_3$, $N(CH_3)_2$, $NHCOCH_3$, $NHCONH_2$, $NHCNHNH_2$, $ONH_2$, $CH_2OCH_3$, $O(CH_2)CH_3$, COO($C_{1-4}$ alkyl), substituted alkyl, substituted alkenyl, substituted alkynyl, substituted aryl, substituted acyl, substituted arylalkyl, substituted cycloalkyl, substituted cycloalkenyl, substituted phenyl, substituted heteroaryl, substituted heterocyclyl, substituted alkyloxy, substituted alkenyloxy, substituted alkynoxy, substituted aryloxy, substituted acyloxy, substituted oxyacyl, substituted arylalkoxy, substituted heterocycloxy, substituted heteroaryloxy, substituted cycloalkoxy, substituted cycloalkenoxy, substituted amino, substituted aminoacyl, substituted aminoacyloxy, substituted acylamino, substituted oxyacylamino, substituted oxyacyloxy, substituted acylimino, substituted acyliminoxy, substituted oxyacylimino, substituted aminothioacyl, substituted thioacylamino, substituted aminosulfinyl, substituted aminosulfonyl, substituted thio, substituted thioalkyl, substituted thioacyl, substituted thioacyloxy, substituted oxythioacyl, substituted oxythioacyloxy, substituted phosphorylamino, substituted sulfinyl, substituted sulfonyl, substituted sulfinylamino, substituted sulfonylamino, substituted oxysulfinylamino, or, substituted oxysulfonylamino.

In one embodiment of a compound of formula I, -----is a double bond, $Z^1$ is >C—R'', $Z^2$ is >C—$NH_2$, $Z^3$ is >C—R''', $Z^4$ is >C—R'''', and R'', R''' and R'''' are each independently H, F, I, Cl, $NH_2$, $NHCH_3$, C(=O)$NH_2$, C(=O)$NHCH_3$, C(=O)NH($C_6H_5$), C(=O)NH($C_6H_5CH_2$), CN, C≡CH, C≡$CCH_3$, C≡$CCH_2OH$, C≡C—$Si(CH_3)_3$, C(=S)$NH_2$, $CO_2H$,

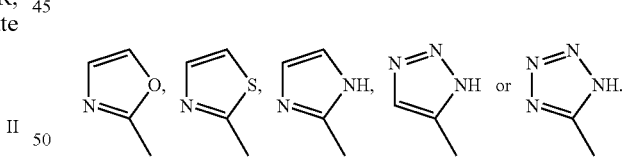

In another embodiment of a compound of formula I, -----is a single bond, $Z^1$ is >C—R'', $Z^2$ is >C=O, $Z^3$ is >C—R''', $Z^4$ is >C—R'''', and R'', R''' and R'''' are each independently H, F, I, Cl, $NH_2$, $NHCH_3$, C(=O)$NH_2$, C(=O)$NHCH_3$, C(=O)NH($C_6H_5$), —C(=O)NH($CH_2C_6H_5$), CN, C≡CH, C≡$CCH_3$, C≡$CCH_2OH$, C≡C—$Si(CH_3)_3$, C(=S)$NH_2$, $CO_2H$,

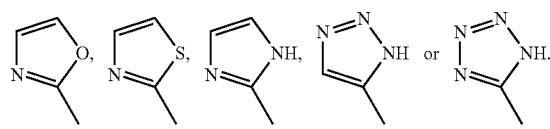

In yet another embodiment of a compound of formula I, $Z^4$ is >C—H.

In still another embodiment of a compound of formula I, $Z^4$ is >C—R"", and R"" is F, I, Cl, $NH_2$, $NHCH_3$, $C(=O)NH_2$, $C(=O)NHCH_3$, $C(=O)NHC_6H_5$, $C(=O)NH(CH_2C_6H_5)$, CN, C≡CH, C≡CCH$_3$, C≡CCH$_2$OH, C≡C—Si(CH$_3$)$_3$, $C(=S)NH_2$, $CO_2H$,

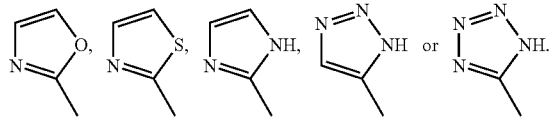

In another embodiment of a compound of formula I, $Z^4$ is >C—R"" and R"" is F, I or Cl.

In another embodiment of a compound of formula I, $Z^3$ is >C—R''', and R''' is H.

In another embodiment of a compound of formula I, $Z^3$ is >C—R''', and R''' is $NH_2$.

In another embodiment of a compound of formula I, $Z^1$ is >C—H.

In another embodiment of a compound of formula I, $Z^1$ is >C—R'', and R'' is independently F, I, Cl, $NH_2$, $NHCH_3$, $C(=O)NH_2$, $C(=O)NHCH_3$, $C(=O)NHC_6H_5$, $C(=O)NHCH_2C_6H_5$, CN, C≡CH, C≡CCH$_3$, C≡CCH$_2$OH, C≡C—Si(CH$_3$)$_3$, $C(=S)NH_2$, $CO_2H$,

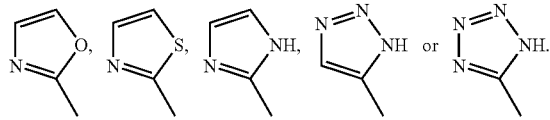

In another embodiment of a compound of formula I, A is oxygen.

In another embodiment of a compound of formula I, L is O, and $R^5$ is H or the mono-, di- or tri-phosphate moiety or mimic thereof.

In another embodiment, a compound of formula I is selected from 4-amino-5-fluoro-7-(2-C-methyl-β-D-ribofuranosyl)-pyrrolo[2,1-f][1,2,4]triazine; 4-amino-5-chloro-7-(2-C-methyl-β-D-ribofuranosyl)-pyrrolo[2,1-f][1,2,4]triazine; 4-Amino-5-iodo-(2-C-methyl-β-D-ribofuranosyl)-pyrrolo[2,1-f][1,2,4]triazine; 4-amino-7-(2-C-methyl-β-D-ribofuranosyl)-pyrrolo[2,1-f][1,2,4]triazine-5-carbonitrile; 4-amino-7-(2-C-methyl-β-D-ribofuranosyl)-pyrrolo[2,1-f][1,2,4]triazine-5-carboxylic acid amide; 4-amino-5-trimethylsilanylethynyl-7-(2-C-methyl-β-D-ribofuranosyl)-pyrrolo[2,1-f][1,2,4]triazine; 4-amino-5-ethynyl-7-(2-C-methyl-β-D-ribofuranosyl)-pyrrolo[2,1-f][1,2,4]triazine; 4-amino-7-(2-C-methyl-β-D-ribofuranosyl)-pyrrolo[2,1-f][1,2,4]triazine-5-carboxylic acid; 2,4-diamino-7-(2-C-methyl-β-D-ribofuranosyl)-pyrrolo[2,1-f][1,2,4]triazine; 4-amino-7-(2-C-methyl-β-D-ribofuranosyl)-pyrrolo[2,1-f][1,2,4]triazine-5-carbothioic acid amide; 4-amino-5-oxazol-2-yl-7-(2-C-methyl-β-D-ribofuranosyl)-pyrrolo[2,1-f][1,2,4]triazine; 4-amino-5-thiazol-2-yl-7-(2-C-methyl-β-D-ribofuranosyl)-pyrrolo[2,1-f][1,2,4]triazine; 4-amino-5-(3H-[1,2,3]triazol-4-yl)-7-(2-C-methyl-β-D-ribofuranosyl)-pyrrolo[2,1-f][1,2,4]triazine; 4-Amino-6-fluoro-7-(2-C-methyl-β-D-ribofuranosyl)-pyrrolo[2,1-f][1,2,4]triazin-7-yl; 4-amino-5-imidazole-7-(2-C-methyl-β-D-ribofuranosyl)-pyrrolo[2,1-f][1,2,4]triazine; and 4-amino-5-imidazoline-7-(2-C-methyl-β-D-ribofuranosyl)-pyrrolo[2,1-f][1,2,4]triazine.

In another embodiment, a compound of formula I is 4-amino-7-(2-C-methyl-β-D-ribofuranosyl)-pyrrolo[2,1-f][1,2,4]triazine.

In another embodiment of a compound of formula I, $R^5$ is a phosphoramidate or a phosphoester of the mono-, di- or tri-phosphate moiety.

In yet another embodiment, Se may be substituted for S independently at every position where S is an option. A compound of the present disclosure also includes a pharmaceutically-acceptable salt, ester, solvate, hydrate and/or a prodrug thereof.

In one embodiment, the sugar moiety may be represented by the following:

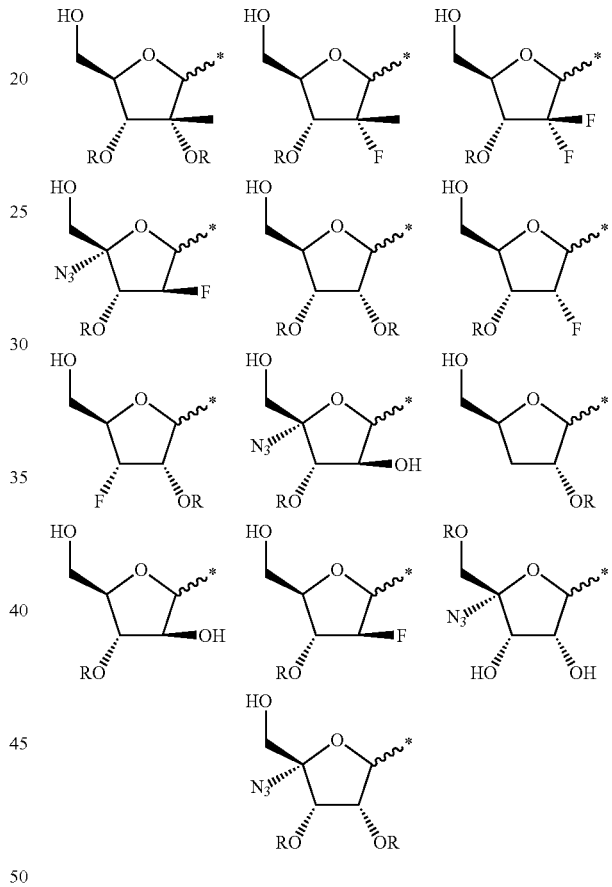

and C-5 mono-phosphate, di-phosphate, and tri-phosphate derivatives thereof, or C-5 mono-phosphate, di-phosphate, and tri-phosphate mimic derivatives thereof, and prodrug moieties thereof such as phosphoesters and phosphoamidates.

In a further embodiment, the sugar moiety may be represented by the following formulae:

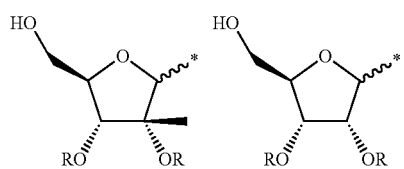

-continued

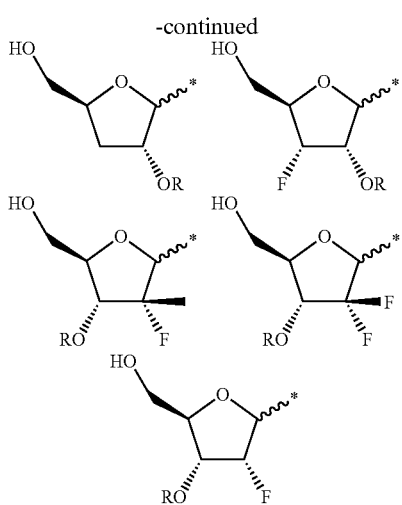

and C-5 mono-phosphate, di-phosphate, and tri-phosphate derivatives thereof, or C-5 mono-phosphate, di-phosphate, and tri-phosphate mimic derivatives thereof.

In yet a further embodiment, the sugar moiety may be represented by the following formulae:

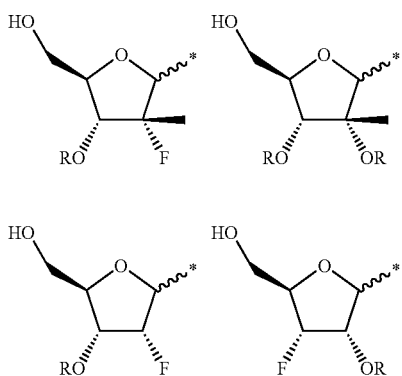

and C-5 mono-phosphate, di-phosphate, and tri-phosphate derivatives thereof, or C-5 mono-phosphate, di-phosphate, and tri-phosphate mimic derivatives thereof.

In a further embodiment, the sugar moiety may be represented by the following formulae:

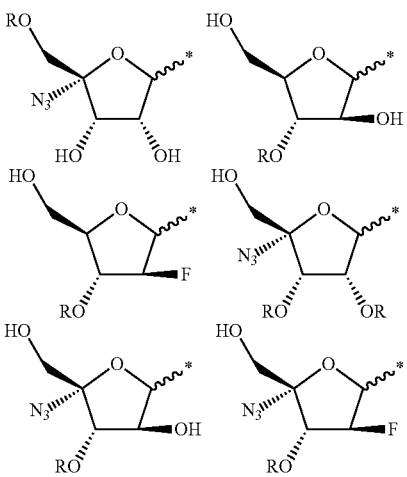

and C-5 mono-phosphate, di-phosphate, and tri-phosphate derivatives thereof, or C-5 mono-phosphate, di-phosphate, and tri-phosphate mimic derivatives thereof.

In yet a further embodiment, the sugar moiety may be represented by the following formulae:

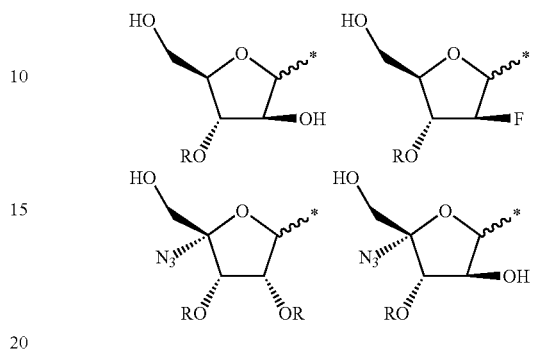

and C-5 mono-phosphate, di-phosphate, and tri-phosphate derivatives thereof, or C-5 mono-phosphate, di-phosphate, and tri-phosphate mimic derivatives thereof.

Accordingly, one embodiment of the compound of formula I may be represented by the following formulae, or salts, esters, solvates, hydrates or prodrugs thereof:

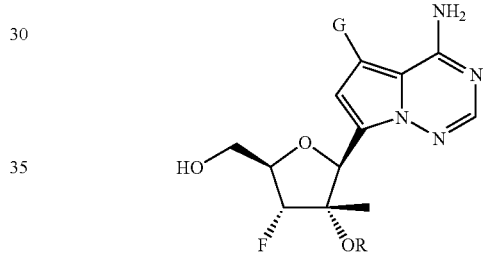

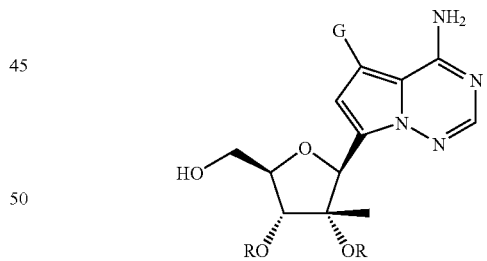

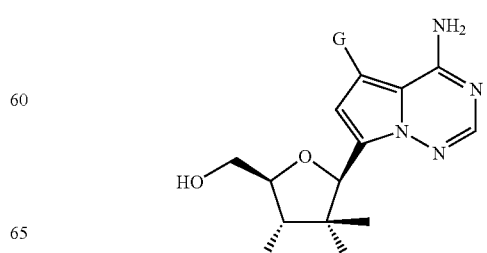

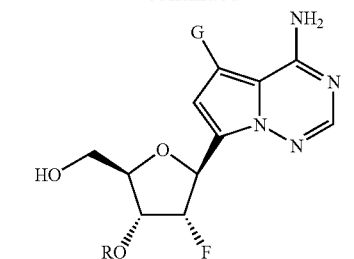
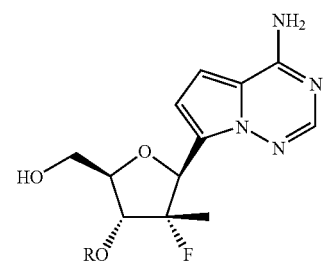
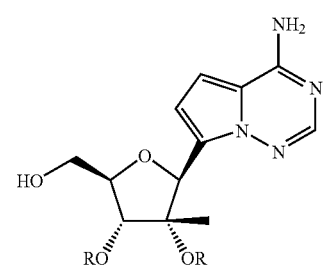
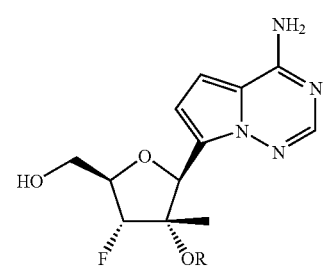
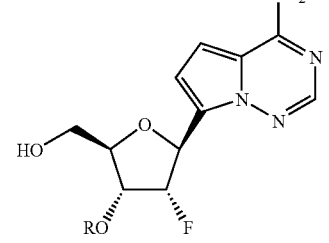
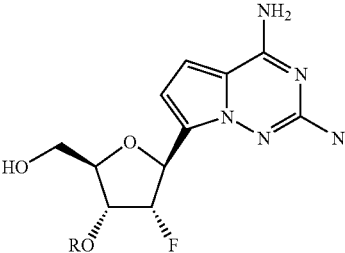
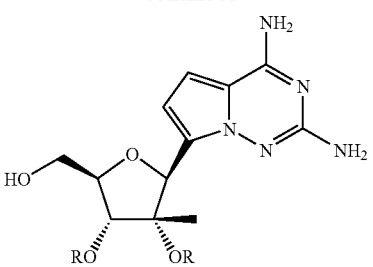
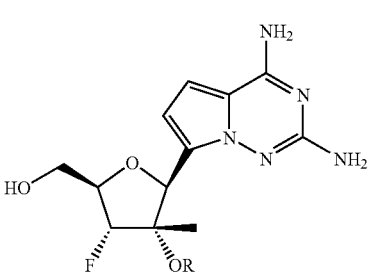
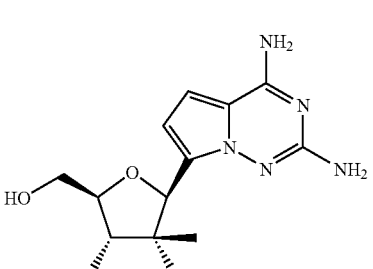
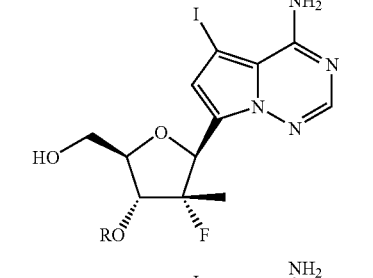
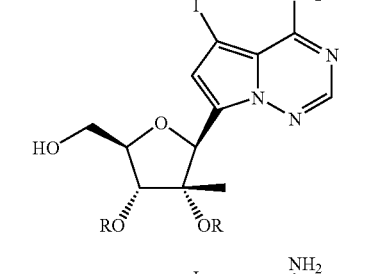
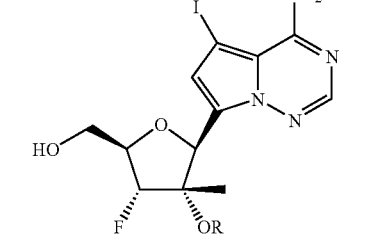

-continued
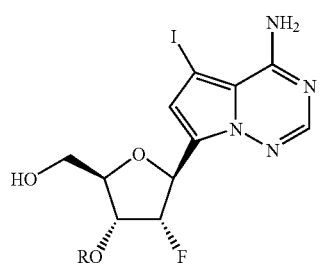
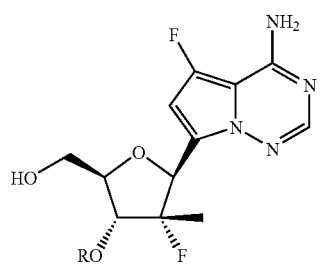
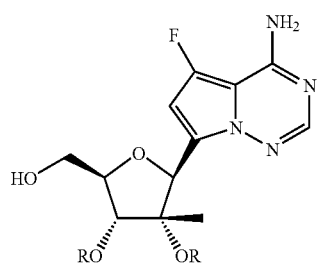
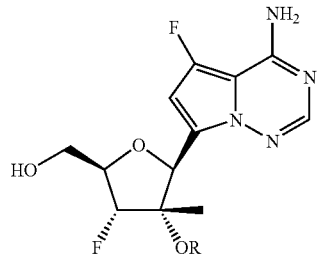
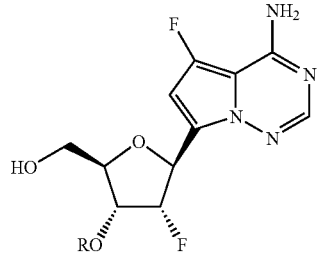
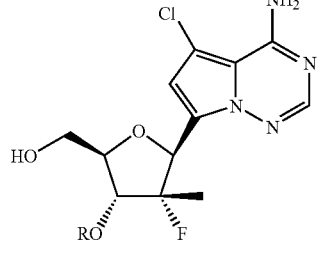
-continued
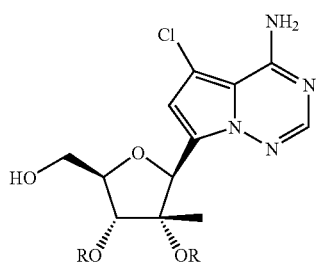
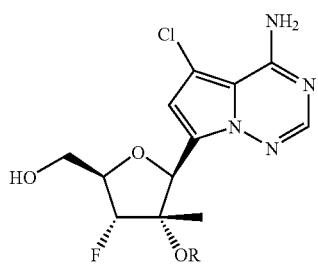
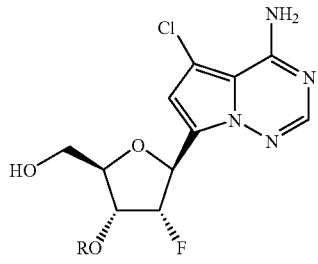
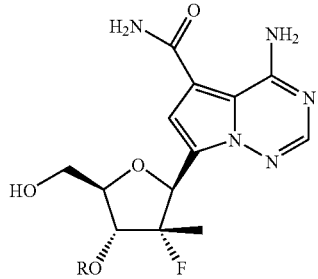
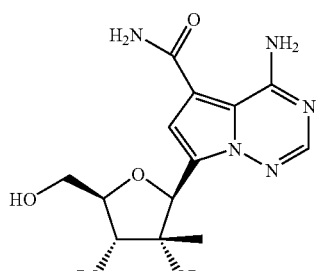
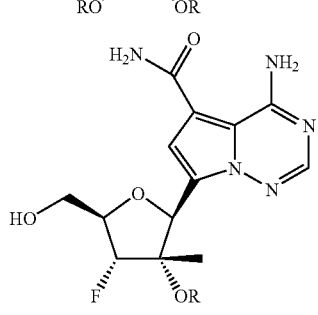

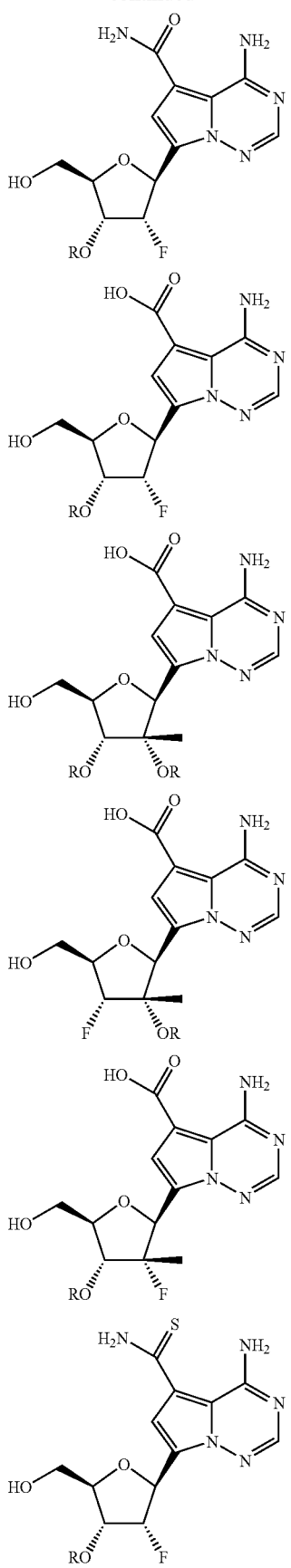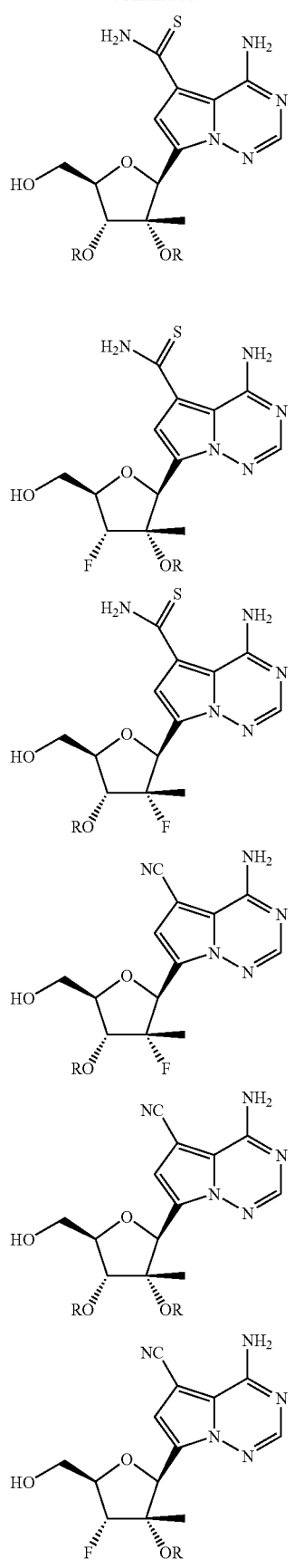

-continued
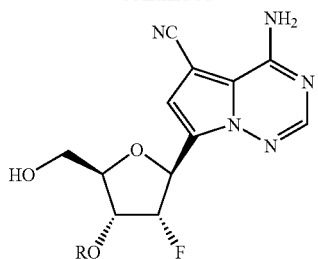
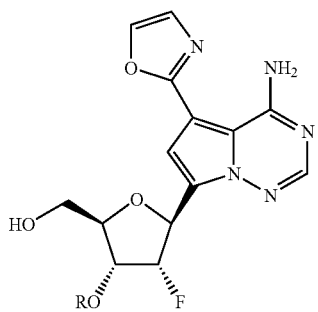
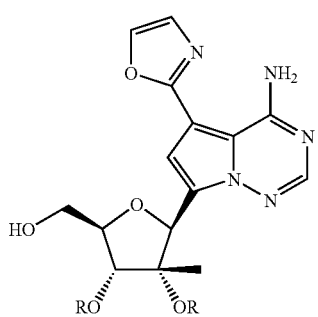
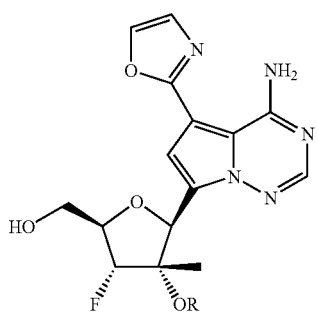
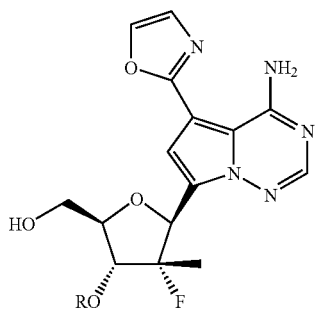
-continued
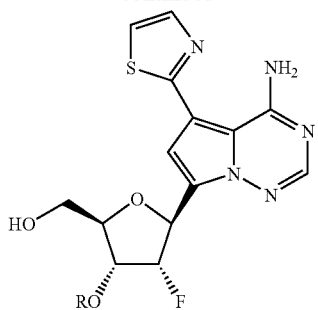
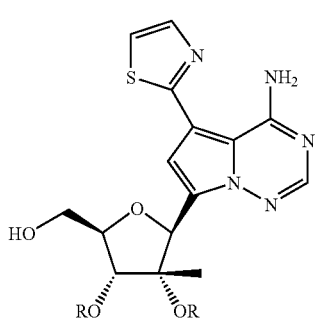
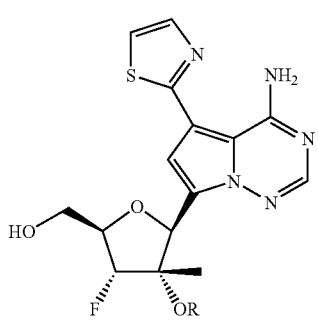
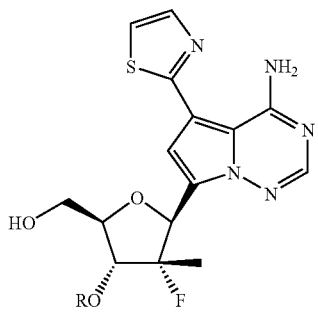
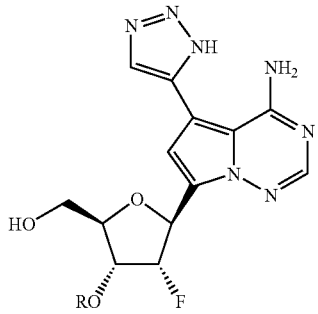

35
-continued
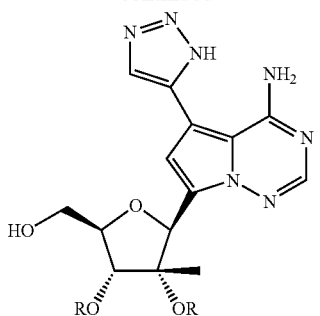
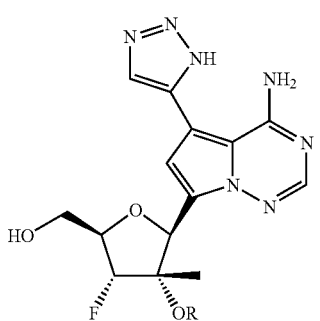
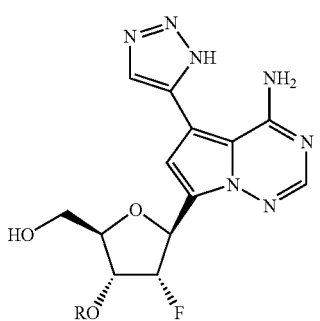
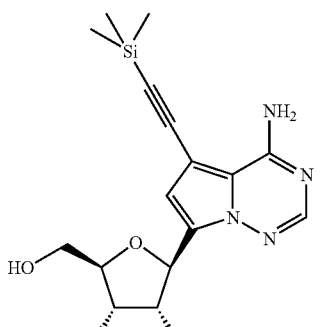
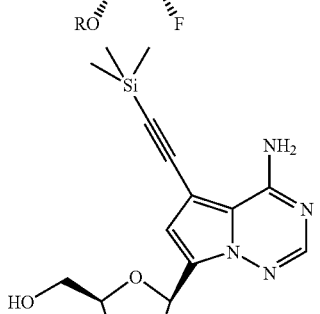
36
-continued
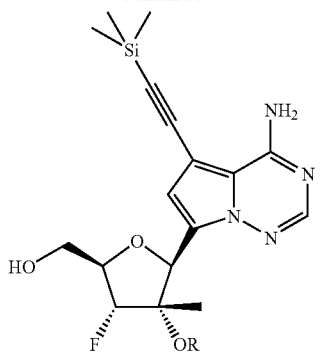
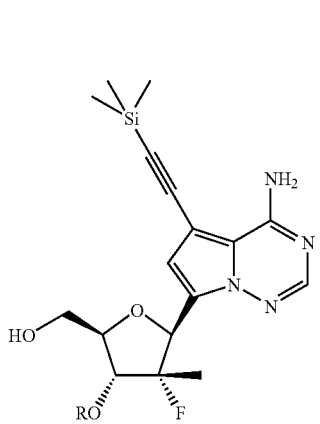
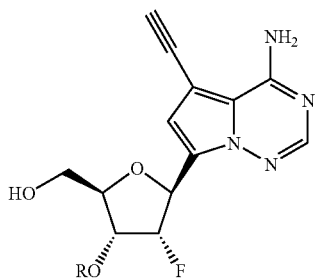
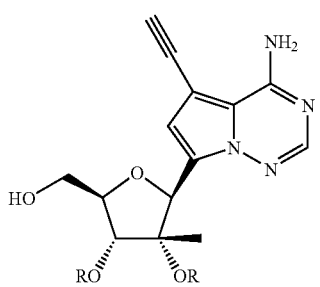
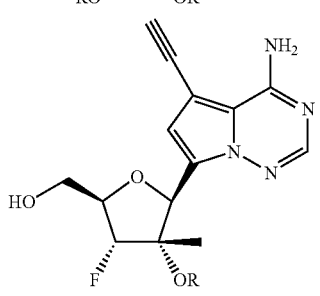

-continued
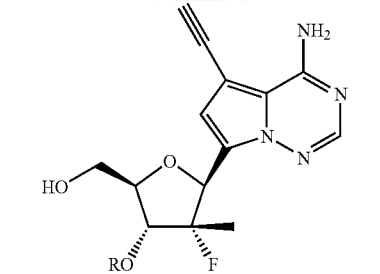
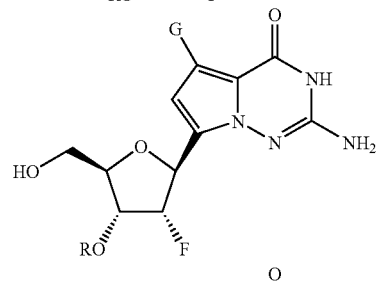
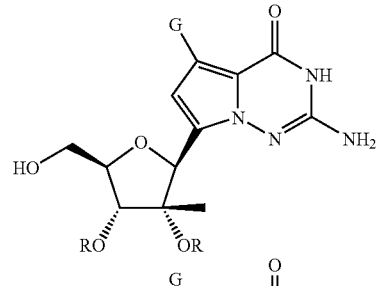
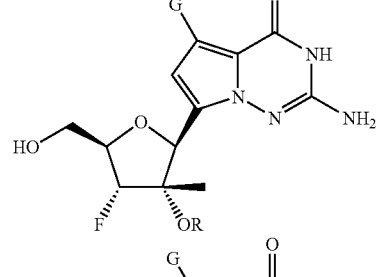
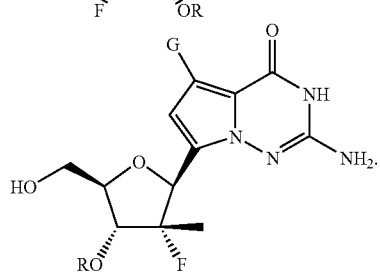
Furthermore, another embodiment of the compound of formula I may be represented by the following formulae, or salts, esters, solvates, hydrates or prodrugs thereof:
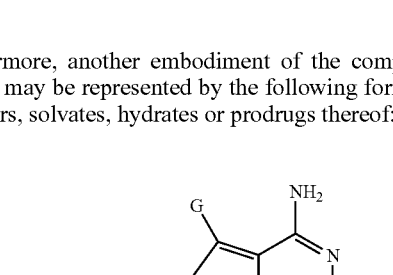
-continued
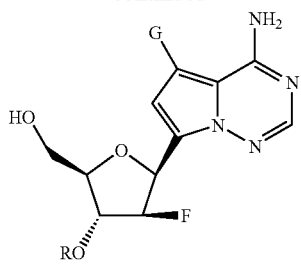
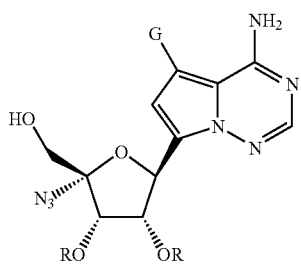
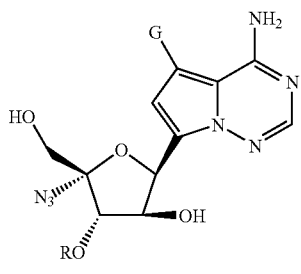
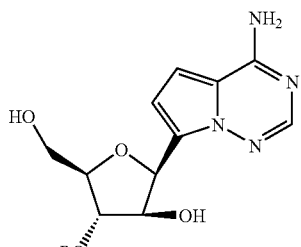
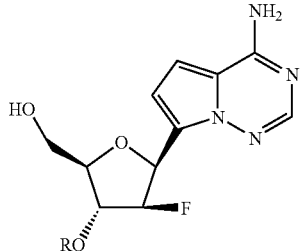
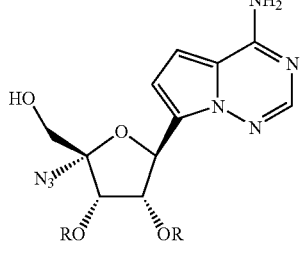

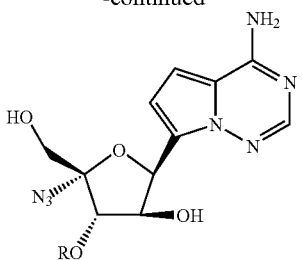
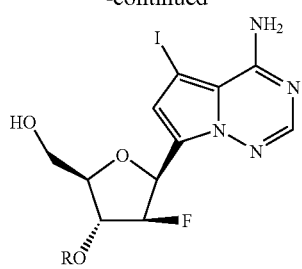
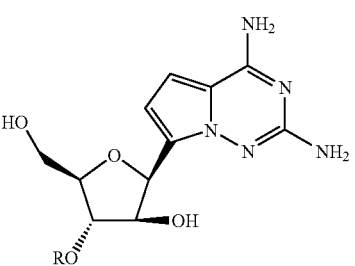
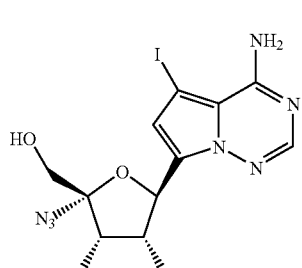
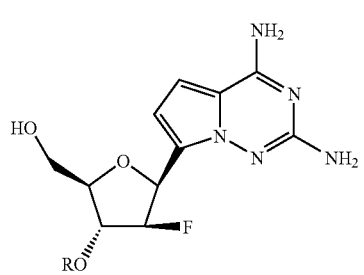
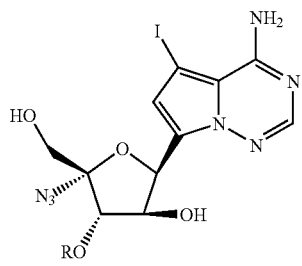
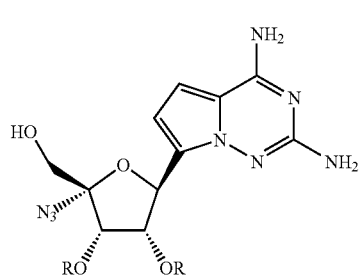
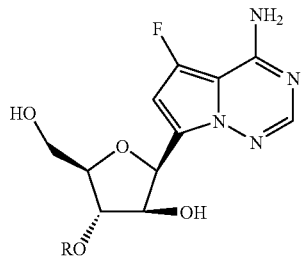
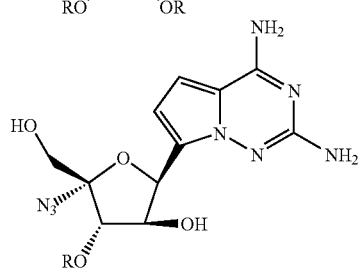
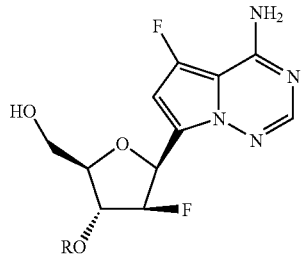
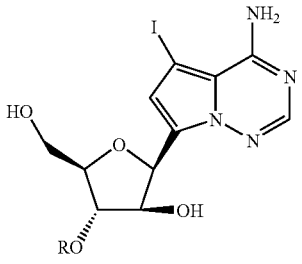
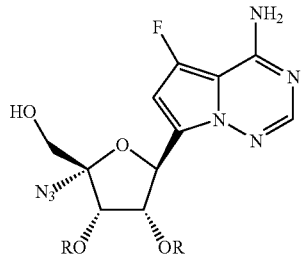

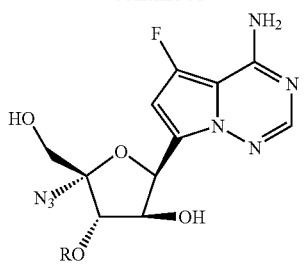
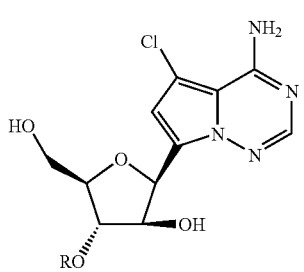
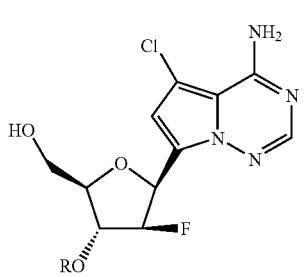
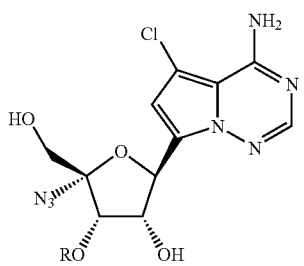
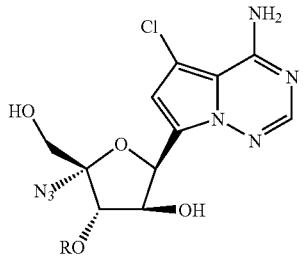
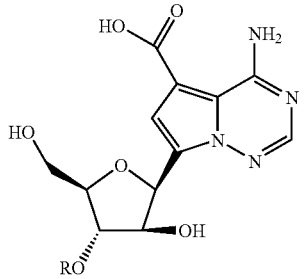
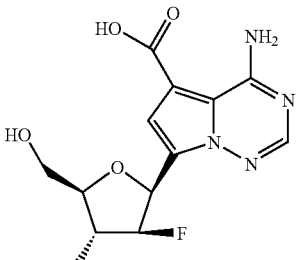
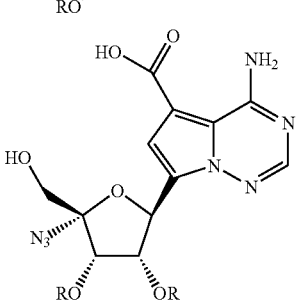
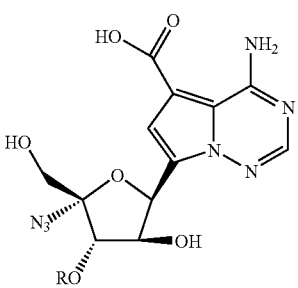
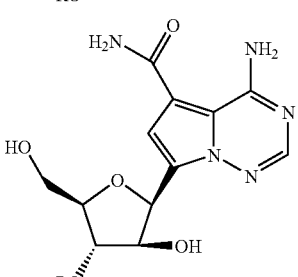
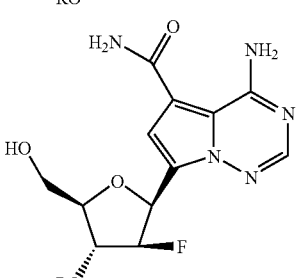
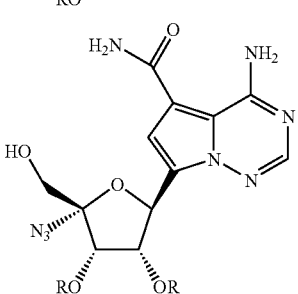

-continued
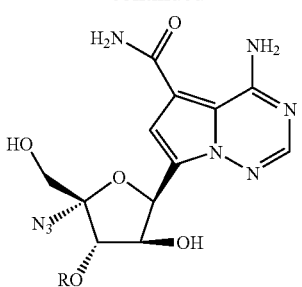
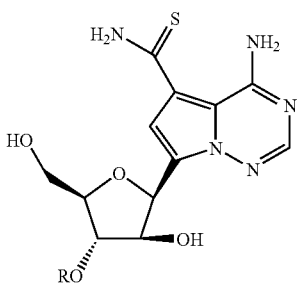
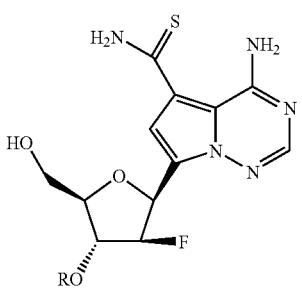
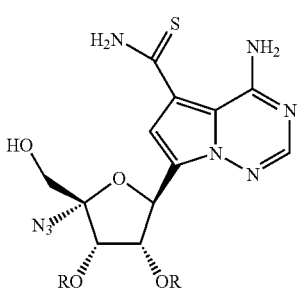
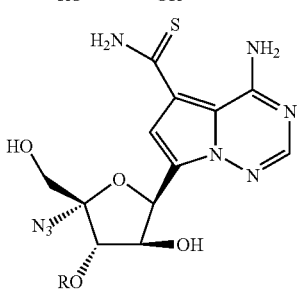
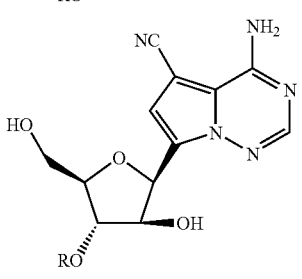
-continued
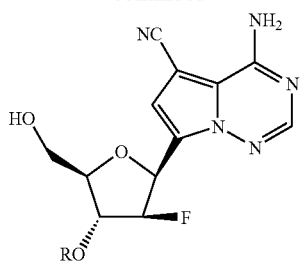
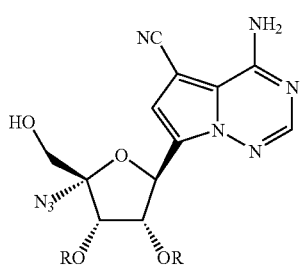
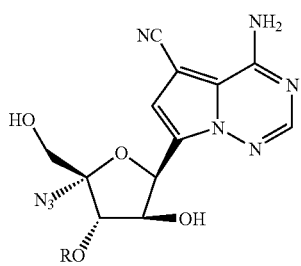
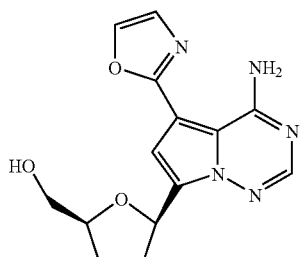
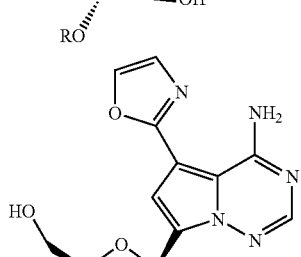
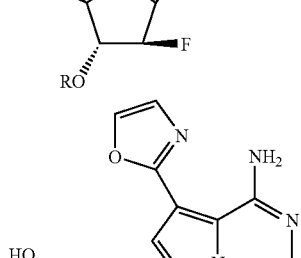
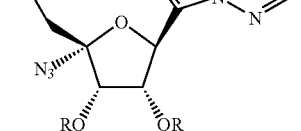

-continued
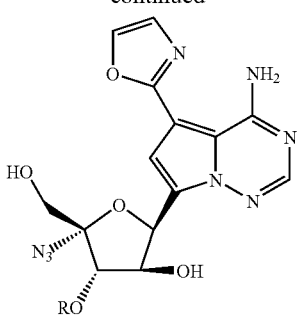
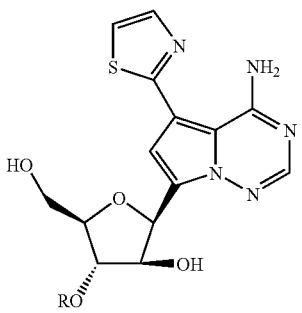
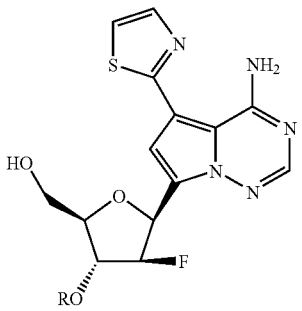
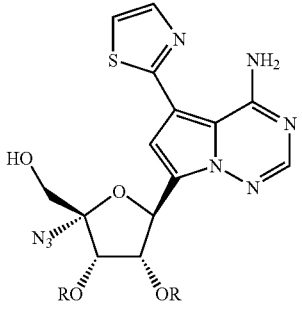
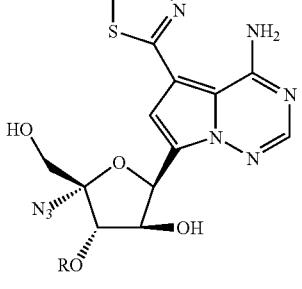
-continued
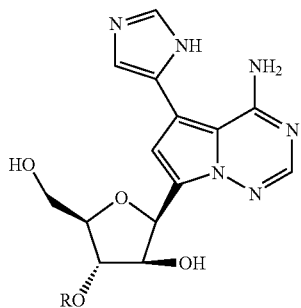
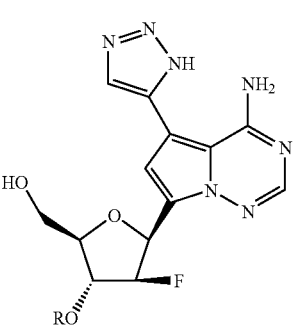
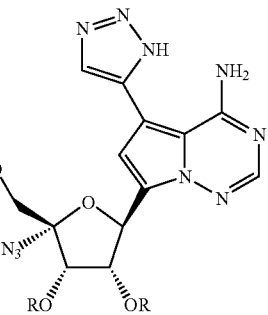
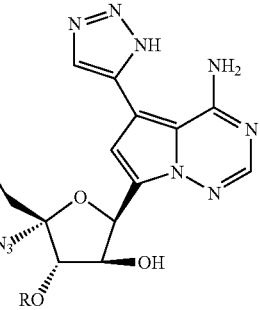
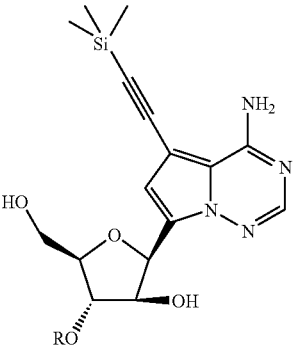

47

-continued

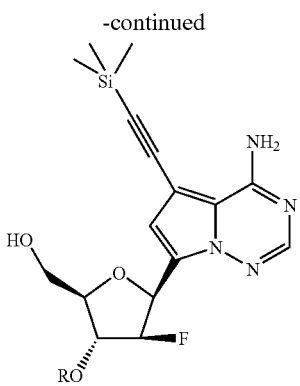

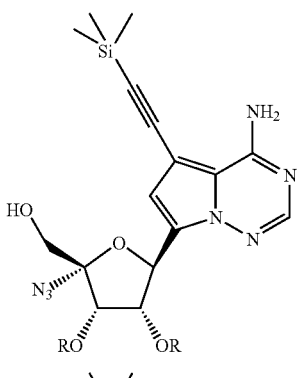

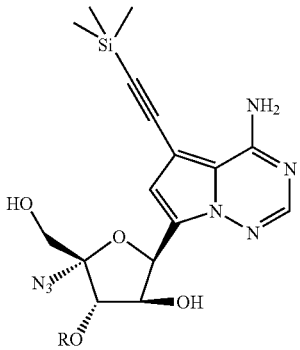

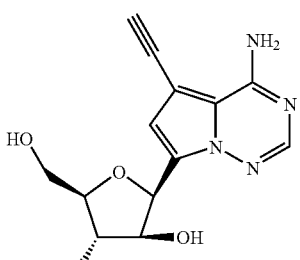

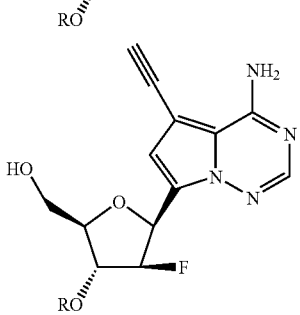

48

-continued

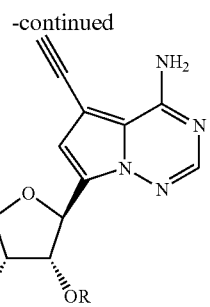

Each R may be halogen, —H, —OH, —SH, —CN, S($C_1$-$C_4$ alkyl), —$NO_2$, $NH_2$, —$NHNH_2$ or —$N_3$, —NR'R'. Each R' may independently be H, $C_1$-$C_4$ alkyl, —C(S)$NH_2$, —$CH_3$, —$CH_2$OH, —$CH_2NH_2$, —$CH_2NH_3^+$, —COOH, —COOC$H_3$, —COOC$H_2CH_3$, —CONHC$H_3$, —CON$H_2$, —C$F_3$, —N(C$H_3$)$_2$, —NHCOC$H_3$, —NHCON$H_2$, —NHC-NHN$H_2$, —ON$H_2$, —C$H_2$OC$H_3$, —O(C$H_2$)C$H_3$, COO($C_1$-$C_4$alkyl), substituted alkyl, substituted alkenyl, substituted alkynyl, substituted aryl, substituted acyl, substituted arylalkyl, substituted cycloalkyl, substituted cycloalkenyl, substituted phenyl, substituted heteroaryl, substituted heterocyclyl, substituted alkyloxy, substituted alkenyloxy, substituted alkynoxy, substituted aryloxy, substituted acyloxy, substituted oxyacyl, substituted arylalkoxy, substituted heterocycloxy, substituted heteroaryloxy, substituted cycloalkoxy, substituted cycloalkenoxy, substituted amino, substituted aminoacyl, substituted aminoacyloxy, substituted acylamino, substituted oxyacylamino, substituted oxyacyloxy, substituted acylimino, substituted acyliminoxy, substituted oxyacylimino, substituted aminothioacyl, substituted thioacylamino, substituted aminosulfinyl, substituted aminosulfonyl, substituted thio, substituted thioalkyl, substituted thioacyl, substituted thioacyloxy, substituted oxythioacyl, substituted oxythioacyloxy, substituted phosphorylamino, substituted sulfinyl, substituted sulfonyl, substituted sulfinylamino, substituted sulfonylamino, substituted oxysulfinylamino or substituted oxysulfonylamino. Each G may be —H, —F, —Cl, —I, —N$H_2$, —NHC$H_3$, —CN, —C≡CH, —C≡CC$H_3$, —C≡CC$H_2$OH, —C≡C—Si(C$H_3$)$_3$, —CON$H_2$, —CSN$H_2$, —COOH, —CONHC$H_3$, —CONH-phenyl, —CONH-methylphenyl, thiazole, oxazole, imidazole, imidazoline, triazole or tetrazole. The C-5 mono-phosphate, di-phosphate, and tri-phosphate derivatives thereof, or C-5 mono-phosphate, di-phosphate, and tri-phosphate mimic derivatives thereof.

In another embodiment, the sugar moiety may be represented by any one of the following structures:

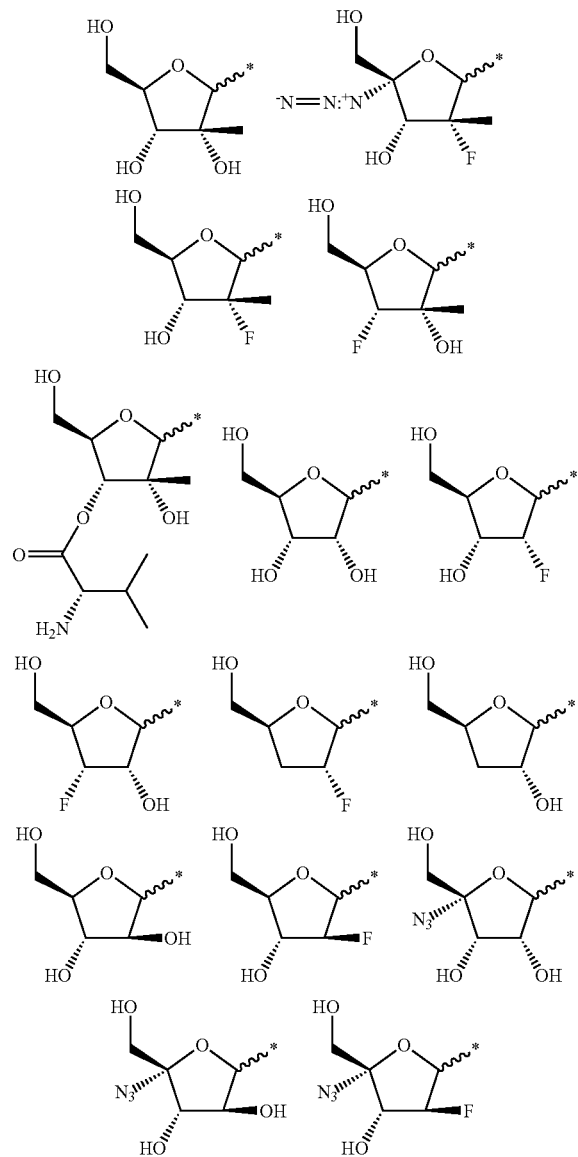

or C-5 mono-phosphate, di-phosphate and tri-phosphate derivatives thereof, or C-5 mono, di or tri-phosphate mimics. The nucleosides of the present disclosure also include derivatives such as nucleotides, and nucleotide mimics and/or prodrugs thereof such as phosphoesters and phosphoamidates.

In various embodiments, nucleotide mimics of the compounds of the present disclosure of formula I discussed above include a compound in which $R^5$ is a mono-phosphate or mono-phosphate mimic of formula (III) or (IV):

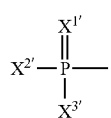
(III)

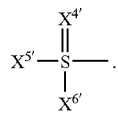
(IV)

The $X^{1'}$ $X^{4'}$, and $X^{6'}$ moieties are independently =O, =S or =NR. The $X^{2'}$, $X^{3'}$, and $X^{5'}$ moieties may be —H, —F, —NROR, —N$_3$, —CN, —(BH$_2$G)$^-$M$^+$, —(BH$_3$)$^-$M$^+$, —R, —OR, —SR or —NR$_2$. The substituents (BH$_2$G)$^-$M$^+$ and (BH$_3$)$^-$M$^+$ are ion pairs, which are linked to phosphorus through the negatively charged boron. M$^+$ is a cation, such as a pharmaceutically-acceptable cation like Ca$^{2+}$, ammonium, trialkylammonium or tetraalkylammonium, e.g., NH$_4^+$, Et$_3$NH$^+$, Bu$_3$NH$^+$, and Bu$_4$N$^+$.

In various embodiments, nucleotide mimics of the compounds of formula I as discussed above include di- and tri-phosphates and di- and tri-phosphate mimics including a compound in which $R^5$ is a di- or tri-phosphate moiety of formula (V):

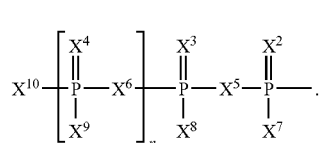
(V)

The $X^2$, $X^3$, and $X^4$ may be =O, =S, =Se or =NR. The $X^5$ and $X^6$ may be —O—, —S—, —Se—, —CY$_2$C(O)—, —CH(OH)—, —C(OH)$_2$—, —CH$_2$O—, —CH$_2$CH$_2$—, —CH$_2$CH(NH$_2$)—, —CH$_2$CH$_2$CH(NH$_2$)—, —CY$_2$OCY$_2$—, —CY$_2$—, —CRY—, —CY$_2$CY$_2$—, —CHR—, —C≡C—, —HC=CH—, —NH—, —NR—, >NOH, >NOR, >NNH$_2$ or >NNHR. The $X^7$, $X^8$, $X^9$ and $X^{10}$ may be —H, —F, —OR, —SR, —NR$_2$, —NROR, —NRNR$_2$, —CN, —N$_3$, —(BH$_3$)$^-$M$^+$, —(BH$_2$G)$^-$M$^+$, —R and —SeR; —Y, —R, wherein —(BH$_2$G)$^-$M$^+$, and —(BH$_3$)$^-$M$^+$ are as defined above. The n is 0 or 1.

The terms "phosphate mimic" (and variations thereof) unless otherwise specified, refers to a phosphate analogue, including, but not limited to, phosphonate, phosphothiolate, phosphoselenoate, selenophosphate, thiophosphate, P-boranophosphate, phosphoramidate, sulfamate, sulfonate, sulfonamide, and/or a combination thereof. Illustrative embodiments of the phosphate mimics include phosphonate, phosphoramidate, phosphorothioate, methylphosphonate, fluoromethylphosphonate, difluoromethylphosphonate, vinylphosphonate, phenylphosphonate, sulfonate, fluorophosphate, dithiophosphorothioate, 5'-methylenephosphonate, 5'-difluoromethylenephosphonate, 5'-deoxyphosphonate, 5'-aminophosphoramidate, and 5'-thiophosphate.

Also, it will be appreciated that the terms "di-phosphate mimic" and "tri-phosphate mimic" specifically refer to a di-phosphate analogue and a tri-phosphate analogue, respectively, which include at least one of the phosphate mimics, one of the modifications at the bridging site of di-phosphate and tri-phosphate (e.g., $X^5$, $X^6$ and $X^{10}$), and/or replacements of non-bridging phosphate oxygen atoms (e.g., $X^4$, $X^3$ and $X^2$).

Additional nucleotide phosphate mimics and methods of making appropriate phosphate mimics for compounds of the present disclosure are described, inter alia, in WO 2003/072757 and WO 2003/073989, the entire contents of which are incorporated herein by reference. Many of the nucleotide mimics discussed herein may be prepared by similar approaches as published or by using well-known knowledge of organophosphorous chemistry. Generally, phosphate mimics of the nucleosides and nucleotides of the present disclosure may inhibit enzyme function without phosphorylation and/or have enhanced nuclease stability relative to nucleotides with unmodified phosphate.

The α-P, β-P, and γ-P in the mono-phosphate, di-phosphate, and tri-phosphate mimics may independently adopt either R or S configurations when chiral.

In yet another embodiment of the present disclosure, a pharmaceutical dosage form comprises a compound of formula I and one or more pharmaceutically acceptable carriers, diluents and/or excipients.

In another embodiment of a pharmaceutical dosage form, a therapeutically effective dose of a compound of formula I is provided for a microbial infection, a viral infection, or a proliferative disorder in a human patient in the range of about 10 μg/kg to about 30 mg/kg.

In another embodiment, a pharmaceutical dosage form comprises sufficient compound of a compound of formula I to provide once a day dosing to a human patient.

Another aspect of the invention is a method of treating or preventing a microbial infection, a viral infection, or a proliferative disorder in a human patient comprising administering a pharmaceutical dosage form of a compound of formula I to the human patient.

In an exemplary embodiment of the methods, the condition is a viral infection.

In an exemplary embodiment of the methods, the viral infection is a Flaviviridae infection, preferably a hepatitis C viral infection.

In yet another embodiment, the method is directed to treating the hepatitis C viral infection in a human patient comprising administering to the human patient a pharmaceutical dosage form comprising a therapeutically effective amount of 4-amino-7-(2-C-methyl-β-D-ribofuranosyl)-pyrrolo[2,1-f][1,2,4]triazine and one or more pharmaceutically acceptable carriers, diluents and/or excipients.

In another embodiment of the present disclosure, a therapeutically effective amount is between about 10 μg/kg to about 30 mg/kg.

In yet another aspect of the present disclosure, a method of inhibiting polymerase activity in a human patient comprises administering a pharmaceutical dosage form to the human patient.

In an exemplary embodiment of the methods, the polymerase activity is HCV NS5B polymerase activity.

In another exemplary embodiment of the methods, a pharmaceutical dosage form is administered once a day.

In still another exemplary embodiment of the methods, a therapeutically active compound of the compound of formula I is $Z^1$ is H, $R^2$ is $CH_3$, and $R^5$ is H or

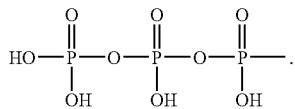

In yet another exemplary embodiment, a therapeutically active compound of a compound of formula I comprises a phosphoramidate or a phosphoester of $R^5$.

In yet another exemplary embodiment, a therapeutically active compound of a compound of formula I comprises a hydrochloride salt of the therapeutically active compound.

In another embodiment, a method is provided directed to treating a hepatitis C viral infection by administering to a patient, once per day, a pharmaceutical dosage form comprising a therapeutically effective amount of a compound:

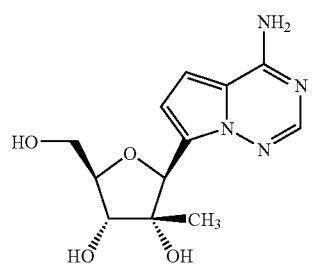

and one or more pharmaceutically acceptable carriers, diluents and/or excipients.

In yet another embodiment, a method is provided directed to administering to a patient a therapeutically effective amount of a compound of formula I in the range of about 10 μg/kg to about 30 mg/kg.

In another exemplary embodiment, the method comprises the in-vivo production of a therapeutically effective metabolite of a compound of formula I that has an intracellular half-life of greater than about 10 hours.

In another exemplary embodiment, the method comprises the in-vivo production of a therapeutically effective metabolite to allow for once a day dosing of formula I in a human patient in the range of about 10 μg/kg to about 30 mg/kg.

In another exemplary embodiment, the plasma half-life of a compound of formula I is greater than about 2 hours upon administration to a human patient.

In another exemplary embodiment, a pharmaceutical dosage form at an extracellular concentration of 10 μg/kg of a compound of formula I results in intracellular levels of a therapeutically active compound thereof in primary cells of greater than about 20 pmoles/million cells.

In another exemplary embodiment, a pharmaceutical dosage form comprises a therapeutically effective dose of a compound of formula I according to the structure:

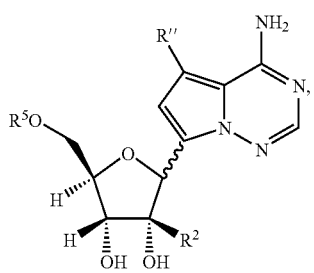

wherein:

R" is H, F, Cl, I, CN, CONH$_2$, C≡CSi(C$_{1-4}$ alkyl)$_3$, C≡CH, COOH, CSNH$_2$,

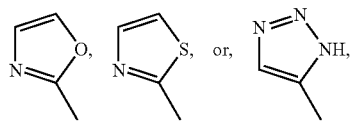

R$^2$ is C$_{1-4}$ alkyl, and
R$^5$ is H,

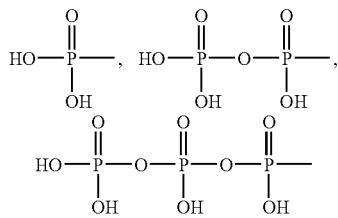

or mimic thereof, or, a salt, ester, solvate, hydrate or prodrug thereof, and one or more pharmaceutical carriers, diluents and/or excipients.

In another exemplary embodiment, a pharmaceutical dosage form comprises a compound of formula I as depicted above wherein R" is H, R$^2$ is CH$_3$, and R$^5$ is H or

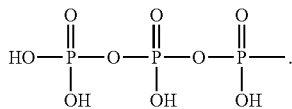

In another exemplary embodiment, a pharmaceutical dosage form comprises a phosphoramidate or a phosphoester of R$^5$.

In another exemplary embodiment, a pharmaceutical dosage form comprises a therapeutically effective dose of an active pharmaceutical ingredient according to the structure:

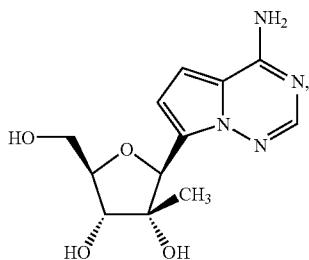

or, a salt, ester, solvate, hydrate or prodrug thereof, and one or more pharmaceutical carriers, diluents and/or excipients.

In yet another exemplary embodiment, a pharmaceutical dosage form comprises a therapeutically effective dose of an active pharmaceutical ingredient in the range of 10 µg/kg to 30 mg/kg.

In yet another exemplary embodiment, a pharmaceutical dosage form comprises a hydrochloride salt of an active pharmaceutical ingredient.

In another exemplary embodiment, a pharmaceutical dosage form comprises an ester of an active pharmaceutical ingredient.

In another exemplary embodiment, a pharmaceutical dosage form comprises a prodrug of an active pharmaceutical ingredient.

In another exemplary embodiment, the pharmaceutical dosage form is an oral, a rectal, a nasal, a topical, a buccal, a sublingual, a transdermal, a vaginal, an injection or a parental dosage form.

Compounds of the present disclosure can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes well known in the art, for example, by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximise the separation of the enantiomers.

Still another available method involves synthesis of covalent diastereomeric molecules, for example, esters, amides, acetals, ketals, and the like, by reacting compounds of formula I with an optically active acid in an activated form, an optically active diol, or an optically active isocyanate. The synthesised diastereoisomers can be separated by conventional means such as chromatography, distillation, crystallization or sublimation, and then hydrolyzed to deliver the enantiomerically pure compound. In some cases, hydrolysis to the parent optically active drug is not necessary prior to dosing the patient since the compound can behave as a prodrug. The optically active compounds of formula I can likewise be obtained by utilizing optically active starting materials.

In addition to the optical isomers or potential optical isomers discussed above, other types of isomers are specifically intended to be included in this disclosure. Examples include cis isomers, trans isomers, E isomers, Z isomers, syn-isomers, anti-isomers, tautomers and the like. Aryl, heterocyclyl, or heteroaryl tautomers, heteroatom isomers and ortho, meta, or para substitution isomers are also included as isomers. Solvates or solvent addition compounds such as hydrates or alcoholates are also specifically included both as chemicals of this disclosure and in, for example, formulations or pharmaceutical compositions for delivery.

Equivalents of the general formulas set forth above for the disclosed compounds and derivatives as well as the intermediates are compounds otherwise corresponding thereto and having the same general properties such as tautomers thereof and compounds wherein one or more of the various R groups are simple variations of the substituents as defined therein, for example, wherein R is a higher alkyl group than that indicated. In addition, where a substituent is designated as, or can be, hydrogen, the exact chemical nature of a substituent which is other than hydrogen at that position, for example, a halogen, hydroxy, amino, and the like functional group, is not critical so long as it does not adversely affect the overall activity and/or synthesis procedure. For example, two hydroxyl groups, two amino groups, two thiol groups or a mixture of two hydrogen-heteroatom groups on the same carbon are known not to be stable without protection or as a derivative.

Basic nitrogen-containing groups may be quarternized with such agents as lower alkyl halide, such as methyl, ethyl, propyl, and butyl chlorides, bromides and iodides; dialkyl sulfates like dimethyl and diethyl sulfate; and others.

In some embodiments, the compounds disclosed herein, such as the nucleosides and nucleotides, also include the prodrug derivatives thereof, which are covalently modified latent forms of the therapeutically-active compound.

The term "prodrug" is used in its broadest sense and encompasses those compounds that when administered in a biological system are converted or activated in vivo to therapeutically-active compounds by, for example, a spontaneous chemical reaction, a metabolic chemical reaction, an enzyme catalysed chemical reaction, and/or photolysis. Illustratively, a prodrug can be activated either by cellular enzymes or by chemical cleavage such as hydrolysis to release (liberate) the nucleoside, nucleotide or nucleotide mimic after the prodrug enters cells. Examples of prodrugs include compounds that can be oxidised, reduced, esterified, deesterified, alkylated, dealkylated, acylated, deacylated, aminated, deaminated, phosphorylated, dephosphorylated, photolyzed, and/or hydrolysed. Enzymes that may be capable of enzymatic conversion or activation of a prodrug to a therapeutically-active compound include, for example, amidases, cholinesterases, esterases, lipases, nucleases, oxidases, phospholipases, phosphases, and/or reductases. Such prodrug modification may improve or enhance, for example, drug absorption, solubility, lipophilicity, bioavailability, efficacy, and/or drug delivery into cells.

Prodrug derivatives of the compounds of the present disclosure may be prepared by modification of the sugar moiety or of the phosphate or phosphate mimic to include a prodrug substituent. A prodrug may also include a labile protecting group on the functional moiety or therapeutically-active compound as described herein. In addition to those described herein, prodrug derivatives of nucleosides, nucleotides and nucleotide phosphate mimics and methods of making the prodrugs appropriate for use in the present disclosure are described, inter alia, in PCT Publications WO 2003/072757 and WO 2003/073989 and U.S. Patent application publication US20020361177.

Prodrugs are compounds that are pharmacologically inert but are converted by enzyme or chemical action to an active form of the drug (i.e., an active pharmaceutical ingredient) at or near the predetermined target site. In other words, prodrugs are inactive compounds that yield an active compound upon metabolism in the body, which may or may not be enzymatically controlled. Prodrugs may also be broadly classified into two groups: bioprecursor and carrier prodrugs. Prodrugs may also be subclassified according to the nature of their action. Bioprecursor prodrugs are compounds that already contain the embryo of the active species within their structure, whereby the active species are produced upon metabolism. For example, the first prodrug, antibacterial prontosil, is metabolized in vivo to its active metabolite sulphanilamide. Carrier prodrugs are formed by combining the active drug with a carrier species forming a compound having desirable chemical and biological characteristics, whereby the link is an ester or amide so that the carrier prodrug is easily metabolized upon absorption or delivery to the target site. For example, lipophilic moieties may be incorporated to improve transport through membranes. Carrier prodrugs linked by a functional group to carrier are referred to as bipartate prodrugs. Prodrugs where the carrier is linked to the drug by a separate structure are referred to as tripartate prodrugs, whereby the carrier is removed by an enzyme-controlled metabolic process, and whereby the linking structure is removed by an enzyme system or by a chemical reaction. (Thomas G, Medicinal Chemistry: An Introduction, 2000, John Wiley & Sons, Ltd. pp. 12, 17, 243 and 364-372)(See also, Wermuth C G, 2003, The Practice of Medicinal Chemistry, 2nd Ed., *Academic Press* 33:561-582). Hydroxy-protecting group refers to any suitable group, such as tert-butyloxy-carbonyl (t-BOC) and t-butyl-dimethyl-silyl (TBS). Other hydroxy protecting groups are shown in Hanson J R, 1999, *Protecting Groups in Organic Synthesis*, Sheffield Academic Press, 2:8-35, which is incorporated herein by reference.

Illustratively, when administered to a host, a prodrug is generally administered as a pharmaceutically-acceptable prodrug that is metabolised to form the therapeutically-active compound and the prodrug moiety or substituent through, for example, hydrolysis or oxidation by enzymatic activity or by acid or base solvolysis. A "prodrug moiety" or "prodrug substituent" refers to the labile group that is removed from the therapeutically-active compound through a metabolic, hydrolytic, and/or enzymatic process. However, non-pharmaceutically-acceptable prodrugs also fall within the scope of the present disclosure and may be use used, for example, in in vitro assays to improve solubility and/or as intermediates in the preparation of pharmaceutically-acceptable prodrugs or other compounds.

Illustrative prodrugs moieties include, but are not limited to residues of: proteins; antibiotics; D- and L-amino acids which may be attached to a phosphate moiety or a phosphate mimic moiety via a carbon atom (phosphonates), a nitrogen atom (phosphoamidates), or an oxygen atom (phosphoesters) or may be attached to the sugar moiety through any one or more of the $R^1$-$R^5$ groups; peptides (preferably up to 10 amino acids) attached to a phosphate moiety or a phosphate mimic moiety via a carbon atom (phosphonates), a nitrogen atom (phosphoamidates), or an oxygen atom (phosphoesters), or may be attached to the sugar moiety through any one or more of the $R^1$-$R^5$ groups; drug moieties attached to a phosphate moiety or a phosphate mimic moiety via a carbon atom (phosphonates), a nitrogen atom (phosphoamidates), or an oxygen atom (phosphoesters), or may be attached to the sugar moiety through any one or more of the $R^1$-$R^5$ groups; as well as including steroids; vitamins; polyamines; carbohydrates; polyethylene glycols (PEGs); cyclosaligenyls; substituted 4 to 8-membered rings, with or without heteroatom substitutions, 1,3-phosphoramidate attachments to a terminal phosphate or phosphate mimic moiety ($\gamma$ or $\beta$) or connecting between an $\alpha,\beta$ or $\beta,\gamma$ of a phosphate moiety or phosphate mimic moiety, and so on. Phosphoesters and phosphoamidates are particularly preferred prodrug moieties.

In one embodiment, the prodrug of a nucleoside 5'-monophosphate mimic can mask the negative charges of the phosphate mimic moiety entirely or partially, or mask the negative charges of the di-phosphate mimic or tri-phosphate mimic moiety or phosphate moiety in order to, for example, enhance drug absorption and/or drug delivery into cells.

In another embodiment one or more prodrug substituents or moieties may be attached to one or more $X^{2'}$, $X^{3'}$ and $X^{5'}$ positions on a nucleoside mono-phosphate mimic or to one or more $X^7$—$X^{10}$ positions on a nucleoside di- or tri-phosphate mimic. Illustrative prodrug substituents in positions $X^{2'}$, $X^{3'}$ or $X^{5'}$ position include 2,3-O-diacylglyceryloxy, 2,3-O-dialkylglyceryloxy, 1-O-alkyl-2-O-acylglyceryloxy, 1-O-acyl-2-O-alkylglyceryloxy, 1-S-alkyl-2-O-acyl-1-thioglyceryloxy, acyloxymethoxy, S-acyl-2-thioethoxy, S-pivaloyl-2-thioethoxy, acyloxymethoxy, pivaloyloxymethoxy, alkoxycarbonyloxymethoxy, S-alkyldithio-S'-ethyoxy acyloxymethoxy, S-acyl-2-thioethoxy, S-pivaloyl-2-thioethoxy, pivaloyloxymethoxy, alkoxycarbonyloxymethoxy, and S-alkyldithio-S'-ethyoxy.

In a further embodiment, the prodrug substituent is a substituent on a hydroxyl group of the sugar moiety (that is, for instance, any one of $R^1$-$R^5$). Illustratively, the modification results in the formation of an ester and in this regard the preferred prodrug substituents are $C_1$-$C_6$ acyl groups for example, acetyl, propionyl, pivaloyl, etc. Also preferred are substituted $C_1$-$C_6$ acyl moieties, for example, fluoroacetyl, difluoroacetyl, etc. More preferably the substituted $C_1$-$C_6$ acyl group is represented as a residue of an L or D amino acid consisting of alanine, asparagine, cysteine, glutamine, glycine, isoleucine, leucine, methionine, phenylalanine, proline, serine, threonine, tryptophan, tyrosine, valine, aspartic acid, glutamic acid, arginine, histidine, and lysine. Most preferably the prodrug substituent is an amino acid residue of D or L-valine.

The pharmaceutically suitable oral carrier systems (also referred to as drug delivery systems, which are modern technology, distributed with or as a part of a drug product that allows for the uniform release or targeting of drugs to the body) preferably include FDA-approved and/or USP-approved inactive ingredients. Under 21 CFR 210.3(b)(8), an inactive ingredient is any component of a drug product other than the active ingredient. According to 21 CFR 210.3(b)(7), an active ingredient is any component of a drug product intended to furnish pharmacological activity or other direct effect in the diagnosis, cure, mitigation, treatment, or prevention of disease, or to affect the structure or any function of the body of humans or other animals. Active ingredients include those components of the product that may undergo chemical change during the manufacture of the drug product and be present in the drug product in a modified form intended to furnish the specified activity or effect. As used herein, a kit (also referred to as a dosage form) is a packaged collection of related material, including packages that are adapted, for example, for once daily administration of a dosage form.

As used herein, the oral dosage form includes capsules (a solid oral dosage form consisting of a shell and a filling, whereby the shell is composed of a single sealed enclosure, or two halves that fit together, which are sometimes sealed with a band, and whereby capsule shells may be made from gelatin, starch, cellulose, or other suitable materials, may be soft or hard, and are filled with solid or liquid ingredients that can be poured or squeezed), capsule or coated pellets (solid dosage form in which the drug is enclosed within either a hard or soft soluble container or "shell" made from a suitable form of gelatin; the drug itself is in the form of granules to which varying amounts of coating have been applied), capsule coated extended release (a solid dosage form in which the drug is enclosed within either a hard or soft soluble container or "shell" made from a suitable form of gelatin; additionally, the capsule is covered in a designated coating, which releases a drug or drugs in such a manner to allow at least a reduction in dosing frequency as compared to drug or drugs presented as a conventional dosage form), capsule delayed release (a solid dosage form in which the drug is enclosed within either a hard or soft soluble container made from a suitable form of gelatin, which releases a drug (or drugs) at a time other than promptly after administration, whereby enteric-coated articles are delayed release dosage forms), capsule delayed release pellets (solid dosage form in which the drug is enclosed within either a hard or soft soluble container or "shell" made from a suitable form of gelatin); the drug itself is in the form of granules to which enteric coating has been applied, thus delaying release of the drug until its passage into the intestines), capsule extended release (a solid dosage form in which the drug is enclosed within either a hard or soft soluble container made from a suitable form of gelatin, which releases a drug or drugs in such a manner to allow a reduction in dosing frequency as compared to that drug or drugs presented as a conventional dosage form), capsule film-coated extended release (a solid dosage form in which the drug is enclosed within either a hard or soft soluble container or "shell" made from a suitable form of gelatin; additionally, the capsule is covered in a designated film coating, which releases a drug or drugs in such a manner to allow at least a reduction in dosing frequency as compared to drug or drugs presented as a conventional dosage form), capsule gelatin coated (a solid dosage form in which the drug is enclosed within either a hard or soft soluble container made from a suitable form of gelatin; through a banding process, the capsule is coated with additional layers of gelatin so as to form a complete seal), capsule liquid filled (a solid dosage form in which the drug is enclosed within a soluble, gelatin shell which is plasticized by the addition of a polyol, such as sorbitol or glycerin, and is therefore of a somewhat thicker consistency than that of a hard shell capsule; typically, the active ingredients are dissolved or suspended in a liquid vehicle), granule (a small particle or grain), pellet (a small sterile solid mass consisting of a highly purified drug, with or without excipients, made by the formation of granules, or by compression and molding), pellets coated extended release (a solid dosage form in which the drug itself is in the form of granules to which varying amounts of coating have been applied, which releases a drug or drugs in such a manner to allow a reduction in dosing frequency as compared to that drug or drugs presented as a conventional dosage form), pill (a small, round solid dosage form containing a medicinal agent intended for oral administration), powder (an intimate mixture of dry, finely divided drugs and/or chemicals that may be intended for internal or external use), elixir (a clear, pleasantly flavored, sweetened hydroalcoholic liquid containing dissolved medicinal agents; it is intended for oral use), chewing gum (a sweetened and flavored insoluble plastic material of various shapes which when chewed, releases a drug substance into the oral cavity), syrup (an oral solution containing high concentrations of sucrose or other sugars; the term has also been used to include any other liquid dosage form prepared in a sweet and viscid vehicle, including oral suspensions), tablet (a solid dosage form containing medicinal substances with or without suitable diluents), tablet chewable (a solid dosage form containing medicinal substances with or without suitable diluents that is intended to be chewed, producing a pleasant tasting residue in the oral cavity that is easily swallowed and does not leave a bitter or unpleasant after-taste), tablet coated (a solid dosage form that contains medicinal substances with or without suitable diluents and is covered with a designated coating), tablet coated particles (a solid dosage form containing a conglomerate of medicinal particles that have each been covered with a coating), tablet delayed release (a solid dosage form which releases a drug or drugs at a time other than promptly after administration, whereby enteric-coated articles are delayed release dosage forms), tablet delayed release particles (a solid dosage form containing a conglomerate of medicinal particles that have been covered with a coating which releases a drug or drugs at a time other than promptly after administration, whereby enteric-coated articles are delayed release dosage forms), tablet dispersible (a tablet that, prior to administration, is intended to be placed in liquid, where its contents will be distributed evenly throughout that liquid, whereby term 'tablet, dispersible' is no longer used for approved drug products, and it has been replaced by the term 'tablet, for suspension'), tablet effervescent (a solid dosage form containing mixtures of acids, e.g., citric acid, tartaric acid, and sodium bicarbonate, which release carbon dioxide when dissolved in water, whereby it is intended to be dissolved or dispersed in water before administration), tablet extended release (a solid dosage form containing a drug which allows at least a reduction in dosing frequency as compared to that drug presented in conventional dosage form), tablet film coated (a solid dosage form that contains medicinal substances with or without suitable diluents and is coated with a thin layer of a water-insoluble or water-soluble polymer), tablet film coated extended release (a solid dosage form that contains medicinal substances with or without suitable diluents and is coated with a thin layer of a water-insoluble or water-soluble polymer; the tablet is formulated in such manner as to make the contained medicament available over an extended period of time following ingestion), tablet for solution (a tablet that forms a solution when placed in a liquid), tablet for suspension (a tablet that forms a suspension when placed in a liquid, which is formerly referred to as a 'dispersible tablet'), tablet multilayer (a solid dosage form containing medicinal substances that have been compressed to form a multiple-layered tablet or a tablet-within-a-tablet, the inner tablet being the core and the outer portion being the shell), tablet multilayer extended release (a solid dosage form containing medicinal substances that have been compressed to form a multiple-layered tablet or a tablet-within-a-tablet, the inner tablet being the core and the outer portion being the shell, which, additionally, is covered in a designated coating; the tablet is formulated in such manner as to allow at least a reduction in dosing frequency as compared to that drug presented as a conventional dosage form), tablet orally disintegrating (a solid dosage form containing medicinal substances which disintegrates rapidly, usually within a matter of seconds, when placed upon the tongue), tablet orally disintegrating delayed release (a solid dosage form containing medicinal substances which disintegrates rapidly, usually within a matter of seconds, when placed upon the tongue, but which releases a drug or drugs at a time other than promptly after administration), tablet soluble (a solid dosage form that contains medicinal substances with or without suitable diluents and possesses the ability to dissolve in fluids), tablet sugar coated (a solid dosage form that contains medicinal substances with or without suitable diluents and is coated with a colored or uncolored water-soluble sugar), osmotic, and the like.

The oral dosage form composition contains an active pharmaceutical ingredient and one or more inactive pharmaceutical ingredients such as diluents, solubilizers, alcohols, binders, controlled release polymers, enteric polymers, disintegrants, excipients, colorants, flavorants, sweeteners, antioxidants, preservatives, pigments, additives, fillers, suspension agents, surfactants (e.g., anionic, cationic, amphoteric and nonionic), and the like. Various FDA-approved topical inactive ingredients are found at the FDA's "The Inactive Ingredients Database" that contains inactive ingredients specifically intended as such by the manufacturer, whereby inactive ingredients can also be considered active ingredients under certain circumstances, according to the definition of an active ingredient given in 21 CFR 210.3(b)(7). Alcohol is a good example of an ingredient that may be considered either active or inactive depending on the product formulation.

In addition to using prodrug approaches, the delivery of the compounds described herein including the nucleosides and/or nucleotides may be assisted by using a therapeutically acceptable carrier such as liposomal suspensions, cationic lipids, and polyimines.

The nucleosides of the present disclosure can be prepared by those who are skilled in synthetic organic and nucleoside chemistry using established synthetic methodology (*Chemistry of Nucleosides and Nucleotides* Vol. 1, 2, 3, edited by Townsend, Plenum Press; *Handbook of Nucleoside Synthesis* by Vorbrüggen Ruh-Pohlenz, John Wiley & Sons, Inc., 2001; *The Organic Chemistry of Nucleic Acids* by Yoshihisa Mizuno, Elsevier, 1986). If required, nucleosides of the present disclosure can be converted to their corresponding mono-phosphate, di-phosphate, and tri-phosphate by established phosphorylation procedures.

Schemes A-D illustrate chemical processes and transformations that may be useful for the preparation of compounds in the present disclosure, such as compounds of formula I and similar compounds.

Glycosyol pyrrolo-triazines can be prepared by glycosylation of intact pyrrolo-triazines as shown in Scheme A. Conditions used for such glycosidations are well known to practitioners in the art.

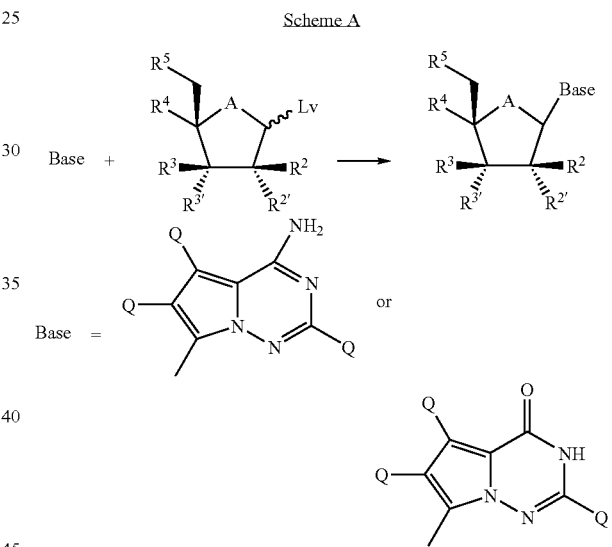

Scheme A

In Scheme A, preferably A is —O—, —CH$_2$— or optionally protected —N—; R$^2$, R$^{2'}$, R$^3$, R$^{3'}$, R$^{4'}$ are each independently —H, halogen, alkyl, —O-alkyl, —OH, optionally protected —O, methyl, or —F; R$^5$ is an optionally protected —OH or —NH$_2$; Lv is a leaving group; and Q is independently halogen, —H, —OH, —SH, —CN, S(C$_1$-C$_4$alkyl), —NO$_2$, NH$_2$, —NHNH$_2$, —N$_3$, —NR'R' wherein each R' is independently H or C$_1$-C$_4$ alkyl, —C(S)NH$_2$, —CH$_3$, —CH$_2$OH, —CH$_2$NH$_2$, —CH$_2$NH$_3^+$, —COOH, —COOCH$_3$, —COOCH$_2$CH$_3$, —CONHCH$_3$, —CONH$_2$, —CF$_3$, —N(CH$_3$)$_2$, —NHCOCH$_3$, —NHCONH$_2$, —NHCNHNH$_2$, —ONH$_2$, —CH$_2$OCH$_3$, —O(CH$_2$)CH$_3$, COOC$_1$-C$_4$alkyl, optionally substituted alkyl, optionally substituted alkenyl, optionally substituted alkynyl, optionally substituted aryl, optionally substituted acyl, optionally substituted arylalkyl, optionally substituted cycloalkyl, optionally substituted cycloalkenyl, optionally substituted phenyl, optionally substituted heteroaryl, optionally substituted heterocyclyl, optionally substituted alkyloxy, optionally substituted alkenyloxy, optionally substituted alkynoxy, optionally substituted aryloxy, optionally substituted acyloxy, optionally substituted oxyacyl, optionally substituted arylalkoxy, optionally substituted heterocycloxy, optionally substituted heteroaryloxy, optionally substituted cycloalkoxy, optionally substituted cycloalkenoxy, optionally substituted amino, optionally substituted aminoacyl, optionally substituted aminoacyloxy, optionally substituted acylamino, optionally substituted oxyacylamino, optionally substituted oxyacyloxy, optionally substituted acylimino, optionally substituted acyliminoxy, optionally substituted oxyacylimino, optionally substituted aminothioacyl, optionally substituted thioacylamino, optionally substituted aminosulfinyl, optionally substituted aminosulfonyl, optionally substituted thio, optionally substituted thioalkyl, optionally substituted thioacyl, optionally substituted thioacyloxy, optionally substituted oxythioacyl, optionally substituted oxythioacyloxy, optionally substituted phosphorylamino, optionally substituted sulfinyl, optionally substituted sulfonyl, optionally substituted sulfinylamino, optionally substituted sulfonylamino, optionally substituted oxysulfinylamino, optionally substituted oxysulfonylamino, thiazole, oxazole, imidazole, imidazoline, triazole, and tetrazole.

The compounds described herein can also be converted into their corresponding mono-phosphates, di-phosphates, and tri-phosphates using well established methods. Furthermore, as discussed above, prodrugs of mono-phosphates, di-phosphates, and tri-phosphates can be prepared in order to optimise the biological efficacy of these phosphorylated compounds. Methods for preparing such prodrugs are well known in the art (see, for example, Wagner, C. R., et al. *Med. Res. Rev.*, 2000, 20, 417-451).

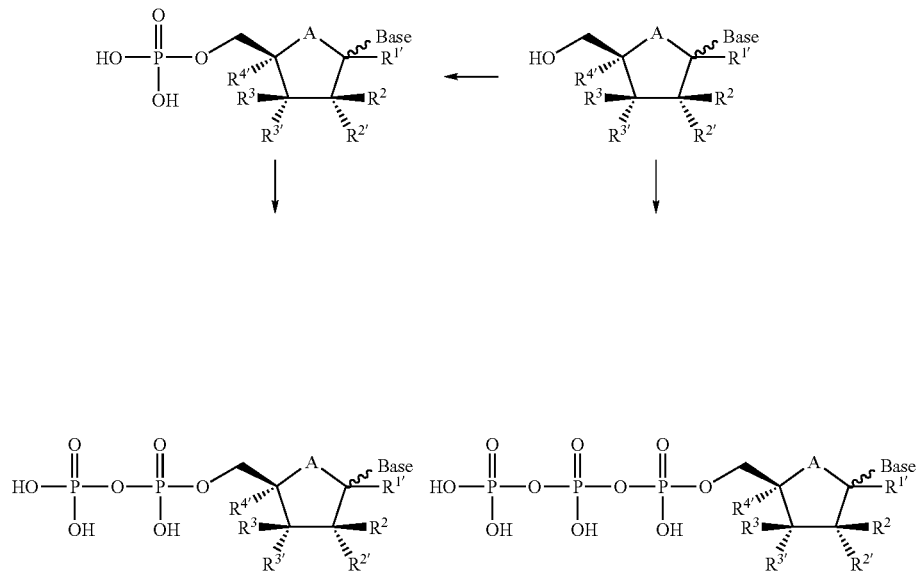

In Scheme B, preferably A is —O—, —CH$_2$—, or optionally protected —N—; R$^{1'}$, R$^2$, R$^{2'}$, R$^3$, R$^{3'}$, R$^{4'}$ are each independently —H, halogen, alkyl, —O-alkyl, —OH, optionally protected —O—, or methyl, and Base is as described herein.

As discussed earlier, an alternative to the use of phosphates is the use of phosphate mimics and their prodrugs. One such phosphate mimic is shown below and can be prepared using appropriately protected nucleosides and known conditions.

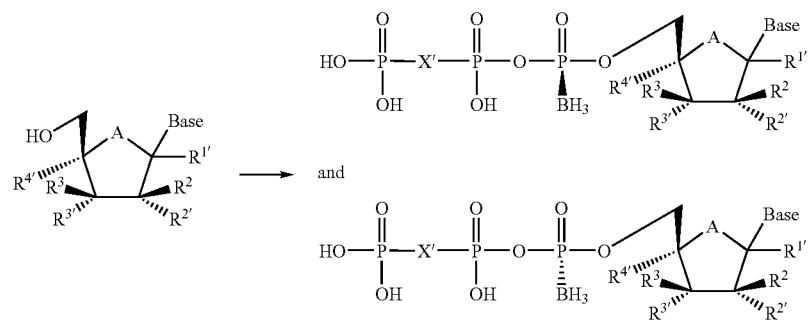

In Scheme C, preferably A is —, —CH$_2$—, or optionally protected —N—; R$^{1'}$, R$^2$, R$^{2'}$, R$^3$, R$^{3'}$, R$^{4'}$ are each independently —H, halogen, alkyl, —O-alkyl, —OH, optionally protected —O—, methyl, or —F; X' is —O—, —S—, —NH—, —CF$_2$—, —CHF—, —CClH—, —CBr$_2$—, or —CHBr—. Base is as described herein.

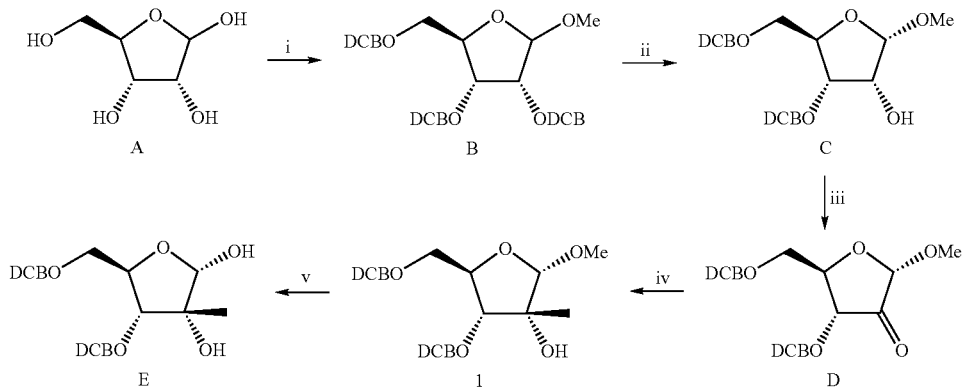

Scheme D

Compound 1 may be produced using methods generally known to those skilled in the art, such as the procedures described in Helv. Chim. Acta, vol. 78, p. 486 (1995) and in U.S. Pat. No. 6,777,395. Briefly, to Compound A, H$_2$SO$_4$ and MeOH were added and then chilled to 0-4° C. and NaH was added followed by DCBCl and DMF to render Compound B. To Compound B were added SnCl$_2$ and DCM, after which the mixture was chilled to 3° C. and distilled H$_2$O added to render Compound C. To Compound C was added Dess Martin periodinane followed by DCM to render Compound D. To Compound D was added MeMgBr and Et$_2$O and the mixture was raised from −75° C. to −10° C. to render Compound 1. To Compound 1, trifluoroacetic acid was added, followed by distilled H$_2$O and then the mixture was incubated at 60° C. for 8 h to render Compound E.

The compounds of the present disclosure may be tested for biological activity using well known procedures. For example, antiviral assays may be conducted according to published, widely used protocols. In order to obtain the therapeutic index, compound-induced cytotoxicity to host cells may also measured in parallel with antiviral activities. To determine the mode of action of antiviral nucleosides the corresponding nucleoside tri-phosphates may be subjected to enzyme-based assays for the inhibition of viral polymerases according to known protocols (Ranjith-Kumar et al. *J. Virol.* 2001, 75, 8615; Dhanak et al. *J. Biol. Chem.* 2002, 277, 38322-38327). Some compounds of the present disclosure showed K$_i$ values of less than 1 µM against HCV NS5B.

Since the replicon RNA replication mimics the replication of HCV RNA in infected hepatocytes, compounds that have the inhibitory effects in replicon assays are potentially useful as anti-HCV drugs. The HCV replicon-containing cell lines (Randall and Rice, *Current Opinion in Infectious Diseases* 2001, 14, 743) may be used for the identification of potential anti-HCV compounds. Among them is a widely used subgenomic replicon system developed by Lohmann et al. (*Science* 1999, 285, 110; *J. General Virol.* 2000, 81, 1631; *J. Virol.* 2001, 75, 1437, 2002, 76, 4008). Some compounds of the present disclosure showed potent anti-HCV activity with EC$_{50}$ values of low µM and below 1 µM.

Immortalized cell lines derived from hepatocytes, such as the Huh7 cells used in replicon-containing cell lines, are known to have diminished metabolic activity. Therefore the assessment of the intrahepatocyte levels of therapeutically active entities that are generated intracellularly by anabolic or catabolic processes requires assessment in primary hepatocytes. Some compounds of the present disclosure showed higher levels of intracellular triphosphate anabolite in primary hepatocytes compared with replicon-containing cells.

Widely used protocols developed by Korba et al. (*Antiviral Res.* 1992, 19, 55), and Pai et al. (*Antimicrobial Agents Chemother.* 1996, 40, 380) may be useful for the determination of in vitro anti-HBV activity.

Anti-HIV assays can be conducted according to the protocols developed by Schinazi et al. (*Antimicrobial Agents Chemother.* 1990, 34, 1061; 1992, 36, 2423; 1993, 37, 875) or other widely used protocols (Kimpton et al. *J. Virol.* 1992, 66, 2232; Chan et al. *J. Med. Chem.* 2001, 44, 1866). Illustrative nucleoside tri-phosphates of the present disclosure may act as potent inhibitors of the non-structural position 5B (NS5B), which is HCV's RNA-dependent RNA polymerase. Accordingly, such compounds may be suited to treat HCV and/or inhibit or prevent replication of HCV in a host. Also, compounds of the present disclosure may exhibit profiles of activity and may provide the artisan with an alternative to treating viruses that exhibit drug resistance to conventional drugs. Other compounds of the present disclosure may also reduce toxicity and tolerability levels relative to existing therapies and those in development, and/or improve pharmacokinetic properties.

Accordingly, nucleosides, nucleotide, nucleotide mimics, and/or their prodrugs of the present disclosure can be useful for the inhibition of a variety of enzymes including, but not limited to, DNA or RNA polymerases, helicases, ribonucleotide reductases, protein kinases, and telomerases and for the modulation of G-proteins, P2 purinergic receptors and the allosteric sites of a variety of enzymes. Illustratively, the nucleosides, nucleotides, nucleotide mimics and/or prodrugs of the present disclosure are used to treat viral infections caused by the RNA viruses of the group Flaviviridae and, in particular, HCV.

Also, the nucleosides, nucleotide mimics and/or their prodrugs and derivatives thereof that display cytotoxicity to fast-dividing cancer cells may be useful for the treatment of proliferative disorders, including, but not limited to, lung cancer, liver cancer, prostate cancer, colon cancer, breast cancer, ovarian cancer, melanoma, and leukemia.

As the ligands of P2 receptors and G-proteins, as well as the inhibitors of protein kinases, the nucleosides, nucleotides, nucleotide mimics and/or their prodrugs of the present disclosure may also be useful for the treatment of a wide range of other diseases and disorders such as inflammatory diseases, autoimmune diseases, Type 2 diabetes, and cardiovascular diseases.

To address the issue of drug resistance, combination therapies are widely used in the treatment of infectious diseases and/or proliferative disorders. One or more nucleosides, nucleotides, nucleotide mimics, prodrugs, and/or pharmaceutically-acceptable salts, esters, solvates, hydrates and prodrugs of the present disclosure may also be therapeutically administered as a single formulation, such as a single tablet or a solution for injection, with one or more chemical entities, or alternatively may be administered in separate formulations in combination with one or more other active chemical entities, to form a combination therapy. The other active chemical entities may include a small molecule, a polypeptide, and/or a polynucleotide, and combinations, salts, esters, solvates, hydrates and prodrugs and/or other derivatives thereof. When administered as separate formulations, the individual compounds may be co-administered at substantially the same time, for example, administering two individual tablets, or administered separately at different times and/or at different frequencies. Illustratively, the dose administered to a host for each compound is generally determined by the desired blood level concentration of drug over a predetermined amount of time to achieve a therapeutic affect in the host, as know in the art and further described herein. For instance, compounds of this disclosure may be useful when used in combination with other agents known to exert antiviral and/or antiproliferative effect. For example, combination with immunomodulatory/antiviral agents such as an interferon and/or an interferon derivative such as interferon alpha 2B (such as Intron® A interferon available from Schering Corp., Kenilworth, N.J.), pegylated interferon alpha 2A (such as Pegasys® available from Hoffmann-LaRoche, Nutley, N.J.), pegylated interferon alpha 2B (such as Peg-Intron™ available from Schering Corp., Kenilworth, N.J.), consensus interferon (such as interferon alphacon-1, or Infergen® available from Valeant Pharmaceuticals, Costa Mesa, Calif.), interferon alpha 2A, recombinant interferon alpha 2A (such as Roferon interferon available from Hoffmann-LaRoche, Nutley, N.J.), or lymphoblastoid interferon tau, and other large or small molecules known to modulate host immune responses may be beneficial in the treatment of a viral infection.

Similarly, combinations of compounds of this disclosure with inosine mono-phosphate dehydrogenase (IMPDH) inhibitors, antiviral nucleosides, and/or antiviral non-nucleosides could augment the activity of the nucleosides or nucleotides disclosed herein when administered alone. Other illustrative combinations useful in present disclosure include combinations with, for example, a cyclosporine such as, cyclosporin A; a cytokine, such as, interleukin 2, interleukin 6, or interleukin 12; a type 1 helper T cell response enhancer; interfering RNA; anti-sense RNA; an imidazoquinolone, such as resimiquimod or Imiqimod; an inosine 5'-monophosphate dehydrogenase inhibitor; ribavirin; amantadine; rimantadine; and/or a metalloprotease, serine protease, polymerase, or a helicase inhibitory agent; and combinations thereof. In one embodiment, one or more compounds of the present disclosure are used in combination with one or more compounds having anti-HCV activity including, for example, a HCV helicase inhibitor, a HCV metalloprotease inhibitor, a HCV polymerase inhibitor, a HCV NS4B protein inhibitor, a HCV NS5A protein inhibitor, a HCV serine protease inhibitor, and/or a HCV entry, assembly, or egress protein inhibitor.

The present disclosure also relates to kits or packages adapted for administration of the particular dosage regimen, to ease mixing and/or administration of a composition disclosed herein. Illustratively, a month's supply of tablets can be packaged in a tablet dispenser such as a DIALPAK® tablet dispenser supplied by Ortho, Inc., which contains a dial member at the center of a circle that points to a day of the week so that when a pill is removed from the dispenser, the dial can be rotated so that it points to the next day of the week. This design is intended to avoid the inadvertent taking of two pills in one day and is also designed to let the owner of the device know when a day has been skipped. A further illustration includes supplying a month's supply of powder that is packaged with a separate month's supply of diluent and a re-usable plastic dosing cup. One skilled in the art will appreciate that such kits may contain many different variations of the above components, such as, for example, kits that are packaged in a unit dose form or as daily, weekly or yearly kits.

Another aspect of the present disclosure is a method of inhibiting the function of the HCV replicon by contacting the HCV replicon with a compound of formula I or a pharmaceutically-acceptable salt, ester, solvate, hydrate or prodrug thereof.

Based upon the proceeding schemes and/or procedures and the following Examples, substituted pyrrolo-triazines attached to a sugar moiety can be prepared by one skilled in the art using similar methods, as shown in Table Nos. 1 and 2.

TABLE No. 1

Substitutions of the glycosyl 4-amino pyrrolol-triazine, where R'', R''', and R'''', may be independently selected.

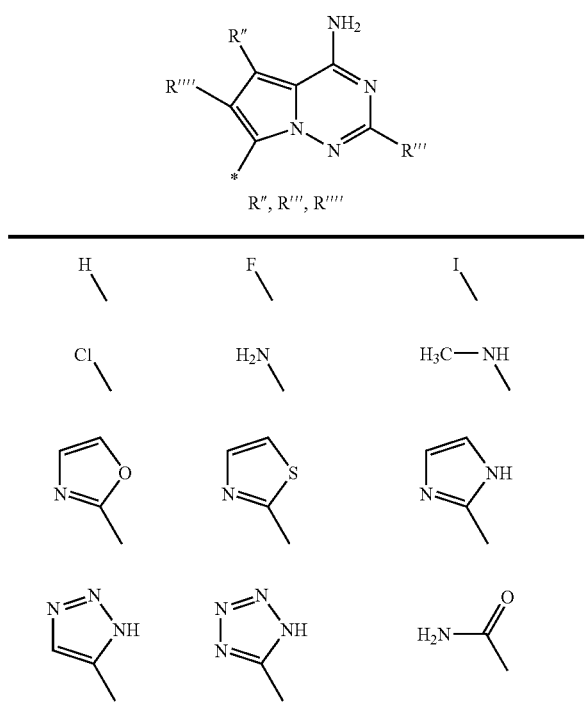

R'', R''', R''''

TABLE No. 1-continued

Substitutions of the glycosyl 4-amino pyrrolol-triazine, where R", R"', and R"" may be independently selected.

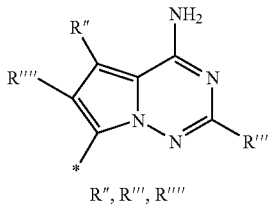

R", R"', R""

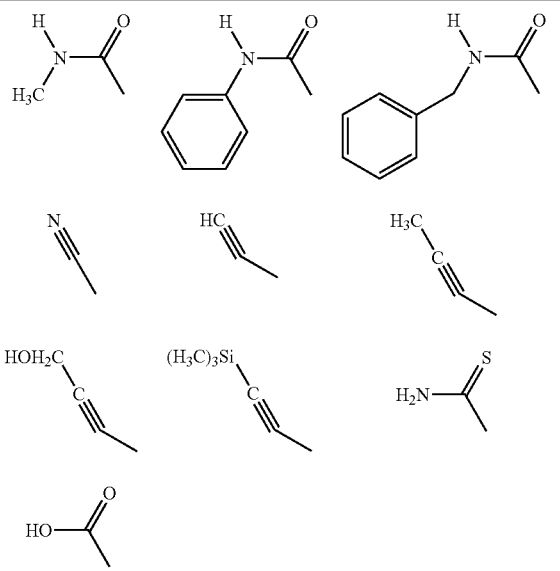

TABLE No. 2

Substitutions of the glycosyl 4-keto pyrrolol-triazine, where R", R"', and R"" may be independently selected.

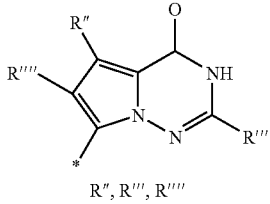

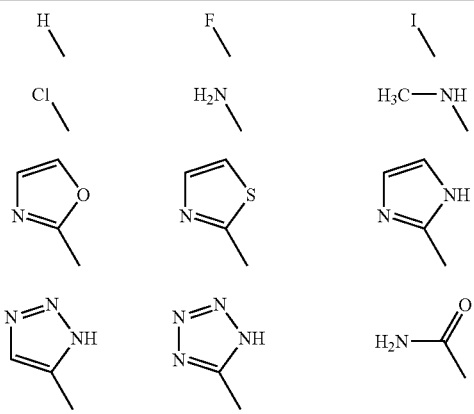

TABLE No. 2-continued

Substitutions of the glycosyl 4-keto pyrrolol-triazine, where R", R"', and R""may be independently selected.

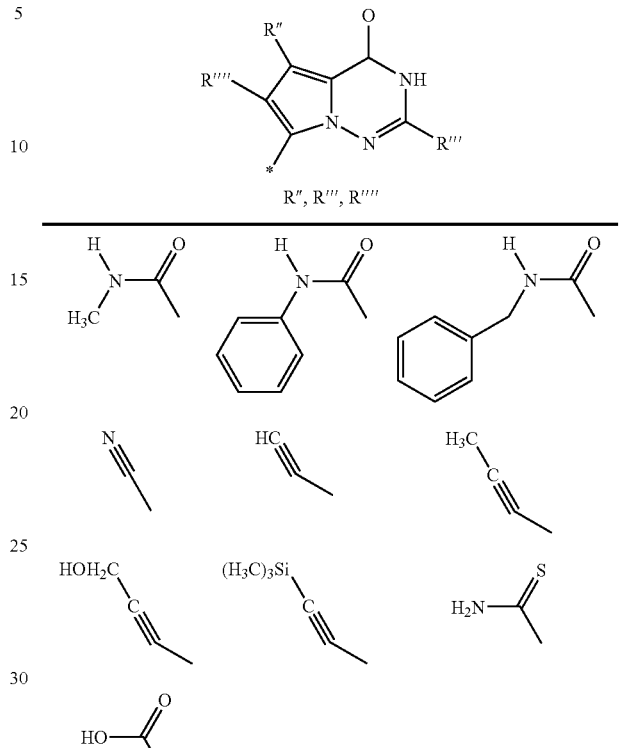

Abbreviations that may be used herein including the Schemes and the experimental section are as follows unless indicated otherwise:

Ar: argon
Bn: benzyl
Bu: n-butyl
Bz: benzoyl
DCB: 2,4-dichlorobenzyl
DCM: dichloromethane
DIEA: diisopropylethylamine
DMF: dimethylformamide
DMSO: dimethyl sulfoxide
ESI: electrospray ionization
Et: ethyl
EtOAc: ethyl acetate
HPLC: high performance liquid chromatography
Me: methyl
MeOH: methyl alcohol
MS: mass spectrometry
NMR: nuclear magnetic resonance
Ph: phenyl
RT: room temperature
TEA: triethylamine
TFA: trifluoroacetic acid
THF: tetrahydrofuran The following non-limiting examples are put forth to provide those of ordinary skill in the art with a complete disclosure and description of how to prepare and use the compounds disclosed herein. The following specific embodiments are representative compounds of formula (1), and are therefore,

Example 1

Preparation of 4-amino-7-(2-C-methyl-β-D-ribofuranosyl)-pyrrolo[2,1-f][1,2,4]triazine (Compound 9)

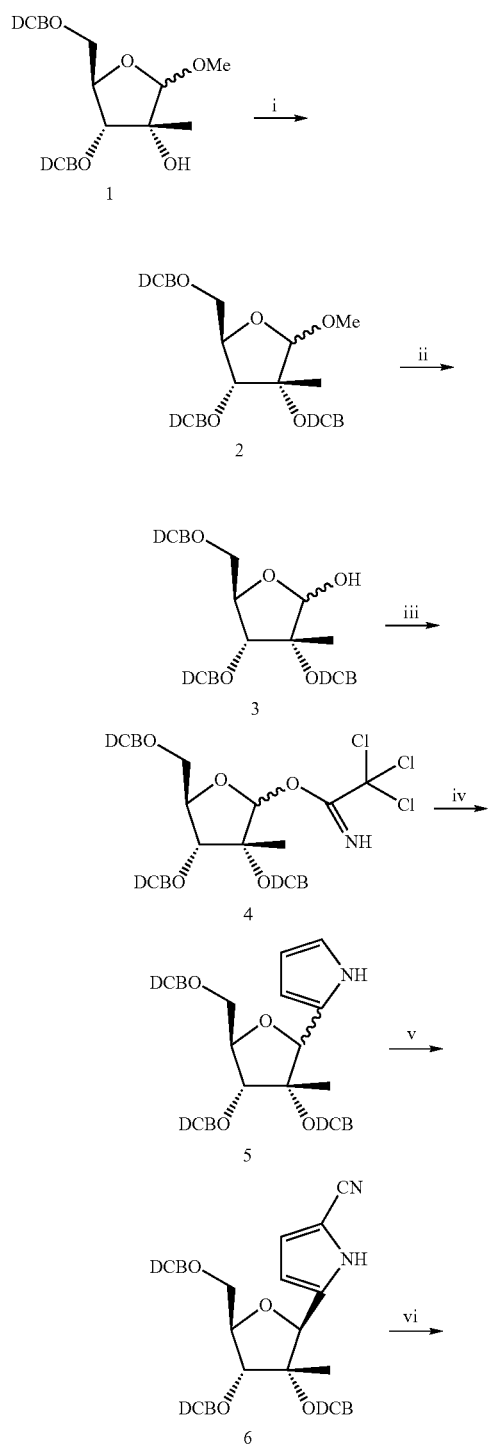

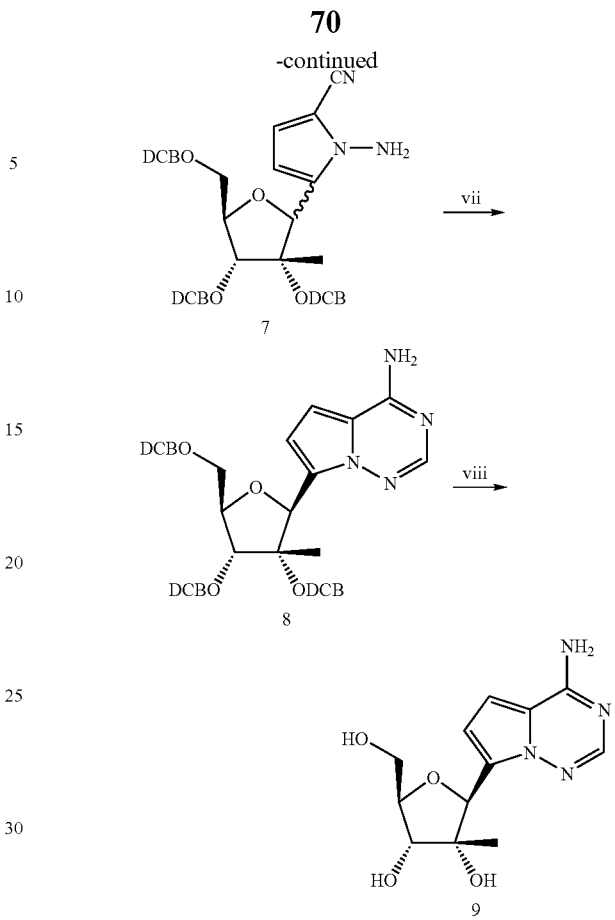

Step i: Compound 1,3,5-bis-O-(2,4-dichlorophenylmethyl)-1-O-methyl-2-C-methyl-D-ribofuranose (19.2 g) in anhydrous THF (200 mL) was chilled to 0° C. under Ar in an ice:water bath then treated with NaH (60% dispersion in oil, 2.6 g) in 4 batches at 10 min intervals. The suspension was warmed to RT then treated dropwise with 2,4-dichlorobenzyl chloride (11.2 mL). The reaction was then heated to 70° C. under Ar for 16-24 h. The cooled reaction mixture was filtered, and the filtrate was eluted on silica with 10-30% EtOAc:hexane to form Compound 2 as a mixture of α and β anomers (16.68 g): $^1$H NMR (CDCl$_3$) major anomer: δ 1.42 (s, 3H); 3.46 (s, 3H); 3.64 (d, 1H, J=4.8 Hz); 3.73 (dd, 1H, J=3.9, 10.7 Hz); 3.67 (dd, 1H, J=4.4, 10.7 Hz); 4.29 (q, 1H, J=4.3 Hz); 4.56-4.85 (m, 7H); 7.11-7.25 (m, 3H, J=2.0, 8.4 Hz); 7.31-7.41 (m, 5H); 7.58 (d, 1H, J=8.4 Hz).

Step ii: Compound 2 (6.91 g) in TFA (70 mL) was chilled to 0° C. then treated dropwise with water (7 mL). The mixture was warmed to RT then stirred for 4 h. The resulting solution was concentrated to 10 mL and added slowly to a 50:50 mixture of Et$_2$O:sat. NaHCO$_3$ (aq) (80 mL total). The mixture was neutralized with NaHCO$_3$ (aq), and the aqueous layer was extracted with ether (2×50 mL), and then the combined organic extracts were washed with NaHCO$_3$ (aq). The organic extract was dried (MgSO$_4$), filtered, and concentrated in vacuo. The crude material was eluted on a silica column with 5-40% EtOAc:hexane to afford Compound 3 (5.2 g) as a mixture of α and β anomers: $^1$H NMR (d$_6$-acetone) both anomers: δ 1.52 (s, 6H); 3.79 (t, 4H, J=4.8 Hz); 3.99 (d, 1H, J=5.6 Hz); 4.10 (d, 1H, J=7.3 Hz); 4.21-4.27 (m, 1H); 4.37 (dd, 1H, J=4.5, 10.0 Hz); 4.62-4.95 (m, 12H); 5.10 (d, 1H, J=9.1 Hz); 5.20 (d, 1H, J=4.6 Hz); 5.57 (d, 1H, J=4.8 Hz); 5.62 (s, 1H); 7.25-7.70 (m, 18H).

Step iii: Compound 3 (5.52 g) in anhydrous DCM (40 mL) under Ar was treated with trichloroacetonitrile (1.95 mL) and $Cs_2CO_3$ (254 mg) and stirred at RT for 3 h. The solution was diluted with DCM (50 mL), washed with water (100 mL), and the aqueous layer extracted with DCM (2×50 mL). The combined organic extracts were washed with brine (100 mL), dried ($MgSO_4$), filtered, and concentrated. The resulting residue was eluted through a silica column with 15% EtOAc:hexane to give the target compound Compound 4 (5.58 g) as a mixture of α and β anomers: $^1H$ NMR ($CDCl_3$) major anomers: δ 1.56 (s, 3H); 3.71 (dd, 1H, J=4.8, 10.8 Hz); 3.80 (dd, 1H, J=4.0, 10.8 Hz); 4.15 (d, 1H, J=8.1 Hz); 4.42-4.91 (m, 7H); 6.25 (s, 1H); 7.15-7.53 (m, 9H); 8.55 (s, 1H).

Step iv: Compound 4 (5.0 g) in anhydrous DCM (200 mL) was treated with powdered 4 Å molecular sieves under Ar for 2 h. The solution was then chilled to −70° C. (internal temperature), treated with freshly distilled pyrrole (1.46 mL) then dropwise with $BF_3$—$OEt_2$ (2.76 mL). The mixture was stirred for 40 min, while maintaining the internal temperature below −55° C. The mixture was then cooled to −70° C. and treated with 7 M $NH_3$ in methanol (20 mL) before being warmed to RT. The mixture was diluted with DCM and washed with water. The organic extract was dried ($MgSO_4$), filtered, and concentrated in vacuo to give a grey gum. The crude material was applied to a silica flash column and eluted with 15% EtOAc:hexane to afford the pyrrole nucleoside Compound 5 (2.72 g) as a mixture of α: β anomers in a ratio of about 2:3: $^1H$ NMR ($CDCl_3$) β-anomer only: δ 9.53 (br s, 1H), 7.60-7.14 (m, 9H), 6.36-6.35 (m, 1H), 6.11-6.10 (m, 1H), 6.04 (br s, 1H), 5.13 (s, 1H), 4.89-4.61 (m, 6H), 4.37-4.36 (m, 1H), 4.21 (d, J 8.4 Hz, 1H), 4.10 (dd, J 2.6 Hz, 10.5 Hz, 1H), 3.85 (dd, J 1.9 Hz, 10.5 Hz, 1H), 1.16 (s, 3H).

Step v: Compound 5 (1.37 g, mixture of anomers) was suspended in anhydrous acetonitrile (6 mL). Anhydrous DMF was added until a homogeneous solution was observed (~1.0 mL), and the solution was chilled under Ar in an ice:acetone bath to −12° C. After 10 min, the solution was treated dropwise with chlorosulphonyl isocyanate (0.17 mL), and the resulting mixture was stirred below 0° C. for 45 min, during which time a dark red colour was observed. The mixture was poured onto ice (100 g), diluted with EtOAc (100 mL), and stirred until the ice melted. The organic extract was dried ($MgSO_4$), filtered, and concentrated in vacuo to give a dark pink oil. The crude material was suspended in 20 mL 50:50 DCM:hexane, applied to a silica flash column, and eluted with 15-50% EtOAc:hexane to render Compound 6 as the β-anomer (0.69 g) with the corresponding α-anomer (0.28 g) collected separately: $^1H$ NMR ($CDCl_3$) β-anomer: δ 10.44 (s, 1H), 7.53 (d, J 8.3 Hz, 1H), 7.47 (d, J 2.0 Hz, 1H), 7.42-7.37 (m, 3H), 7.32-7.21 (m, 4H), 6.79 (dd, J 2.6, 3.8 Hz, 1H), 6.10 (dd, J 2.6 Hz, 3.5 Hz, 1H), 5.11 (s, 1H), 4.90 (d, J 12.5 Hz, 1H), 4.85 (d, J 13.1 Hz, 1H), 4.74 (d, J 13.1 Hz, 1H), 4.73 (d, J 12.5 Hz, 1H), 4.68 (d, J 12.4 Hz, 1H), 4.59 (d, J 12.4 Hz, 1H), 4.35 (ddd, J 1.9 Hz, 2.4 Hz, 8.4 Hz, 1H), 4.13 (d, J 8.4 Hz, 1H), 4.05 (dd, J 2.8 Hz, 10.6 Hz, 1H), 3.76 (dd, J 1.7 Hz, 10.6 Hz, 1H), 1.20 (3H, s).

Step vi: NaH (72.5 mg) in dry THF (13 mL) was cooled to −5° C. for 10 min. Compound 6 (0.6 g, β-anomer) in THF (2 mL) was added dropwise followed by portionwise addition of $Ph_2P(O)ONH_2$ (0.39 g) before stirring at 0° C. for 30 min. The mixture was partitioned between toluene and water, and the organic extracts were collected, dried ($MgSO_4$), filtered, and concentrated in vacuo. The product was stored in the freezer and used in subsequent reactions without further purification: $^1H$ NMR ($d_6$-DMSO): δ 7.63 (br d, J 1.9 Hz, 1H), 7.58-7.54 (m, 4H), 7.45-7.33 (m, 4H), 6.76 (d, J 4.4 Hz, 1H), 6.14 (d, J 4.4 Hz, 1H), 6.13 (br s, 2H), 5.36 (s, 1H), 4.76-4.62 (m, 6H), 4.22-4.19 (m, 1H), 4.0 (d, J 7.0 Hz, 1H), 3.83 (dd, J 3.5 Hz, 10.9 Hz, 1H), 3.76 (dd, J 4.4 Hz, 10.9 Hz, 1H), 1.15 (s, 3H).

Step vii: to a solution of Compound 7 (60 mg) in anhydrous DMA (2 mL) was added formamidine acetate (700 mg), and the suspension heated under Ar at 140° C. for 1.5 h. The mixture was cooled to RT and more formamidine acetate (700 mg) was added, and the mixture was heated for another 1.5 h at 140° C. The mixture was cooled to RT overnight, whereupon precipitation occurred. The supernatant was removed, and the precipitate washed with DCM. The supernatant and combined washings were concentrated in vacuo. Residual DMA was distilled off (Kugelrohr), and the residue taken up in DCM (5 mL), washed with water (1 mL), dried with $MgSO_4$, filtered, and concentrated. Residual DMA was removed by distillation, and the residue was purified on flash silica gel (50% EtOAc in hexane) to afford Compound 8 (32 mg) as a colourless syrup: $^1H$ NMR ($CDCl_3$): δ 7.89 (s, 1H), 7.61 (d, J 8.3 Hz, 1H), 7.46 (d, J 8.3 Hz, 1H), 7.38-7.19 (m, 6H), 7.15 (dd, J 2.1 Hz, 8.3 Hz, 1H), 6.82 (d, J 4.5 Hz, 1H), 6.56 (d, J 4.5 Hz, 1H), 5.88 (s, 1H), 5.76 (br s, 2H), 4.86 (s, 2H), 4.72 (s, 2H), 4.73-4.62 (m, 2H), 4.40-4.35 (m, 1H), 4.09 (d, J 8.3 Hz, 1H), 3.97 (dd, J 2.7 Hz, 10.9 Hz, 1H), 3.81 (dd, J 3.7 Hz, 10.8 Hz, 1H), 1.14 (s, 3H); $^{13}C$ NMR ($CDCl_3$): δ 155.47, 147.18, 136.17, 134.65, 134.60, 134.25, 134.10, 133.79, 133.54, 133.30, 132.66, 130.42, 130.24, 130.17, 129.72, 129.39, 129.24, 128.84, 127.29, 127.26, 127.20, 114.43, 110.86, 100.48, 85.06, 83.76, 79.43, 78.67, 70.22, 70.19, 70.10, 62.88, 18.00.

Step viii: to a solution of Compound 8 (240 mg) in dry methanol (30 mL) was added, with stirring, anhydrous sodium acetate (192 mg) and glacial acetic acid (670 μL). The mixture was degassed, purged with Ar, and 10% Palladium on charcoal was added (150 mg). The mixture was stirred at 45° C. under $H_2$ for 66 h. The reaction mixture was degassed, purged with Ar, filtered through a pad of celite with MeOH, and concentrated to obtain the crude product. Column chromatography on flash silica gel (17% MeOH in EtOAc) rendered Compound 9 (70.7 mg). ESI-MS m/z 281 ([M+H]$^+$); $^1H$ NMR ($d_6$-DMSO) δ 7.81 (s, 1H), 7.61 (br s, 2H), 6.84 (d, J 4.4 Hz, 1H), 6.70 (d, J 4.4 Hz, 1H), 5.39 (s, 1H), 4.90 (br s, 1H), 4.75 (br t, J 5.4 Hz, 1H), 4.66 (s, 1H), 3.78-3.55 (m, 3H), 3.62-3.55 (m, 1H), 0.78 (s, 3H).

Example 2

Preparation of 4-amino-5-fluoro-7-(2-C-methyl-β-D-ribofuranosyl)-pyrrolo[2,1-f][1,2,4]triazine (Compound 11)

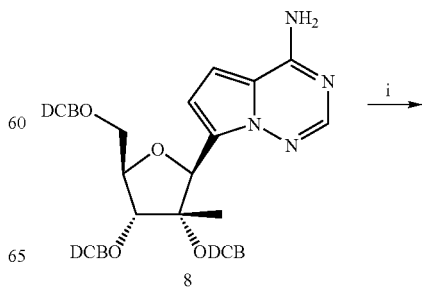

8

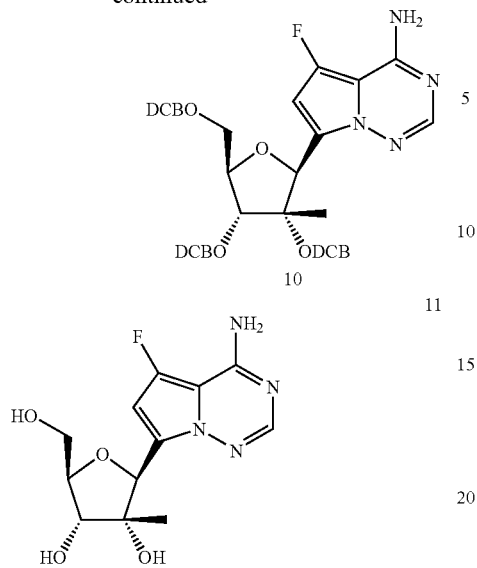

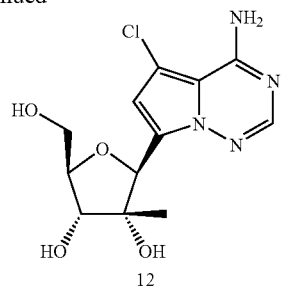

Step i: to a suspension of Compound 8 (0.11 g) in acetonitrile (2 mL) was added Selectfluor™ (1-Chloromethyl-4-fluoro-1,4-diazoniabicyclo[2.2.2]octane bis(tetrafluoroborate) (80 mg), and the mixture was stirred and sonicated at RT for 5 min. The tube was sealed and heated in a microwave reactor at 82° C. for 15 min. The solvent was removed in vacuo to render a dark brown gum. The crude product (Compound 10) was suspended in 2 mL DCM and applied to a silica flash column and eluted with 12% EtOAc/hexane to afford the product as a pale brown foam (30 mg): $^1$H NMR (CDCl$_3$): δ 7.79 (s, 1H), 7.61 (d, J 8.4 Hz, 1H), 7.45 (d, J 8.2 Hz, 1H), 7.45 (d, J 8.2 Hz, 1H), 7.41 (d, J 2.1 Hz, 1H), 7.37-7.34 (m, 3H), 7.27-7.17 (m, 3H), 6.60 (s, 1H), 5.85 (s, 1H), 4.87 (s, 2H), 4.72 (s, 2H), 4.69 (q, J 12.6 Hz, 2H), 4.36 (td, J 8.5 Hz, 2.9 Hz, 1H), 4.07 (d, J 8.5 Hz, 1H), 3.97 (dd, J 2.5 Hz, 10.9 Hz, 1H), 3.79 (dd, J 3.2 Hz, 10.9 Hz, 1H), 1.16 (s, 3H).

Step ii: to a stirred suspension of Compound 10 (50 mg) in anhydrous methanol (4 mL) was added sodium acetate (60 mg) and 10% Pd/C (40 mg). The mixture was hydrogenated at 45° C. for 16 h. The mixture was filtered to remove the catalyst and the filtrate was concentrated in vacuo. The crude material was purified by column chromatography (5% MeOH/CH$_2$Cl$_2$) to afford Compound 10 (5.1 mg): ESI-MS m/z ([M+H]$^+$) 299.16; $^1$H NMR (d$_6$-DMSO): δ 7.73 (s, 1H), 6.66 (s, 1H), 5.37 (s, 1H), 3.74-3.69 (m, 3H), 3.60-3.57 (m, 1H), 0.80 (s, 3H).

Example 3

Preparation of 4-amino-5-chloro-7-(2-C-methyl-β-D-ribofuranosyl)-pyrrolo[2,1-f][1,2,4]triazine (Compound 12)

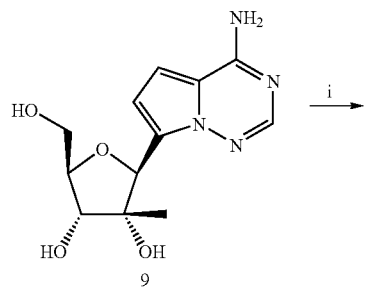

Step i: Compound 9 (52 mg) in anhydrous DMF (2 mL) under Ar was chilled to 0° C. and treated dropwise with a solution of N-chlorosuccinimide in anhydrous DMF (27 mg in 1 mL). The mixture was warmed to RT and stirred for 1 h. The mixture was concentrated then eluted through a silica column with 0-10% MeOH:EtOAc to give Compound 12 (5.3 mg): ESI-MS m/z 407.1 ([M+H]$^+$); $^1$H NMR (d$_6$-DMSO): δ 0.83 (s, 3H); 3.60 (m, 1H); 3.70-3.74 (m, 4H); 4.74 (s, 1H); 4.84 (t, 1H, J=5.0 Hz); 4.91 (d, 1H, J=6.4 Hz); 5.36 (s, 1H); 6.86 (s, 1H); 7.83 (s, 1H).

Example 4

Preparation of 4-amino-5-iodo-(2-C-methyl-β-D-ribofuranosyl)-pyrrolo[2,1-f][1,2,4]triazine (Compound 13)

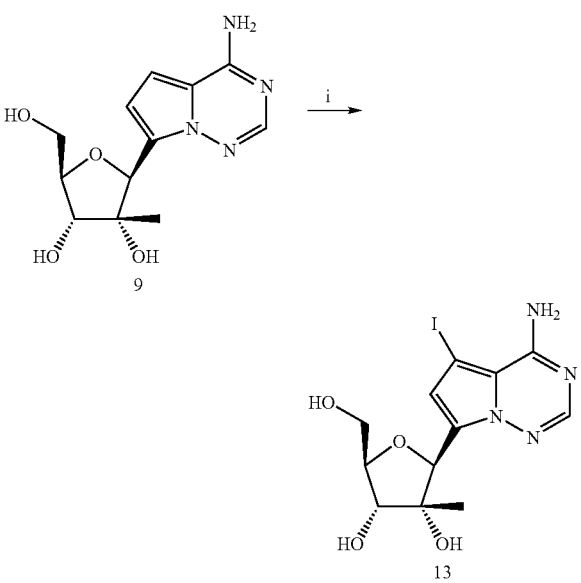

Step i: to a solution of Compound 9 (5.2 mg) in anhydrous DMF (0.5 mL) was added at RT N-iodosuccinimide (4.7 mg), and the mixture was stirred in the dark at RT and under Ar for 4 d. Saturated sodium thiosulfate solution was added (4 drops), and the resulting mixture was extracted with EtOAc (3×1 mL). The organic phase was concentrated and freeze-dried. The resulting residue was suspended in a small amount of MeOH and purified on flash silica gel twice (elution gradient EtOAc to 5% MeOH in EtOAc) to afford Compound 13 as a colorless solid (1.5 mg): ESI-MS m/z 407 ([M+H]$^+$); $^1$H NMR (300 MHz, d$_6$-DMSO): $^1$H NMR (300 MHz, d$_6$-DMSO): δ 7.87 (s, 1H), 7.34 (br s, 2H), 7.01 (s, 1H), 5.35 (s, 1H), 4.91 (br s, 1H), 4.82 (t, J 5.1 Hz, 1H), 4.72 (s, 1H), 3.77-3.66 (m, 3H), 3.61-3.54 (m, 1H), 0.79 (s, 3H).

Example 5

Preparation of 4-amino-7-(2-C-methyl-β-D-ribofuranosyl)-pyrrolo[2,1-f][1,2,4]triazine-5-carbonitrile (Compound 14)

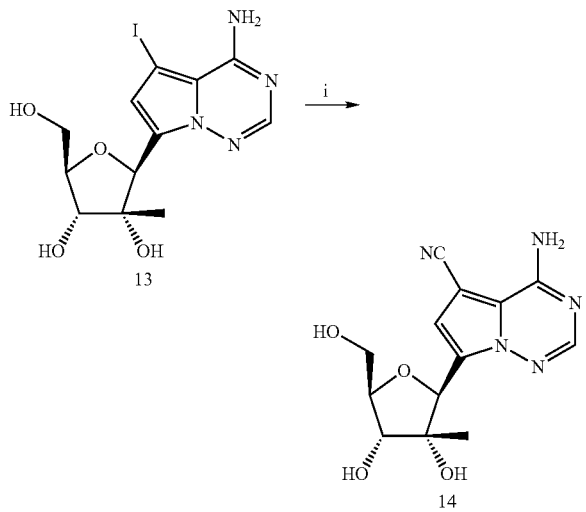

Step i: a solution of Compound 13 (20 mg) in anhydrous DMA (0.7 mL) was evacuated and purged with Ar (three times). Zinc powder (1 mg), bis(tri-tert-butylphosphine)palladium(0) (3.2 mg) and zinc cyanide (18 mg) were added, and the mixture was heated at 150° C. and under Ar with stirring for 1 h. The mixture was cooled to RT and solid phase bound triphenylphosphine (PS-TPP, previously washed with DMA, 60 mg) was added, and the resulting mixture was stirred at RT under Ar for 21 h. The mixture was filtered through celite and washed with EtOH. The filtrate was concentrated, and residual DMA was removed by distillation (Kugelrohr) to render 25 mg of an oil. This material was purified twice on flash silica gel eluting with 5% MeOH in EtOAc to afford the product as pale yellow solid (4 mg). This material was boiled briefly in 2 mL MeOH with 1 mg activated charcoal to afford Compound 14 (2.5 mg) as a colourless solid: ESI-MS m/z 306 ([M+H]$^+$); $^1$H NMR (300 MHz, d$_6$-DMSO): δ 8.11 (s, 1H), 7.58 (br s, 2H), 7.35 (s, 1H), 5.37 (s, 1H), 4.95 (d, J 6.5 Hz, 1H), 4.86 (t, J 4.8 Hz, 1H), 4.80 (s, 1H), 3.80-3.69 (m, 3H), 3.64-3.57 (m, 1H), 0.81 (s, 3H).

Example 6

Preparation of 4-amino-7-(2-C-methyl-β-D-ribofuranosyl)-pyrrolo[2,1-f][1,2,4]triazine-5-carboxylic acid amide (Compound 15)

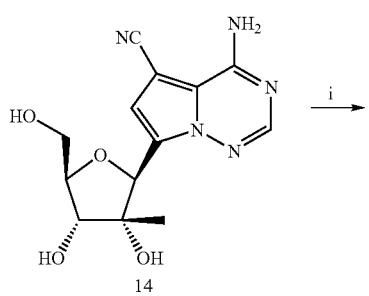

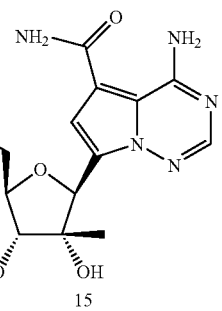

Step i: to a solution of Compound 14 (12 mg) in ethanol (4.8 mL) was added 0.7 mL 28% aqueous ammonia and 0.18 mL 30% hydrogen peroxide. The mixture was stirred in a sealed vial at RT for 19 h. The solvent was removed in vacuo, and the crude product was purified on flash silica gel eluting with 10% MeOH in EtOAc to afford the product as pale yellow solid (9.1 mg). This material was recrystallised from EtOAc/MeOH to afford Compound 15 (6.5 mg) as a colourless solid: ESI-MS m/z 324 ([M+H]$^+$); $^1$H NMR (500 MHz, d$_6$-DMSO): δ 10.38 (d, J 3.1 Hz, 1H), 8.07 (br s, 1H), 8.04 (d, J 3.1 Hz, 1H), 7.91 (s, 1H), 7.52 (br s, 1H), 7.23 (s, 1H), 5.39 (s, 1H), 4.98 (d, J 7.4 Hz, 1H), 4.74 (s, 1H), 4.64 (t, J 5.8 Hz, 1H), 3.82-3.73 (m, 2H), 3.71-3.66 (m, 1H), 3.55 (dd, J 7.1 Hz, 8.3 Hz, 1H), 0.82 (s, 3H).

Example 7

Preparation of 4-amino-5-trimethylsilanylethynyl-7-(2-C-methyl-β-D-ribofuranosyl)-pyrrolo[2,1-f][1,2,4]triazine (Compound 16)

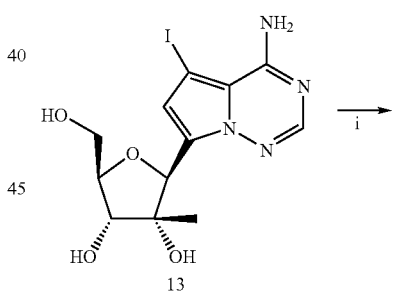

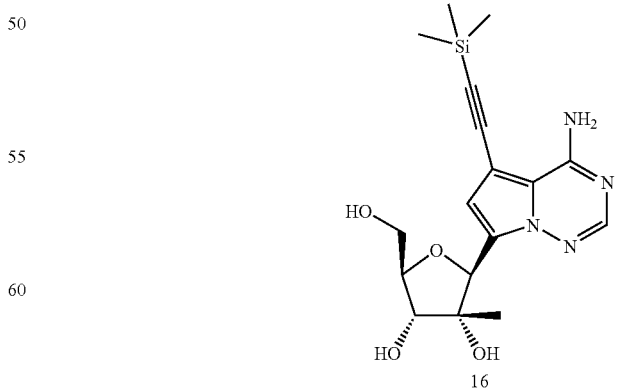

Step i: to a solution of Compound 13 (43 mg, 0.11 mmol), triethylamine (32 μL, 0.42 mmol) and (trimethylsilyl)acetylene (0.12 mL, 1.1 mmol) were stirred in anhydrous DMF (0.40 mL) under Ar for 5 min, then CuI (5.2 mg, 27 μmol) and PdCl$_2$(PPh$_3$)$_2$ (8.1 mg, 12 μmol) were added, and the resulting mixture stirred at RT for 2 h. The reaction mixture was filtered, concentrated in vacuo, and purified by reverse-phase LCMS, affording Compound 16 (10 mg, 26%) as a beige solid: ESI-MS m/z 377.2 ([M+H]$^+$) $^1$H NMR (d$_6$-DMSO) δ 7.94 (s, 1H), 6.96 (s, 1H), 5.33 (s, 1H), 3.76-3.55 (m, 4H), 0.79 (s, 3H), 0.24 (s, 9H).

Example 8

Preparation of 4-Amino-5-ethynyl-7-(2-C-methyl-β-D-ribofuranosyl)-pyrrolo[2,1-f][1,2,4]triazine (Compound 17)

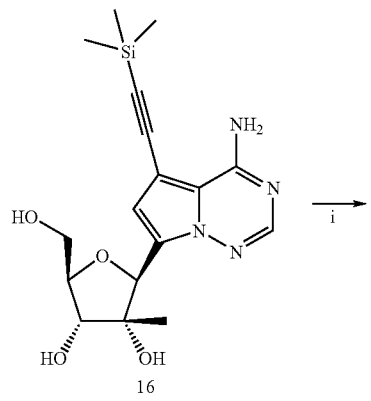

Step i: a solution of Compound 16 (2.0 mg, 5.3 μmol) in methanol (0.20 mL) was stirred with MP-carbonate (2.9 mmol/g, 18 mg, 53 μpmol) for 30 min. The solution was decanted from the resin and concentrated in vacuo, affording rendering Compound 17 (0.45 mg, 28%) as a white solid: ESI-MS m/z 305.2 ([M+H]$^+$); $^1$H NMR (d$_6$-DMSO) δ 7.92 (s, 1H), 6.97 (s, 1H), 5.35 (s, 1H), 4.91-4.73 (m, 3H), 4.38 (s, 1H), 3.76-3.57 (m, 4H), 0.80 (s, 3H).

Example 9

Preparation of 4-amino-5-carboxylic acid-7-(2-C-methyl-β-D-ribofuranosyl)-pyrrolo[2,1-f][1,2,4]triazine (Compound 18)

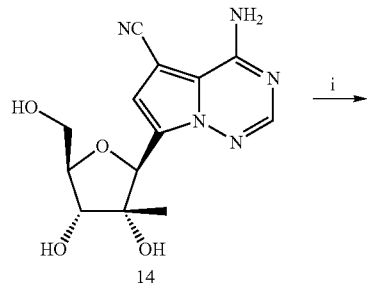

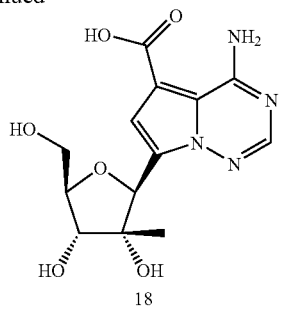

To a solution of Compound 14 (3.5 mg) in methanol (1 mL) was added an aqueous solution of 5 M NaOH, and the mixture was heated at 70° C. for 5 h. After cooling to RT, the solution was neutralized by addition of an aqueous solution 5 M hydrochloric acid. The aqueous mixture was lyophilized to leave a white solid. Methanol (5 mL) was added to the flask, and the suspension was filtered. The filtrate was concentrated in vacuo to leave a white film (3 mg). Purification by preparative reverse phase HPLC provided Compound 18 as a white solid (1 mg). ESI-MS m/z 325 ([M+H]$^+$).

Example 10

Preparation of 2,4-diamino-7-(2-C-methyl-β-D-ribofuranosyl)-pyrrolo[2,1-f][1,2,4]triazine (Compound 20)

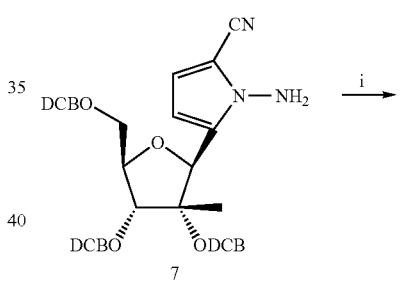

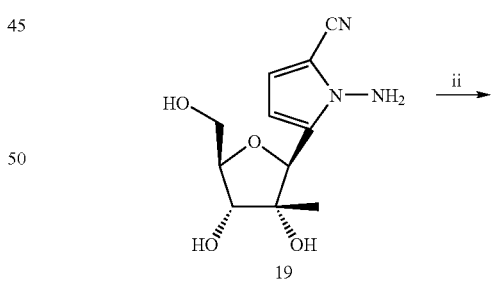

Step i: to a solution of Compound 7 (50 mg, 0.07 mmol) in DCM (3 ml) under Ar was cooled to −78° C. whereupon a solution of 1.0 M boron trichloride in DCM (900 μL, 0.9 mmol) was added dropwise over 5 min. The resulting brownish/red solution was then stirred at −78° C. to −70° C. for 3 h and allowed to warm gradually to 0° C. over 3 h and left for 20 h at 0° C. A further aliquot of 1.0 M boron trichloride in DCM (100 uL, 0.1 mmol) was added and the reaction mixture warmed to RT and stirred for 4 d whereupon a solution of DCM:methanol (5 ml, 1:1 v/v) was added. After 30 min, the reaction mixture was filtered and evaporated to dryness. The crude material was dissolved in EtOAc (2 ml) with methanol (2 drops to aid dissolution) and purified by column chromatography on Silica eluting with 0-15% MeOH/EtOAc. The fractions containing the product (as indicated by LCMS) were combined and evaporated to dryness to afford Compound 19, which, owing to its instability, was used immediately in the subsequent reaction.

Step ii: to the solution of partially purified Compound 19 in anhydrous ethanol (3 ml) under Ar was added guanidine carbonate (150 mg, 2.0 mmol) followed by triethylamine (100 μl, 0.726 mmol). The suspension was heated in a microwave reactor for 2 h at 160° C., whereupon the reaction mixture was filtered and evaporated to dryness. The crude material was suspended in water (3 ml) and methanol (3 drops) and purified by reverse phase preparative HPLC. The appropriate fractions were combined and lyophilised to give Compound 20 as a white solid as (3 mg): ESI-MS m/z 296.06 ([M+H]$^+$); $^1$H NMR (D3-CH$_3$CN): 0.92 (s, 3H), 3.86 (m, 4H), 5.22 (s, 1H), 6.61 (d, 1H), 6.94 (d, 1H).

Example 11

Preparation of 4-amino-7-(2-C-methyl-β-D-ribofuranosyl)-pyrrolo[2,1-f][1,2,4]triazine-5-carbothioic acid amide (Compound 21)

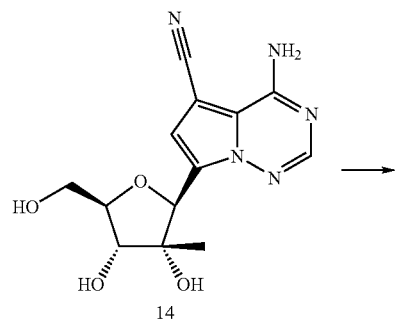
14

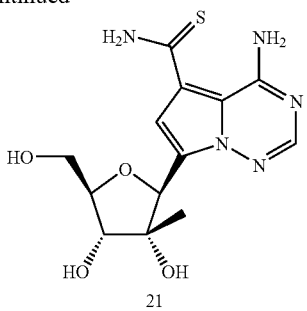
21

Step i: to anhydrous EtOH (30 μl) was added P$_2$S$_5$ (7.30 mg, 0.02 mmol) and the mixture stirred in a sealed vial for 1 h at RT. To the reaction mixture was added a solution of Compound 14 (51 mg, 0.0033 mmol) in anhydrous EtOH. (30 μl). The mixture was heated in a sealed vial at 120° C. for 3 h and then cooled to RT, whereupon water was added and the mixture extracted with DCM. The aqueous layer was concentrated to dryness and the residue purified by column chromatography silica gel (elution gradient ethyl acetate to 17% methanol in ethyl acetate) to afford Compound 21: ESI-MS m/z 340 ([M+H]$^+$).

Example 12

Preparation of 4-amino-5-oxazol-2-yl-7-(2-C-methyl-β-D-ribofuranosyl)-pyrrolo[2,1-f][1,2,4]triazine (Compound 22)

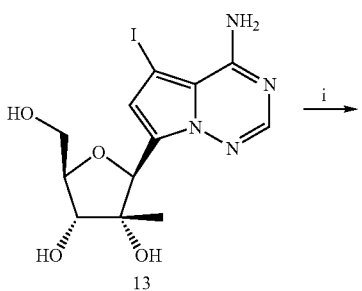
13

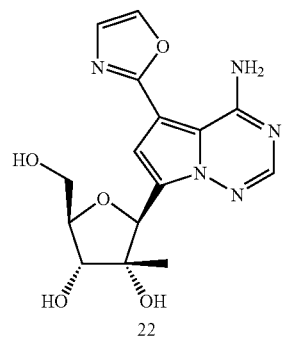
22

Step i: to a solution of Compound 13 (60 mg, 0.148 mmol) in anhydrous DMA (2.5 ml) was added the stannyloxazole (120 μl, 0.573 mmol), and the mixture was degassed and purged with Ar 5 times. Pd(P$^t$Bu$_3$)$_2$ (15 mg, 0.029 mmol) was then added and the mixture heated at 150° C. for 1 h. The mixture was cooled to RT, and the DMA was removed by distillation (Kugelrohr). The residue was taken up in acetonitrile (10 ml) and the solution extracted with hexane (10×20 ml). The acetonitrile phase was concentrated in vacuo, and the residue was purified on silica (elution gradient ethyl acetate to 16% methanol in ethyl acetate) to afford Compound 22: ESI-MS m/z 348 ([M+H]$^+$); $^1$H NMR (300 MHz, d$_6$-DMSO): δ 10.1 (br d, 1H, J 1.8 Hz), 8.24 (br d, J 1.8 Hz, 1H), 8.17 (d, J 0.9 Hz, 1H), 7.94 (s, 1H), 7.40 (d, J 0.9 Hz, 1H), 7.33 (s, 1H), 5.40 (d, 0.5 Hz, 1H), 4.94-4.88 (m, 2H), 4.75 (s, 1H), 3.80-3.72 (m, 3H), 3.64-3.57 (m, 1H), 0.81 (s, 3H).

Example 13

Preparation of 4-amino-5-thiazol-2-yl-7-(2-C-methyl-β-D-ribofuranosyl)-pyrrolo[2,1-f][1,2,4]triazine (Compound 23)

Example 14

Preparation of 4-amino-5-(3H-[1,2,3]triazol-4-yl)-7-(2-C-methyl-β-D-ribofuranosyl)-pyrrolo[2,1-f][1,2,4]triazine (Compound 24)

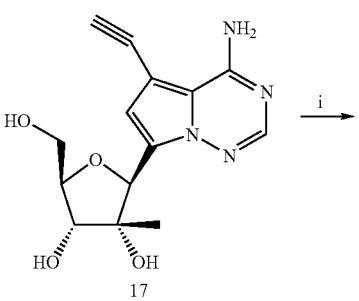

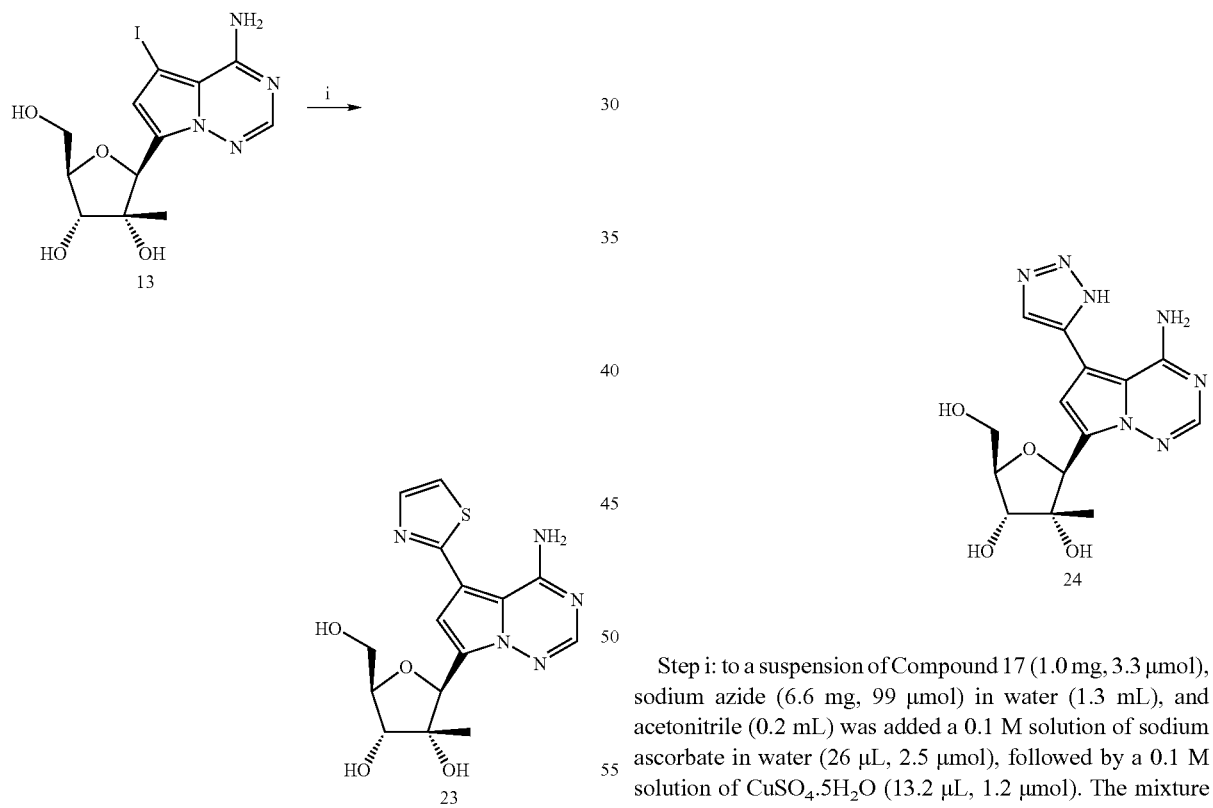

Step i: to a solution of Compound 13 (20 mg, 0.05 mmol) in DMA (2 ml) under Ar was added tributylstannylthiazole (0.2 ml, 0.64 mmol) and Pd(PPh$_3$)$_4$ (2.85 mg, 0.002 mmol). The resultant solution was heated to 60° C. overnight and then 80° C. for 4 h. Upon cooling to RT, the DMA was removed by Kugelrohr distillation. The crude material was purified by normal phase silica gel chromatography (Biotage MPLC) to yield Compound 23 as a white solid (2.5 mg): ESI-MS m/z 364.17 ([M+H]$^+$).

Step i: to a suspension of Compound 17 (1.0 mg, 3.3 μmol), sodium azide (6.6 mg, 99 μmol) in water (1.3 mL), and acetonitrile (0.2 mL) was added a 0.1 M solution of sodium ascorbate in water (26 μL, 2.5 μmol), followed by a 0.1 M solution of CuSO$_4$.5H$_2$O (13.2 μL, 1.2 μmol). The mixture was stirred at 120° C. under microwave irradiation for 5 h. The triazole (Compound 24) was observed in the reaction mixture before concentration of the residue in vacuo to afford the crude product: ESI-MS m/z 348.1 ([M+H]$^+$).

Example 15

Preparation of 4-Amino-6-fluoro-7-(2-C-methyl-β-D-ribofuranosyl)-pyrrolo[2,1-f][1,2,4]triazin-7-yl (Compound 32)

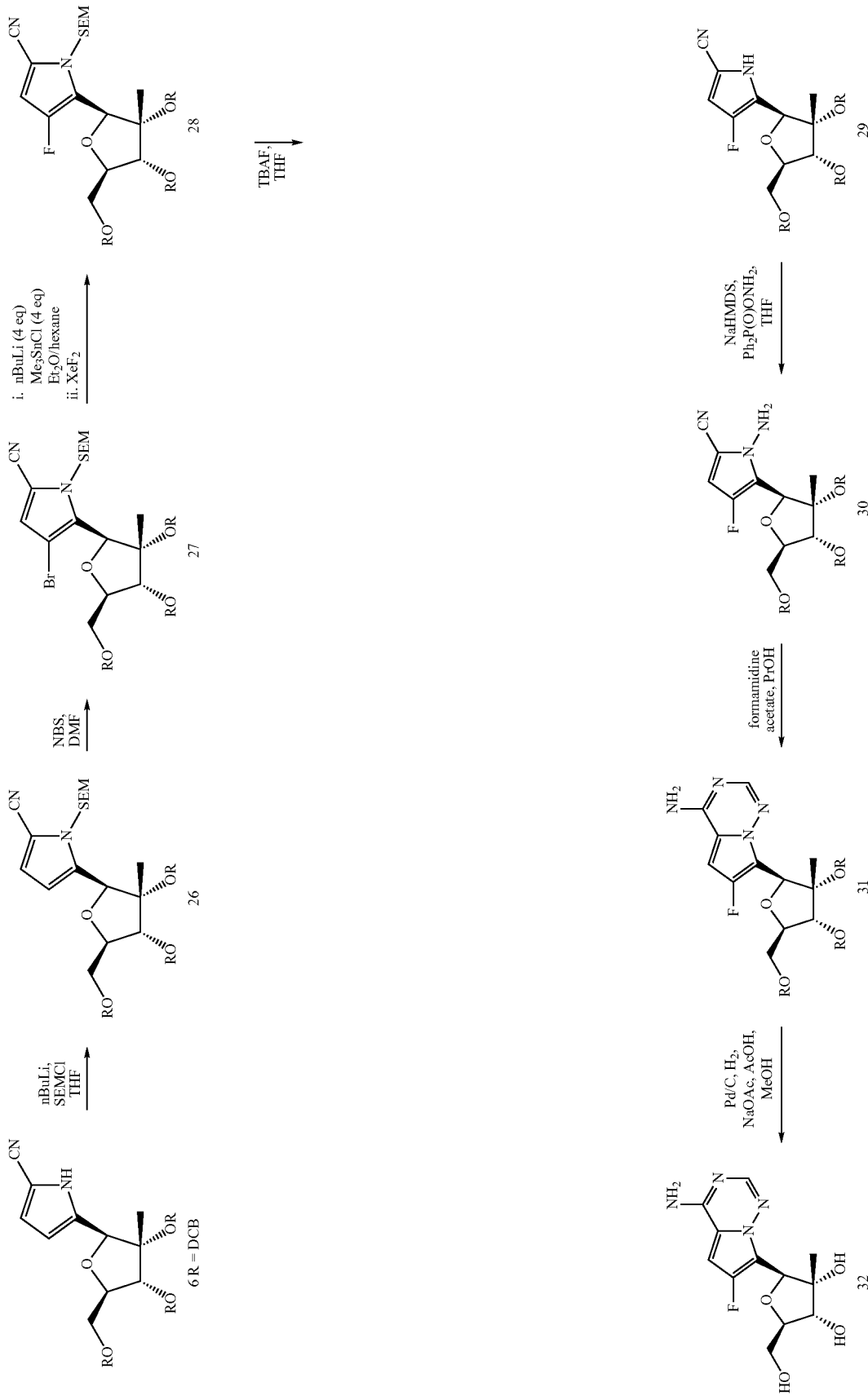

Step i: to a solution of 6 (1.3 g) in THF (15 mL) at −78° C. was added nBuLi (1.24 mL; 1.6 M in hexanes). After 15 minutes 2-chloromethoxy-ethyl-trimethylsilane (0.48 mL) was added. The reaction mixture was warmed to ambient temperature and stirred for 15 hours. NH$_4$Cl$_{(aq)}$ (50 mL) added and the aqueous layer was extracted with ethyl acetate (3×35 mL). The combined organics were washed with brine, dried (MgSO$_4$) and concentrated to leave a pale yellow oil (1.91 g). Purification by flash column chromatography on silica eluting with 15 to 25% EtOAc/hexane afforded Compound 26 (1.39 g). Rf-0.3 in 15% EtOAc/hexane.

Step ii: to a solution of 26 (1.17 g) in DMF (20 mL) at ambient temperature was added N-bromo succinimide (0.49 g) and the reaction mixture was left to stir. After 16 hours tlc analysis showed consumption of 2 and the formation of a new spot. Methanol (5 mL) was added and the reaction mixture was concentrated to leave a viscous yellow oil (1.98 g) which was purified by flash column chromatography on silica eluting with 10% EtOAc/hexane to leave Compound 27 (1.01 g) as pale yellow oil.

Step iii: to a solution of 27 (350 mg) in Et$_2$O/hexane (6 mL; 1:2) at −78° C. was added dropwise a solution of nBuLi (1.0 mL; 1.5 M in hexane). The reaction mixture was stirred for 15 minutes and then a solution of trimethyltin chloride (1.5 mL; 1.0 M in tetrahydrofuran) was added dropwise. The reaction mixture was slowly warmed to ambient temperature over 70 minutes. Tlc analysis showed the disappearance of SM (Rf~0.5 in 15% EtOAc/hexane) and the emergence of 2 new spots (Rf~0.35—reduced bromopyrrole and Rf~0.6—product). NH$_4$Cl$_{(aq)}$ (20 mL) was added and the aqueous layer was extracted with ethyl acetate (3×20 mL) and the combined organics were washed with brine (20 mL), dried (MgSO$_4$) and concentrated to leave a yellow oil (510 mg). The crude stannane was dissolved in dichloromethane (8 mL) and xenon difluoride (71 mg), silver triflate (146 mg) and di tert butyl-4-methyl-pyridine (16 mg) were added at ambient temperature. After 10 minutes tlc analysis showed the consumption of starting material and the appearance of a new spot (Rf~0.3-10% EtOAc/hexane). NaHCO$_3$ $_{(aq)}$ (20 mL) was added and the reaction was extracted with dichloromethane (3×20 mL) and the combined organics were washed with brine (20 mL) dried (MgSO$_4$) and concentrated to leave a pale brown oil (410 mg). Purification was by flash column chromatography on silica eluting with 1% to 3% to 6% to 10% EtOAc/hexane to afford product 28 (65 mg) as an amorphous white solid.

Step iv: to a solution of 28 (60 mg) in THF (1.5 mL) was added a solution of TBAF (0.21 mL; 1.0 M in tetrahydrofuran) and the reaction placed in a microwave reactor and heated to 75° C. for 45 minutes. Tlc analysis showed the appearance of a new product (Rf-0.3 in 20% EtOAc/hexane). NH$_4$Cl$_{(aq)}$ (10 mL) was added and the aqueous layer was extracted with ethyl acetate (3×15 mL). The combined organics were washed with brine (10 mL), dried (MgSO$_4$) and concentrated to leave a pale yellow oil (12 mg). Purification by flash column chromatography on silica eluting with 100% hexane to 16% EtOAc/hexane afforded product 29 (42 mg) as a white solid.

Step v: to a solution of 29 (27 mg) in THF (0.5 mL) at −5° C. was added lithium hexamethyl disilazide (60 µL; 1.0 M in tetrahydrofuran). The reaction mixture was warmed to ambient temperature over 15 minutes then diphenylphosphinyl-hydroxylamine (13 mg) was added and the reaction mixture was stirred for 1 hour. Tlc analysis displayed a new spot of very similar Rf (0.26 in 20% EtOAc/hexane). H$_2$O (10 mL) was added and the aqueous layer was extracted with ethyl acetate (3×15 mL). The combined organics were washed with brine (10 mL), dried (MgSO$_4$) and concentrated to leave crude 30 (45 mg) which was used directly in the next reaction.

Step vi: a suspension of 30 (28 mg) and formamidine acetate (290 mg) in propan-1-ol (2.0 mL) was heated for 1 hour at 200° C. in a microwave reactor. A dark brown suspension resulted. LC/MS analysis showed consumption of SM and product formation. A new spot was observed by tlc (Rf-0.35 in 40% EtOAc/hexane). The reaction mixture was concentrated to leave a brown oil which was purified by flash column chromatography on silica eluting with 20% to 30% to 40% EtOAc/hexane affording 31 (21 mg) as an amorphous white solid.

Step vii: to a solution of 31 (20 mg) in methanol at ambient temperature was added sodium acetate (21 mg), acetic acid (4 drops) and palladium (27 mg; 10% on carbon). The atmosphere was evacuated and filled with hydrogen gas (repeated 3 times) and the reaction was left to stir at 45° C. After 16 hours the reaction mixture was analyzed by LC/MS and shown to be complete. The reaction mixture was filtered through a 0.45 um syringe filter and the residue washed with methanol (7 mL). The filtrate was concentrated to leave the crude product as a white solid (44 mg). Purification by flash column chromatography on silica eluting with 100% DCM to 10% MeOH/DCM to 20% MeOH/DCM afforded Compound 32 (3.5 mg) as a white solid. Rf-0.5 in 20% MeOH/DCM; $^1$H NMR (d$_4$-MeOD) δ 7.85 (s, 1H), 6.63 (s, 1H), 5.57 (s, 1H), 3.99 (m, 2H), 3.85 (m, 2H), 1.02 (s, 3H); ES/MS: m/z 299.1 ([MH$^+$]).

Example 16

Preparation of Bis-POM (pivaloyloxymethyl) prodrug of 4-amino-7-(2-C-methyl-β-D-ribofuranosyl)-pyrrolo[2,1-f][1,2,4]triazine (Compound 34)

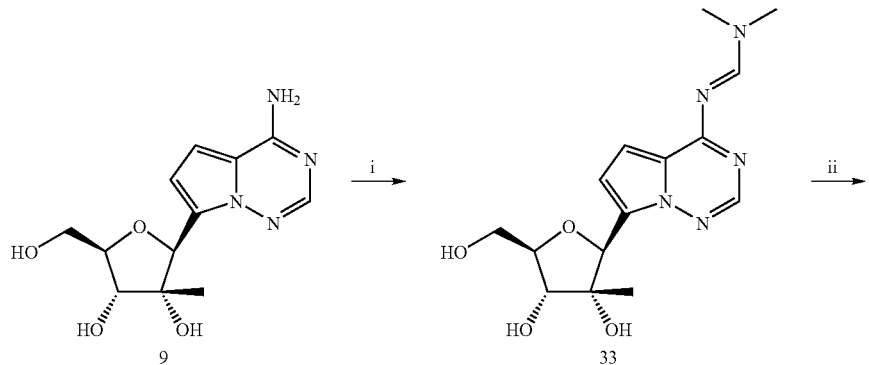

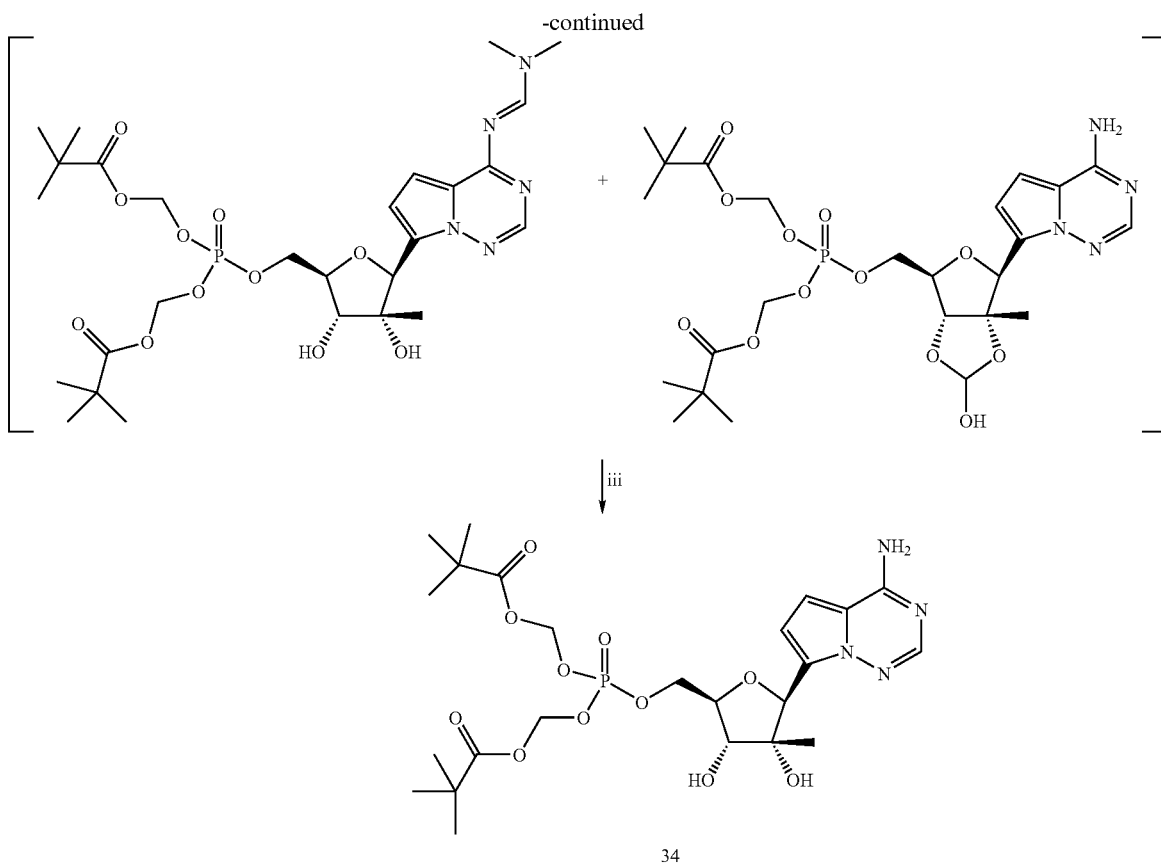

Step i: Compound 9,4-amino-7-(2-C-methyl-β-D-ribofuranosyl)-pyrrolo[2,1-f][1,2,4]triazine (156 mg) in anhydrous DMF (2 mL) was treated with N,N-Dimethylformamide dimethyl acetal (730 uL) and the resulting solution heated in a microwave reactor at 70° C. for 10 min. The mixture was cooled and the solvent removed and the crude material purified on silica with 0-20% MeOH:DCM to afford Compound 33 (200 mg). ESI-MS m/z 336 ([M+H]$^+$); $^1$H NMR (d$_6$-CD$_3$CN) δ 8.87 (s, 1H), 7.99 (s, 1H), 6.84 (d, J 4.4 Hz, 1H), 6.75 (d, J 4.4 Hz, 1H), 5.45 (s, 1H), 5.44 (br s, 1H), 4.09 (br s, 1H), 3.8-3.9 (m, 3H), 3.55-3.75 (m, 2H), 3.20 (s, 3H), 3.19 (s, 3H), 0.87 (s, 3H).

Step ii: Bis-POM phosphoric acid, was dissolved in DCM (20 mL) and DMF (2 drops) under an atmosphere of Ar. Oxalyl chloride (1.16 mL) was added dropwise and the solution left to stir for 2 h before the solvent was removed under high vacuum to afford the phosphoryl chloride as a yellow oil. The residue was dissolved in anhydrous THF (1 mL) and added dropwise to a solution of Compound 33 in pyridine (1 mL). The mixture was stirred at room temperature for 5 d before saturated ammonium chloride solution (5 mL) was added. The mixture was extracted with ethyl acetate and the combined extracts dried (brine, Na$_2$SO$_4$), filtered, and concentrated in vacuo. The crude residue was purified on silica with 0-20% MeOH:DCM. Fractions were analyzed by 1 cms and those containing Bis-POM nucleoside compounds were combined and the solvent removed to afford a crude mixture. The crude mixture was subjected to hydrolysis without further purification. ESI-MS m/z 617 ([M+H]$^+$), 645 ([M+H]$^+$).

Step iii: The crude mixture containing Bis-POM nucleosides in acetonitrile (1.2 mL) was treated with HCl (1M, 0.6 mL) and the mixture heated in a microwave reactor at 60° C. for 10 min. The reaction mixture was diluted by adding water (1 mL) and DMSO (1.2 mL) then filtered.). Purification by preparative reverse phase HPLC (60% to 90% MeOH in water: 10% NH$_4$OAc buffer) afforded Compound 34 as a glassy solid (5.8 mg). ESI-MS m/z 589 ([M+H]$^+$), 611 ([M+Na]$^+$); $^1$H NMR (d$_6$-DMSO) δ 7.82 (s, 1H), 7.66 (br s, 2H), 6.84 (d, J 4.4 Hz, 1H), 6.54 (d, J 4.4 Hz, 1H), 5.63 (s, 2H), 5.59 (s, 2H), 5.43 (s, 1H), 5.18 (br s, 1H), 4.89 (br s, 1H), 4.18-4.38 (m, 2H), 3.96 (br tr, J 6-8 Hz, 1H), 3.68 (d, J 8.7 Hz, 1H), 1.17 (s, 9H), 1.16 (s, 9H), 0.78 (s, 3H).

Example 17

Preparation of 4-amino-5-imidazole-7-(2-C-methyl-β-D-ribofuranosyl)-pyrrolo[2,1-f][1,2,4]triazine (Compound 38)

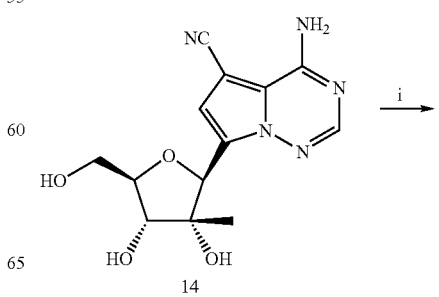

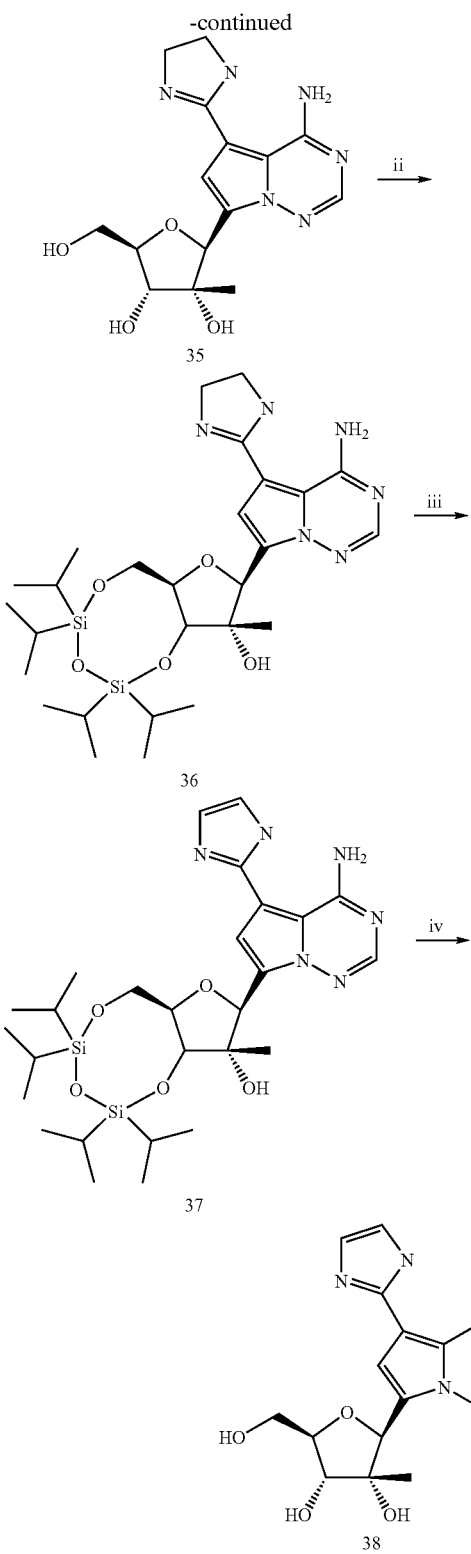

$d_6$-DMSO): δ 11.90 (br d, J 3.5 Hz, 1H), 7.88 (br d, J 3.6 Hz, 1H), 7.84 (s, 1H), 7.21 (s, 1H), 7.04 (s, 1H), 5.38 (s, 1H), 4.95 (d, J 6.9 Hz, 1H), 4.71 (s, 1H), 4.65 (t, J 5.6 Hz, 1H), 3.88-3.39 (m, 8H), 0.82 (s, 3H).

Step ii: Compound 35 (12 mg) and imidazole (21.1 mg) were combined and co-evaporated with acetonitrile three times. DMF (0.2 ml) followed by 1,3-dichloro-1,1,3,3-tetraisopropyldisiloxane (16.5 μl) was added and the mixture was stirred at RT overnight. The solvent was removed in vacuo. Hexane was added and the silyloxy protected Compound 36 was collected (16 mg) and taken on to the next step without further purification.

Step iii: 2-iodoxybenzoic acid (IBX, 14 mg) was added to a solution of Compound 36 (22 mg) in DMSO (0.3 ml) and the mixture was heated at 45° C. for 3 h. The solvent was removed in vacuo. The yellow residue was suspended in EtOAc and quenched with saturated aqueous sodium metabisulfite, washed with 1M NaOH, dried (MgSO$_4$), filtered and concentrated in vacuo. Purification by column chromatography (50% EtOAc/hexane) afforded the oxidized Compound 37 (7.5 mg).

Step iv: TBAF (3 mg) was added to a solution of Compound 37 (7.5 mg) in THF (0.1 ml) and the mixture was stirred at RT for 5 minutes. The solvent was removed in vacuo and the mixture was purified by column chromatography (100% EtOAc then 5% MeOH/EtOAc) to afford the deprotected 4-amino-5-imidazole-7-(2-C-methyl-β-D-ribofuranosyl)-pyrrolo[2,1-f][1,2,4]triazine, Compound 38 (1.2 mg) as a white solid: ESI-MS m/z 347 ([M+H]$^+$); $^1$H NMR (300 MHz, $d_6$-DMSO): δ 12.54 (br s, 1H), 11.43 (br s, 1H), 7.91 (br s, 1H), 7.80 (s, 1H), 7.23 (m, 1H), 7.15 (s, 1H), 7.03 (m, 1H), 5.40 (s, 1H), 4.98 (d, J 6.9 Hz, 1H), 4.74 (s, 1H), 4.67 (t, J 5.7 Hz, 1H), 3.85-3.51 (m, 4H), 0.85 (s, 3H).

Example 18

Nucleoside 5'-mono-phosphates

To the appropriate nucleoside compound (0.156 mmol) (dried over P20s in vacuum overnight) is added trimethyl phosphate (1.5 mL). The mixture is stirred overnight in a sealed container containing 4A molecular sieves. It is then cooled to 0° C. and phosphorous oxychloride (35.8 mL, 2.5 eq.) is added via syringe. The mixture is stirred for 3 h at 0° C., then the reaction is quenched by addition of tetraethylammonium bicarbonate (TEAB) (1M) (1.5 mL) and water (15 mL). The aqueous solution is washed with CHCl$_3$ and ether, then lyophilised. The crude product is purified by HPLC using a C18 column with water and 5% acetonitrile in water to provide the mono-phosphate as a triethylammonium salt after lyophilization.

Example 19

5'-p-Phenyl methoxyalaninylphosphate prodrugs

To a solution of the appropriate nucleoside compound (0.6 mmol) in anhydrous THF (5 mL) is added phenyl methoxyalaninylphosphorochloridate (40 mg, 5 eq.) (freshly prepared following the literature procedure: J Med. Chem. 1993, 36, 1048-1052 and Antiviral Research, 1999, '43, 37-53) and 1-methylimidazole (95 μl, 10 eq.) at RT under Ar. The reaction is followed by TLC. After 36 h, the reaction mixture is evaporated and the residue purified on silica gel with 0-10% MeOH in CH$_2$Cl$_2$ as eluent to provide a 1:1 mixture of diastereomers.

Step i: ethylenediamine (600 μl) was added to Compound 14 (30 mg) and the reaction placed in a microwave reactor and heated to 110° C. for 40 minutes. The solvent was removed in vacuo. The crude material was purified by column chromatography (100% EtOAc then 15% MeOH/EtOAc) to afford the reduced imidazole, Compound 35 (13.1 mg) as a white solid: ESI-MS m/z 349 ([M+H]$^+$); $^1$H NMR (300 MHz,

Example 20

2-[5-O-Bis(pivaloyloxymethyl)]phosphoryl-prodrugs

To a solution of triethylammonium salt of compound nucleoside mono-phosphate (0.024 mmol) in anhydrous MeOH (0.5 mL) is added tributylstannyl methoxide (14 jj. L, 2 eq.) at RT under Ar. The reaction mixture is stirred at RT for 30 min then evaporated and co-evaporated with acetonitrile three times. The residue is dissolved in anhydrous acetonitrile (3 mL) and tetrabutylammonium bromide (15.5 mg, 2 eq.) and iodomethyl piovalate (58 mg, 10 eq) are added. The reaction mixture is heated at reflux for 1 h cooled to RT, and the solvent is evaporated. The residue is purified on a silica gel column with 1-5% MeOH in $CH_2Cl_2$ to provide the prodrug.

Example 21

Nucleoside 5'-di-phosphates

To a solution of the triethylammonium salt of 5'-monophosphate (0.031 mmol) [dried by coevaporation with anhydrous DMF twice (2×1 mL)] in 0.5 mL of anhydrous DMF is added N,N'-carbonyldiimidazole (25 mg, 5 eq.) at RT under Ar. The reaction mixture is stirred at RT for 4 h after which analytical TLC shows no starting material. Then tributylammonium phosphate salt (1.5 7H-$Bu_3$N/phosphate, which is prepared (see PCT, WO 88/03921) and further dried by coevaporation with anhydrous DMF three times) is added to the above solution. The reaction is followed by TLC and typically after 3 days, LC-MS shows significant (>50%) conversion to product. The reaction is quenched with 1 mL of triethylamine, 1 mL of water, and stirred at RT for 40 min. The crude product is purified by reverse phase HPLC to provide pure product.

Example 22

Nucleoside-5'-tri-phosphates

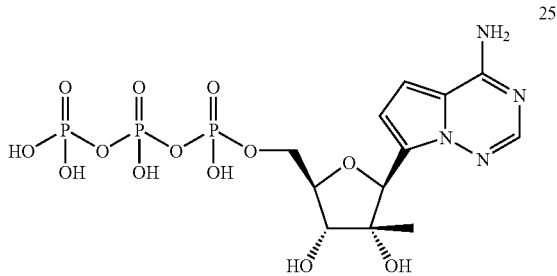

Referred to Herein as Compound 25

To an ice-cold mixture of nucleoside (0.1 mmol) in trimethyl phosphate (1 mL, anhydrous) was added $POCl_3$ (30 µl), and the mixture was stirred at 0° C. for 2 h before the addition of $Bu_3$N (72 µl) followed by acetonitrile (0.5 mL) and tributylammonium pyrophosphate (190 mg). After a further 2 h at 0° C., the reaction was quenched by pouring it into ice-cold 1M triethylammonium bicarbonate buffer (10 mL, pH 8.5). The product was purified by preparative HPLC to yield the Compound 25: MS m/z ([M−H]$^-$) 519; $^{31}$P NMR ($D_2O$) δ -7.4 (m, 1P), −10.1 to −10.2 (m, 1P), −21.1 to −21.3 (m, 1P).

Example 23

Cell-Based HCV RNA Replication Luciferase Reporter Assay

The MP-1 cells for the Cell-Based HCV RNA Replication Luciferase Reporter Assay Protocol include a Huh-7 (human hepatoma) derived cell line that harbors a replicating RNA in the cytoplasm. This RNA, termed a replicon, encodes all of the HCV non-structural proteins (HCV NS2 to NS5B, inclusively) that catalyze the replication of the RNA replicon. Replicon copy number per cell is about 1000 to 5000. The replicon is stably maintained as an episome in dividing cells, and therefore it is important to keep the cells in a sub-confluent state and to ensure selection for the replicon by culturing the cells in medium supplemented with 0.25 mg/ml G418. The entire structural region of the HCV genome is replaced with a neomycin resistance gene; hence this cell line produces no infectious virus. Moreover, the *firefly luciferase* gene is fused to the neo$^r$ gene with an FMDV-2A autoprocessing peptide that allows for expression of both mature luciferase and neomycin phosphotransferase from one cistron. Luciferase levels are directly proportional to the HCV RNA levels, and the cell system allows for the evaluation of the potency of HCV inhibitors in cell culture.

The assay outline includes the following steps on Day 1: (1) Plate cells at a density of 10,000 cells/well of a 96 well plate and incubate 37° C.; (2) Make compound dilutions; (3) Add compound dilutions to cells; (4) Incubate for 72 h. The assay includes the following steps on Day 4: (1) Perform Cell titer blue assay for cytotoxicity (the assay is based on the reduction of resazurin (cell titer blue) into a fluorescent product, resorufin, in metabolically active cells, and the assay can be duplexed with the assay used for HCV replicon luciferase reporter assay); (2) Perform luciferase assay with the Bright-Glo luciferase substrate (Promega) and read luminescence; (3) Process results.

Under this outline, the cell culture includes MP-1 cells (Huh7 cells maintaining an HCV subgenomic replicon containing the luciferase-FMDV 2A-neomycin phosphotransferase fusion gene). The MP-1 cells are maintained in Dulbecco's Modified Earle Medium (DMEM) supplemented with 10% FBS and 0.25 mg/ml G418. The cells are passaged by trypsinization and frozen in 90% FBS/10% DMSO. During the assay, the DMEM medium is supplemented with 10% FBS, containing 0.5% DMSO and lacking G418.

Regarding cell plate preparation, on the day of the assay, MP-1 cells are typsinised and diluted to obtain 5,000-10,000 cells/70 µl in Assay Medium. Seventy µl (about 10,000 cells) are distributed into each well of a black 96-well ViewPlate™ (Packard). The plate is incubated at 37° C. in 5% $CO_2$ until compound addition.

Compound plates are prepared as follows: (1) Add compound (20 mM in 100% DMSO) to assay Medium, lacking G418 to obtain a 60 µM solution and a final DMSO concentration of 0.5%; (2) Sonicate for 15 min (optional); (3) Filter through a 0.22 µm Millipore Filter Unit (96 well format) (optional); (4) Prepare the final dilution plate in a Deep-well titer plate, in columns 3 to 11 add 400 µl of Assay Medium (containing 0.5% DMSO); (5) Transfer 200 µl of compound solution to column 3 of the dilution plate; the highest concentration (2×) is prepared in column 3; (7) Prepare ⅓ serial dilutions by transferring 200 µl from column 3 to column 4, then from column 4 to column 5, serially through to column 11 (no compound is included in column 12).

The test compound is added to the cells by transferring 70 µl from each well of the Compound Plate to a corresponding well of the Cell Plate (three columns are used as the "No inhibition control"; nine [9] columns are used for the nine-point dose response). The cells are incubated at 37° C., 5% $CO_2$ for 3 days.

Under the Alamar blue assay protocol, the assay plates are removed from a 37° C. incubator, and 20 µl of CellTiter-Blue™ Reagent is added. The cells are incubated in the 37° C. incubator for 3 h. The assay plates are shaken for 10 sec and fluorescence at $560_{Ex}/590_{Em}$ nm is recorded. The results are expressed relative to the 100% untreated control using the following equation: % inhibition=100−[($RFU_{compound}$−$RFU_{blank}$/$RFU_{untreated}$−$RFU_{blank}$)×100]. Alternatively, under the MTT protocol the extent of cytotoxicity is determined via metabolism of the vital dye 3-(4,5-dimethylthiazol-2-yl)-2,5-diphenyltetrazolium bromide (MTT). MTT (1 mg/ml) was added to each well and plates incubated for 3 hours incubation at 37° C. Wells were aspirated, iso-propanol (200 µL) was added and absorbance values read at 540/690 nm. Compound concentrations that developed 50% cytotoxicity ($CC_{50}$) were calculated using non-linear regression analysis.

Under the Luciferase assay protocol, the medium is aspirated from the Assay Plate and 50 µl of 1× Glo Lysis Buffer (Promega) previously warmed to room temperature is added. Incubation occurs at room temperature for 10 min with occasional shaking. Black tape is placed at the bottom of the plate, and 50 µl of Bright-Glo luciferase substrate (Promega) previously warmed to room temperature is added. Gentle mixing follows. A Packard Topcount instrument is then utilised using the following protocol: Data Mode: Luminescence (CPS); Count Delay=1 min; Count time=2 sec. The luminescence determination (CPS) in each well of the culture plate is a measure of the amount of HCV RNA replication in the presence of various concentrations of inhibitor. The % inhibition is calculated with the following equation: % inhibition=100−[CPS (inhibitor)/CPS (control)×100]. A non-linear curve fit with the Hill model is applied to the inhibition-concentration data, and the 50% effective concentrations ($EC_{50}$) are calculated using a computer curve fitting program. The biological properties of representative compounds of formula I shown below in Table No. 3 were investigated in the cell-based HCV RNA replication luciferase reporter assay by way of the experimental protocol described above.

TABLE NO. 3

Cell-Based HCV RNA Replication Luciferase Reporter Assay $EC_{50}$ and $CC_{50}$ concentrations.

| Compound No. | Example No. | $EC_{50}$ µM | $CC_{50}$ µM |
|---|---|---|---|
| 9 | 1 | 1.3 | 365 |
| 11 | 2 | 3.1 | >100 |
| 12 | 3 | 0.22 | 6.5 |
| 14 | 5 | 1.4 | 18.8 |
| 15 | 6 | 0.0062 | 0.37 |
| 34 | 16 | 3.8 | 45 |

TABLE NO. 4

Cell-Based HCV RNA Replication Luciferase Reporter Assay % inhibition at 50uM.

| Compound No. | Example No. | Inhibition at 50 µM (%) |
|---|---|---|
| 9 | 1 | 99 |
| 11 | 2 | 97 |
| 12 | 3 | 99 |
| 13 | 4 | 97 |
| 14 | 5 | 100 |
| 15 | 6 | 100 |
| 16 | 7 | 99 |
| 17 | 8 | 98 |
| 20 | 10 | 19 |
| 22 | 12 | 95 |
| 32 | 15 | 23 |
| 34 | 16 | 100 |
| 35 | 17 | 99 |
| 38 | 17 | 99 |

Example 24

Total Cellular Replicon RNA Serial Passage Protocol

The HCV sub-genomic replicon is selected in Huh-7 (human hepatoma) with G418 that maintains a replicating RNA episome in the cytoplasm of cells. HCV replicons that are resistant to a specific inhibitor of HCV RNA replication can be isolated using a dual combination of G418 and the specific inhibitor. In order to determine whether inhibitor-resistant replicon RNA encodes for a stable mutation that confers resistance, the replicon RNA can be isolated from the resistant cell-line and serially passaged into naïve Huh-7 cells by electroporation. Following a new round of selection, a cell population or cell-line with the putative inhibitor-resistant replicon can be phenotyped with the inhibitor to confirm that the resistant phenotype genetically maps to the replicon RNA.

The assay outline includes the following steps: (1) Isolate cytoplasmic RNA (Qiagen RNAeasy protocol); (2) Transfect into naïve Huh-7 cells; (3) Select colonies 3-4 weeks; (4) Pick and expand colonies, or establish pooled population of cells. In particular, the total RNA is extracted from inhibitor-resistant replicon containing Huh7 cells and cultured in a 10 cm tissue culture plate, using an RNeasy Kit (Qiagen) as per the manufacturer's instructions. HCV replicon RNA copy number is determined by Taqman® RT-PCR analysis and generally, 10 to 20 µg of total cellular RNA (that contains approximately $1 \times 10^9$ copies of HCV RNA) is transfected by electroporation into $8 \times 10^6$ naïve Huh-7 cells. The transfected cells are subsequently cultured in 10 cm tissue culture plates containing DMEM supplemented with 10% fetal calf serum (10% FCS). Media are changed to DMEM (10% FCS) supplemented with 0.25 mg/ml G418 24 h after transfection and that is changed every three days. If required, cells are passaged 1:3 to maintain the culture sub-confluent. Visible colonies are formed three to four weeks post-transfection and G418 selection. G418 resistant colonies may be picked and expanded into second generation cell lines, or pooled into a population culture that constitutes the cells harboring serially passaged HCV Replicon RNA. The passage of mutations that are stable and confer resistance to a specific inhibitor are confirmed by measuring $EC_{50}$ with the second generation of replicon cells.

Example 25

NS5b Chain Termination Assay

The NS5b chain termination assay uses stepwise addition of each nucleotide complementary to the overhang of a hairpin template, with the first nucleotide radioactive, i.e. the direct labelling method. If a test compound is a chain terminator, the system is able to clearly show its incorporation into the chain, and no further extension is observed.

Under this protocol, the contents of two separate vials are prepared. Vial A contains 1.5 µl 10× buffer, 1.5 µl enzyme, 1.0 µl oligo and 5.0 µl for a total volume of approximately 9 µl. Vial B contains NTPs of 6 µl. The contents of Vial A is mixed with the contents of Vial B to provide a total volume of 15 µl, followed by incubation at 30° C. for 60 min. The aliquot is mixed with RNA loading buffer, heated at 70° C. for 15 min and run onto a 20% acrylamide gel with 7.2 M urea. The final concentration of NS5b is 1 µM, and the final concentration of NTP/cpd is 2 µM.

Example 26

HCV Polymerase Inhibition Assay

Poly r(U) RNA template (Sigma) is employed for the HCV NS5b polymerase inhibition assay using a NS5bΔ55 (genotype 1b) purified enzyme. The kinetic constant, $K_m$, is determined for the Poly r(U) template and ATP using a non-linear, least squares fit of initial rates as a function of substrate concentration assuming Michaelis-Menten kinetics.

Standard RdRp assays consist of 20 µg/mL Poly r(U) RNA template and 100 nM HCV NS5bΔ55 (genotype 1b) in a 50 µL reaction mixture containing 20 mM Tris-HCl, 5 mM $MgCl_2$, 5 mM $MnCl_2$, 3 mM DTT, 72 µM ATP, and 0.019 µM [α-$^{33}$P]ATP. Elongation reactions are initiated by the addition of ATP, and proceed for 60 min at 25° C. Reactions are quenched by the addition of 0.2 M EDTA, and product formation is collected by filtration through Multiscreen plates (Millipore). Quantification of product formation was performed using TopCount (Perkin Elmer). The inhibitor concentration at which the enzyme catalysed rate is reduced by half ($IC_{50}$) is determined using a computer program for curve fitting. $IC_{50}$ concentrations for nucleoside 5'-triphosphate compounds of the present disclosure are expected to range from <10 nM to >100 µM. Under these conditions, the $IC_{50}$ for Compound 25 is 0.37 µM.

HCV NS5b Polymerase $K_i$ Determination Assay

A modified method of the NS5b Polymerase inhibition assay was used to determine the $K_i$ and the mode of action for NS5b inhibitor compounds. The enzyme and template were fixed at 100 nM and 20 g/mL and all other reaction conditions were identical to the NS5b polymerase inhibition assay. The velocity of NS5b reactions were monitored at different ATP and inhibitor concentrations. The ATP concentration ranged from 0.1 µM to 1000 µM, and the concentration of the inhibitor ranged from 0.003 fold to 7 fold of the $IC_{50}$ value. Velocities obtained at each ATP and inhibitor concentration were analyzed using Graph Pad Prism to identify the mode of inhibition and $K_i$ for inhibitor compounds. Under these conditions, the Ki for Compound 25 is 0.08 µM.

Example 27

In vitro anabolism of Compound 9 in replicon cells and primary human hepatocytes produces the triphosphate species Compound 25. The structure of Compound 25 is

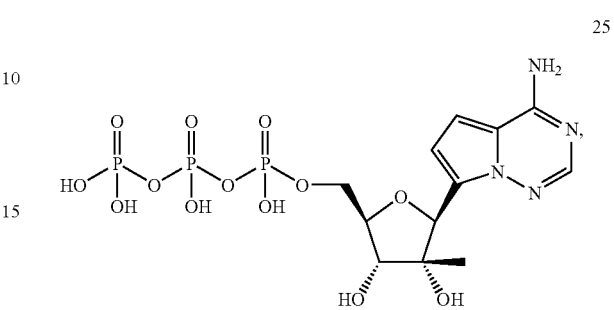

the synthetic preparation of which is discussed above in Example 22.

In vitro anabolism of Compound 9 and the intracellular accumulation of its triphosphate (Compound 25) were studied in adherent Huh-7 and plated primary human hepatocytes. The Huh-7 human hepatoma liver cells (JCRB0403 http://cellbank.nibio.go.jp/) are maintained in DMEM containing 10% fetal bovine serum (FBS). Huh-7 cell clones carrying a HCV subgenomic replicon (Lohmann et al., 1999. Science 285: 110-113) are maintained in DMEM supplemented with 10% FBS and 0.25 mg/ml G418. The cell lines are grown at 37° C. in a 5% $CO_2$-95% air atmosphere. Plated primary human hepatocytes (6-well Collagen/No Overlay) were purchased from Cellz Direct (NC, USA) and maintained in InVitroGro Medium (Celsius, In Vitro Technologies, MD USA) under the same incubation conditions.

For intracellular anabolism studies, Huh-7 cells are trypsinized, harvested, re-suspended in DMEM supplemented with 10% FBS, counted and seeded at a density of $0.7 \times 10^6$ cells per well in a six-well plate and incubated for a period of 24 hr at 37° C. in 5% $CO^2$ atmosphere. Media is removed and replaced with fresh DMEM+10% FBS containing 10 µM Compound 9 for a period of 24 hr at 37° C. The cell monolayer is then quickly washed three times with drug-free medium to remove extracellular Compound 9 and each well is incubated with fresh DMEM+10% FBS for a specified time period (i.e. 6-wells at 0, 2, 4, 8, 24 and 48 hr). At the end of the incubation period, the medium is aspirated from the well and the cell monolayer is washed with cold phosphate buffered saline, pH 7.4. The washed cell monolayer is treated with 1.0 ml ice-cold 70% methanol:water, scraped and harvested into a centrifuge tube and then sonicated for 1 min at 4° C. The resulting cell lysate is stored overnight at −80° C. and subsequently used to extract the metabolites of Compound 9. Isolation of Compound 9 and the intracellular metabolites of Compound 9 from plated primary human hepatocytes uses similar experimental conditions, except that InVitroGro Medium is used as the cell culture medium.

Sample Analysis for intracellular nucleoside metabolites: The cell lysate samples are thawed on ice, and subjected to two freeze/thaw cycles in a dry ice/acetone bath. Cells extracts are vortexed and centrifuged at 16000 g for 5 min at 4° C. and 40 µL of supernatant is injected for analysis using a API4000 triple quadrupole system. The Shimadzu LC autosampler is set at 4° C. to minimize evaporation. Compound 9 mono-, di- and triphosphate (Compound 25) are separated using a pH gradient on a Biobasic AX, 3.0×50 mm column maintained at 40° C. The mobile phase consists of solvent A (10 mM ammonium acetate in 30:70 ACN/H20 containing 0.008% glacial Acetic Acid) and solvent B (1 mM ammonium acetate in 30:70 ACN/H20 containing 0.225% ammonia hydroxide). The elution is performed using a linear gradient of buffer B from 10 to 100% in 2.5 minutes, and then held under isocratic condition for 3.0 minutes at a composition of 100% B at a constant flow rate of 0.5 ml/minute. The mass spectrometer is operated in positive ion electrospray mode utilizing a multiple reaction monitoring scan functionality at m/z m/z 361.1->227.1, 441.1->227.1 and 521.1->227.1 for Compound 9 mono-, di- and triphosphate, respectively. The respective metabolites are identified and quantified by comparing their chromatographic profiles and peak area response with those of authentic standards.

The pharmacokinetic properties of Compound 9 were determined in male Sprague-Dawley rats, beagle dogs and cynomolgus monkeys (n=3 in each species) with an oral dose of 5 mg/kg and iv dose of 2 mg/kg. PK parameters were analyzed using the WinNonlin noncompartmental model.

As shown in the Table No. 5 below, following 24 hours incubation of Huh-7-HCV subgenomic replicon cells with 10 μM initial concentration of Compound 9, the intracellular concentration of Compound 25 reached 5.7 pmol/million cells. Unexpectedly, primary human hepatocytes generate much higher (~60-fold) intracellular levels of the triphosphate of Compound 9 under the same experimental conditions.

Compounds whose plasma half-life is >2 hours, and whose intracellular therapeutically active anabolite has a half-life of >10 hours are expected to have a greater potential to be administered once daily therapeutically. The decay half-life (t1/2) of Compound 25 displays a biphasic profile in both replicon cells and primary human hepatocytes: a rapid decay t1/2 (0.59 vs 3.4 hrs), followed by a prolonged slow depletion with a t1/2≧38 hrs in both replicon cells and primary human hepatocytes.

TABLE NO. 5

Intracellular accumulation of Compound 25 and its decay half-lives in replicon cells vs in human primary hepatocytes (24 hours following incubation with Compound 9 at the initial concentration of 10 μM)

| Compound 25 | Huh-7 cells | Human Hepatocytes |
|---|---|---|
| Intracellular Triphosphate Concentration (pmol/million cells, 24 hr incubation) | 5.7 | 339 |
| Triphosphate decay half-life, Initial phase (α, h) | 0.59 | 3.4 |
| Triphosphate decay half-life, Elimination phase (β, h) | 45 | 38 |

As shown below in Table No. 6, cross-species PK of Compound 9 showed an elimination t1/2 ranging 4-7.6 hours, with a oral bioavailability of 33-96%. Based on these data, it is expected that the plasma half-life of Compound 9 in humans will be sufficient for it to be dosed once daily given the long-intracellular half-life of its triphosphate and its half-lives in different animal species.

TABLE NO. 6

Pharmacokinetic properties of Compound 9 following a single iv (2 mg/kg$_{BW}$) or oral dose (5 mg/kg$_{BW}$) in rats, monkeys and dogs.

| | CL (mL/min/kg$_{BW}$) | Vss (L/kg$_{BW}$) | $t_{1/2}$ (h) | $C_{max}$ (μM) | AUC (μM · h) | F % |
|---|---|---|---|---|---|---|
| Rat | 18.8 | 4.19 | 4.0 | 2.38 | 13.0 | 83 |
| Monkey | 20.5 | 2.43 | 4.3 | 0.82 | 5.0 | 33 |
| Dog | 11.4 | 5.22 | 7.6 | 8.36 | 24.9 | 96 |

Abbreviations:
CL: total clearance;
Vss: steady state volume distribution;
$T_{1/2}$: terminal elimination half-life;
Cmax: maximum concentration observed following the oral dose;
AUC: area under the curve of plasma exposure;
F %: oral bioavailability.

Throughout this specification and the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps. All patents, patent publications, literature, and references mentioned herein are incorporated by reference in their entirety.

We claim:
1. A compound of the formula I:

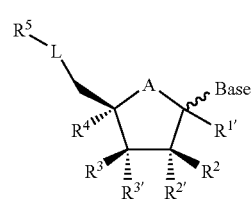

wherein
the 〜〜〜defines the active pharmaceutical ingredient as a D- or L- nucleoside or nucleotide;
A is selected from the group consisting of —O—, —S—, —CH$_2$—, —CHF—, —CF$_2$—, and —NR—;
$R^{1'}$, $R^2$, $R^{2'}$, $R^3$, $R^{3'}$, and $R^4$ are independently selected from the group consisting of —H, halogen, OH, —NHOH, —NHNH$_2$, —N$_3$, —CN, —OCOCHNC(CH$_3$)$_2$, —COOH, —CONH$_2$, —C(S)NH$_2$, —COOR, —R, —OR, —SR, —SSR, —NHR, and —NR$_2$, or $R^2$ and $R^{2'}$ together or $R^3$ and $R^{3'}$ together represents =O, =S, or =L'-Y', where L' is selected from the group consisting of N, CH, CF, CCl, and CBr and Y' is selected from the group consisting of H, halogen, N$_3$, methyl, ethyl, and CN;
R is independently halogen, —H, —OH, —SH, —CN, S(C$_1$-C$_4$ alkyl), —NO$_2$, NH$_2$, —NHNH$_2$, —N$_3$, —NR'R' wherein each R' is independently H or C$_1$-C$_4$ alkyl, —C(S)NH$_2$, —CH$_3$, —CH$_2$OH, —CH$_2$NH$_2$, CH$_2$NH$_3^+$, —COOH, —COOCH$_3$, —COOCH$_2$CH$_3$, —CONHCH$_3$, —CONH$_2$, —CF$_3$, —N(CH$_3$)$_2$, —NHCOCH$_3$, —NHCONH$_2$, —NHCNHNH$_2$, —ONH$_2$, —CH$_2$OCH$_3$, —O(CH$_2$)CH$_3$, COOC$_1$-C$_4$ alkyl, optionally substituted alkyl, optionally substituted alkenyl, optionally substituted alkynyl, optionally substituted aryl, optionally substituted acyl, optionally substituted arylalkyl, optionally substituted cycloalkyl, optionally substituted cycloalkenyl, optionally substituted phenyl, optionally substituted heteroaryl, optionally substituted heterocyclyl, optionally substituted alkyloxy, optionally substituted alkenyloxy, optionally substituted alkynoxy, optionally substituted aryloxy, optionally substituted acyloxy, optionally substituted oxyacyl, optionally substituted arylalkoxy, optionally substituted heterocycloxy, optionally substituted heteroaryloxy, optionally substituted cycloalkoxy, optionally substituted cycloalkenoxy, optionally substituted amino, optionally substituted aminoacyl, optionally substituted aminoacyloxy, optionally substituted acylamino, optionally substituted oxyacylamino, optionally substituted oxyacyloxy, optionally substituted acylimino, optionally substituted acyliminoxy, optionally substituted oxyacylimino, optionally substituted aminothioacyl, optionally substituted thioacylamino, optionally substituted aminosulfinyl, optionally substituted aminosulfonyl, optionally substituted thio, optionally substituted thioalkyl, optionally substituted thioacyl, optionally substituted thioacyloxy, optionally substituted oxythioacyl, optionally substituted oxythioacyloxy, optionally substituted phosphorylamino, optionally substituted sulfinyl, optionally substituted sulfonyl, optionally substituted sulfinylamino, optionally substituted sulfonylamino, optionally substituted oxysulfinylamino, and optionally substituted oxysulfonylamino;

L is selected from the group consisting —O—, —S—, —NH—, —NR—, —CY$_3$, —CY$_2$O—, —CY$_2$S—, —CY$_2$NH—, —CY$_2$—, —CY$_2$CY$_2$—, —CY$_2$OCY$_2$—, —CY$_2$SCY$_2$—, and —CY$_2$NHCY$_2$—;

Y is independently selected from the group consisting of —H, halogen, —R, —OR, and —NR$_2$;

R$^5$ is selected from the group consisting of —OH, —R, —OR, —NR$_2$, or a mono-phosphate, di-phosphate, or tri-phosphate moiety or mimic thereof;

Base is a group of formula II:

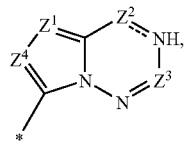

II wherein
the -----is a single or double bond;

Z$^1$, Z$^3$ and Z$^4$ are independently selected from the group consisting of >C—CONHR, >C—CONR$_2$, >C—C(S)NH$_2$, >C—COOR, >C—R, >C—OR, >C—SR, >C—NHR, >C—NR$_2$, >C-optionally substituted heteroaryl, >C-optionally substituted alkyl, and >C-G;

Z$^2$ is selected from the group consisting of >C—NH$_2$ and >C═O;

G is independently selected from the group consisting of —H, —F, —Cl, —I, —NH$_2$, —NHCH$_3$, —CN, COOH, —CSNH$_2$, —C≡CH, —C≡CCH$_3$, —C≡CCH$_2$OH, —C≡C—Si(CH$_3$)$_3$, —CONH$_2$, —CONHCH$_3$, —CONH-phenyl, —CONH-methylphenyl, thiazole, oxazole, imidazole, imidazoline, triazole, and tetrazole, and when the compound comprises two or more G groups, the G's are identical or different; and when A is O; R$^{1'}$, R$^3$, R$^{4'}$, and R5 are H; L is O; and R$^{2'}$ and R$^{3'}$ are OH; then R$^2$ is halogen, OH, NHOH, NHNH$_2$, N$_3$, CN, OCOCHNC(CH$_3$)$_2$, COOH, CONH$_2$, C(S)NH$_2$, COOR, R$^6$, OR, SR, SSR, NHR, or NR$_2$, and R$^6$ is halogen, OH, SH, CN, S(C$_{1-4}$ alkyl), NO$_2$, NH$_2$, NHNH$_2$, N$_3$, NR'R' wherein each R' is independently H or C$_{1-4}$ alkyl, C(S)NH$_2$, CH$_3$, CH$_2$OH, CH$_2$NH$_2$, CH$_2$NH$_3^+$, COOH, COOCH$_3$, COOCH$_2$CH$_3$, CONHCH$_3$, CONH$_2$, CF$_3$, N(CH$_3$)$_2$, NHCOCH$_3$, NHCONH$_2$, NHCNHNH$_2$, ONH$_2$, CH$_2$OCH$_3$, O(CH$_2$)

CH$_3$, COO(C$_{1-4}$ alkyl), substituted alkyl, substituted alkenyl, substituted alkynyl, substituted aryl, substituted acyl, substituted arylalkyl, substituted cycloalkyl, substituted cycloalkenyl, substituted phenyl, substituted heteroaryl, substituted heterocyclyl, substituted alkyloxy, substituted alkenyloxy, substituted alkynoxy, substituted aryloxy, substituted acyloxy, substituted oxyacyl, substituted arylalkoxy, substituted heterocycloxy, substituted heteroaryloxy, substituted cycloalkoxy, substituted cycloalkenoxy, substituted amino, substituted aminoacyl, substituted aminoacyloxy, substituted acylamino, substituted oxyacylamino, substituted oxyacyloxy, substituted acylimino, substituted acyliminoxy, substituted oxyacylimino, substituted aminothioacyl, substituted thioacylamino, substituted aminosulfinyl, substituted aminosulfonyl, substituted thio, substituted thioalkyl, substituted thioacyl, substituted thioacyloxy, substituted oxythioacyl, substituted oxythioacyloxy, substituted phosphorylamino, substituted sulfinyl, substituted sulfonyl, substituted sulfinylamino, substituted sulfonylamino, substituted oxysulfinylamino, or, substituted oxysulfonylamino; or a pharmaceutically-acceptable salt, ester, solvate, hydrate, or prodrug thereof.

2. The compound of claim 1, wherein:
-----is a double bond,
Z$^1$ is >C—R'',
Z$^2$ is >C—NH$_2$,
Z$^3$ is >C—R''',
Z$^4$ is >C—R'''', and
R'', R''' and R'''' are each independently H, F, I, Cl, NH$_2$, NHCH$_3$, C(═O)NH$_2$, C(═O)NHCH$_3$, C(═O)NH(C$_6$H$_5$), C(═O)NH(C$_6$H$_5$CH$_2$), CN, C≡CH, C≡CCH$_3$, C≡CCH$_2$OH, C≡C—Si(CH$_3$)$_3$, C(═S)NH$_2$, CO$_2$H,

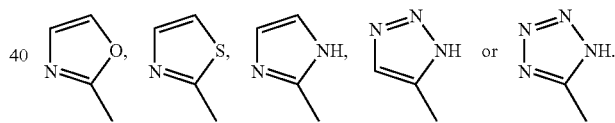

3. The compound of claim 1, wherein:
-----is a single bond,
Z$^1$ is >C—R'',
Z$^2$ is >C═O,
Z$^3$ is >C—R''',
Z$^4$ is >C—R'''', and
R'', R''' and R'''' are each independently H, F, I, Cl, NH$_2$, NHCH$_3$, C(═O)NH$_2$, C(═O)NHCH$_3$, C(═O)NH(C$_6$H$_5$), C(═O)NH(CH$_2$C$_6$H$_5$), CN, C≡CH, C≡CCH$_3$, C≡CCH$_2$OH, C≡C—Si(CH$_3$)$_3$, C(═S)NH$_2$, CO$_2$H,

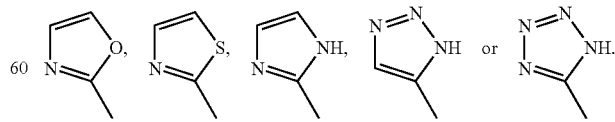

4. The compound of claim 1, wherein Z$^4$ is >C—H.

5. The compound of claim 1, wherein Z$^4$ is >C—R'''', and R'''' is F, I, Cl, NH$_2$, NHCH$_3$, C(═O)NH$_2$, C(═O)NHCH$_3$, C(═O)NHC$_6$H$_5$, C(═O)NH(CH$_2$C$_6$H$_5$), CN, C≡CH, C≡CCH₃, C≡CCH₂OH, C≡Si(CH₃)₃, C(=S)NH₂, CO₂H,

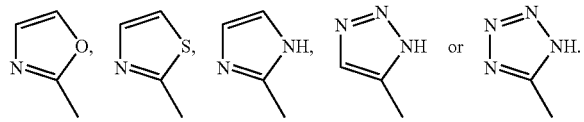

6. The compound of claim 5, wherein R"" is F, I or Cl.
7. The compound of claim 1, wherein $Z^3$ is >C—R''', and R''' is H.
8. The compound of claim 1, wherein $Z^3$ is >C—R''', and R''' is NH₂.
9. The compound of claim 1, wherein $Z^1$ is >C—H.
10. The compound of claim 1, wherein $Z^1$ is >C—R'', and R'' is independently F, I, Cl, NH₂, NHCH₃, C(=O)NH₂, C(=O)NHCH₃, C(=O)NH(C₆H₅), C(=O)NH(CH₂C₆H₅), CN, C≡CH, C≡CCH₃, C≡CCH₂OH, C≡C—Si(CH₃)₃, C(=S)NH₂, CO₂H,

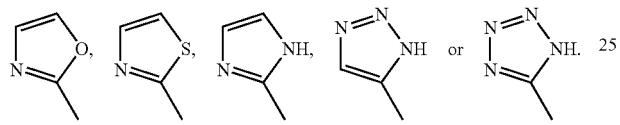

11. The compound of claim 1, wherein A is oxygen.
12. The compound of claim 1, wherein:
L is O, and
$R^5$ is H or the mono-, di- or tri-phosphate moiety or mimic thereof.
13. The compound of claim 12, wherein $R^5$ is a phosphoramidate or a phosphoester of the mono-, di- or tri-phosphate moiety.
14. The compound of claim 1, wherein the compound of formula I is selected from
4-amino-5-fluoro-7-(2-C-methyl-β-D-ribofuranosyl)-pyrrolo[2,1-f][1,2,4]triazine;
4-amino-5-chloro-7-(2-C-methyl-β-D-ribofuranosyl)-pyrrolo[2,1-f][1,2,4]triazine;
4-Amino-5-iodo-(2-C-methyl-β-D-ribofuranosyl)-pyrrolo[2,1-f][1,2,4]triazine;
4-amino-7-(2-C-methyl-β-D-ribofuranosyl)-pyrrolo[2,1-f][1,2,4]triazine-5-carbonitrile;
4-amino-7-(2-C-methyl-β-D-ribofuranosyl)-pyrrolo[2,1-f][1,2,4]triazine-5-carboxylic acid amide;
4-amino-5-trimethylsilanylethynyl-7-(2-C-methyl-β-D-ribofuranosyl)-pyrrolo[2,1-f][1,2,4]triazine;
4-amino-5-ethynyl-7-(2-C-methyl-β-D-ribofuranosyl)-pyrrolo[2,1-f][1,2,4]triazine;
4-amino-7-(2-C-methyl-β-D-ribofuranosyl)-pyrrolo[2,1-f][1,2,4]triazine-5-carboxylic acid;
2,4-diamino-7-(2-C-methyl-β-D-ribofuranosyl)-pyrrolo[2,1-f][1,2,4]triazine;
4-amino-7-(2-C-methyl-β-D-ribofuranosyl)-pyrrolo[2,1-f][1,2,4]triazine-5-carbothioic acid amide;
4-amino-5-oxazol-2-yl-7-(2-C-methyl-β-D-ribofuranosyl)-pyrrolo[2,1-f][1,2,4]triazine;
4-amino-5-thiazol-2-yl-7-(2-C-methyl-β-D-ribofuranosyl)-pyrrolo[2,1-f][1,2,4]triazine;
4-amino-5-(3H-[1,2,3]triazol-4-yl)-7-(2-C-methyl-β-D-ribofuranosyl)-pyrrolo[2,1-f][1,2,4]triazine;
4-Amino-6-fluoro-7-(2-C-methyl-β-D-ribofuranosyl)-pyrrolo[2,1-f][1,2,4]triazin-7-yl;
4-amino-5-imidazole-7-(2-C-methyl-β-D-ribofuranosyl)-pyrrolo[2,1-f][1,2,4]triazine; and
4-amino-5-imidazoline-7-(2-C-methyl-β-D-ribofuranosyl)-pyrrolo[2,1-f][1,2,4]triazine.

15. The compound of claim 1 which is 4-amino-7-(2-C-methyl-β-D-ribofuranosyl)-pyrrolo[2,1-f][1,2,4]triazine.
16. The compound of claim 1, wherein the compound of formula I is

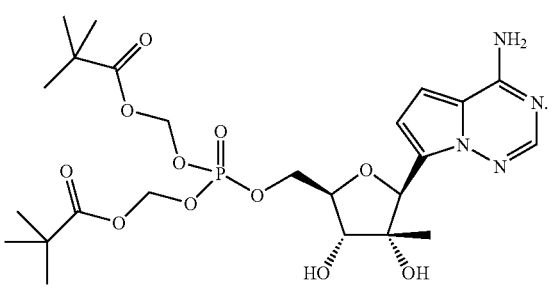

17. The compound of claim 1, wherein the compound of formula I is

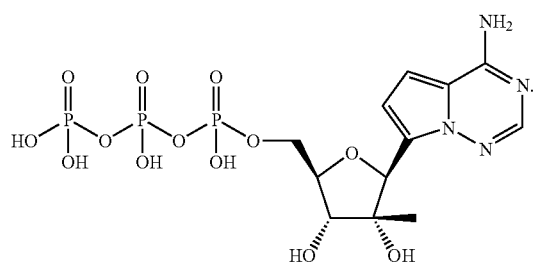

18. A pharmaceutical dosage form comprising a therapeutically effective amount of a compound of formula I according to claim 1, or a salt, ester, solvate, hydrate or prodrug thereof, and one or more pharmaceutically acceptable carriers, diluents and/or excipients.
19. The pharmaceutical dosage form according to claim 18, wherein the dosage form is adapted for once-daily dosing.
20. The pharmaceutical dosage form according to claim 18, wherein the compound of formula I is a therapeutically effective amount of 4-amino-7-(2-C-methyl-β-D-ribofuranosyl)pyrrolo[2,1-f][1,2,4]triazine.
21. A method of treating or preventing a microbial infection, a viral infection, or a proliferative disorder comprising administering a therapeutically effective amount of a compound according to claim 1, or a pharmaceutical dosage form thereof, to a patient suffering from or at risk of a microbial infection, a viral infection or a proliferative disorder.
22. The method of claim 21, wherein the patient is suffering from or is at risk of the viral infection.
23. The method of claim 22, wherein the viral infection is a hepatitis C viral infection.
24. The method of claim 21, wherein the compound or the pharmaceutical dosage form thereof is administered to the patient once-daily.
25. The method of claim 24, wherein the compound is administered to the patient in the range of about 10 μg/kg to about 30 mg/kg.
26. The method of claim 25, wherein the compound is 4-amino-7-(2-C-methyl-β-D-ribofuranosyl)pyrrolo[2,1-f][1,2,4]triazine.

27. A method of inhibiting polymerase activity in a human patient comprising administering a compound according to claim 1, or a pharmaceutical dosage form thereof, to the human patient.

28. The method of claim 27, wherein the polymerase activity is HCV NS5B polymerase activity.

29. The method of claim 27, wherein the method comprises in-vivo production of a therapeutically effective metabolite of the compound of formula I that has an intracellular half life of greater than about 10 hours.

30. The method of claim 29, wherein the method comprises the in-vivo production of a sufficient amount of the therapeutically effective metabolite to allow for once a day dosing of the compound of formula I in the human patient in the range of about 10 µg/kg to about 30 mg/kg.

31. The method of claim 30, wherein the once a day dosing of a compound of formula I in the human patient ranges from about 15 µg/kg to about 25 mg/kg.

32. The method of claim 27, wherein the compound according to claim 1 has a plasma half life great than about 2 hours in the patient.

\* \* \* \* \*